United States Patent
Geddes

(10) Patent No.: US 10,024,794 B2
(45) Date of Patent: Jul. 17, 2018

(54) DIRECTIONAL SURFACE PLASMON COUPLED FLUORESCENCE AND CHEMILUMINESCENCE FROM THIN FILMS OF NICKEL, IRON OR PALLADIUM AND USES THEREOF

(75) Inventor: Chris D. Geddes, Bel-Air, MD (US)

(73) Assignee: UNIVERSITY OF MARYLAND, BALTIMORE COUNTY, Baltimore, MD (US)

(*) Notice: Subject to any disclaimer, the term of this patent is extended or adjusted under 35 U.S.C. 154(b) by 1615 days.

(21) Appl. No.: 13/202,895

(22) PCT Filed: Feb. 23, 2010

(86) PCT No.: PCT/US2010/000542
§ 371 (c)(1),
(2), (4) Date: Sep. 29, 2011

(87) PCT Pub. No.: WO2010/096204
PCT Pub. Date: Aug. 26, 2010

(65) Prior Publication Data
US 2012/0021443 A1 Jan. 26, 2012

Related U.S. Application Data

(60) Provisional application No. 61/154,636, filed on Feb. 23, 2009, provisional application No. 61/154,568, filed on Feb. 23, 2009.

(51) Int. Cl.
*G01N 33/00* (2006.01)
*G01N 21/64* (2006.01)
(Continued)

(52) U.S. Cl.
CPC ..... *G01N 21/648* (2013.01); *G01N 33/54373* (2013.01); *G01N 33/553* (2013.01)

(58) Field of Classification Search
None
See application file for complete search history.

(56) References Cited

U.S. PATENT DOCUMENTS 5,017,009 A 5/1991 Schutt et al.
5,449,918 A 9/1995 Krull et al.
(Continued)

FOREIGN PATENT DOCUMENTS

JP 2001021565 1/2001
WO WO1989/09408 5/1989
(Continued)

OTHER PUBLICATIONS

Geddes (2004) J Fluor 14:119-123.*
(Continued)

*Primary Examiner* — Melanie Yu Brown
*Assistant Examiner* — Richard Moerschell
(74) *Attorney, Agent, or Firm* — Tristan A. Fuierer; Marianne Fuierer; Moore & Van Allen, PLLC

(57) ABSTRACT

Nickel, iron and palladium thin films thermally evaporated onto glass supports are used to demonstrate surface plasmon coupled fluorescence (SPCF) and surface plasmon couple chemiluminescence (SPCC) over a broad wavelength range (400-800 nm) for potential assays or other detection systems. Nickel, iron and palladium thin films used in SPCF and SPCC convert otherwise isotropic emission into highly directional and polarized emission, an attractive concept for surface assays. The emission angles of detected emissions occur over a 10 degree range for tested emitted wavelengths.

6 Claims, 41 Drawing Sheets

(51) Int. Cl.
*G01N 33/543* (2006.01)
*G01N 33/553* (2006.01)

(56) References Cited

U.S. PATENT DOCUMENTS

| | | | |
|---|---|---|---|
| 5,866,433 | A | 2/1999 | Schalkhammer et al. |
| 7,095,502 | B2 | 8/2006 | Lakowicz et al. |
| 7,253,452 | B2 | 8/2007 | Steckel et al. |
| 7,348,182 | B2 | 3/2008 | Martin et al. |
| 7,351,590 | B2 | 4/2008 | Martin |
| 7,400,397 | B2 | 7/2008 | Lakowicz et al. |
| 7,648,834 | B2* | 1/2010 | Moore ............... 435/287.1 |
| 7,718,445 | B2 | 5/2010 | Martin |
| 7,718,804 | B2 | 5/2010 | Geddes et al. |
| 7,732,215 | B2 | 6/2010 | Geddes et al. |
| 7,939,333 | B2 | 5/2011 | Geddes et al. |
| 8,008,067 | B2 | 8/2011 | Geddes et al. |
| 8,034,633 | B2 | 10/2011 | Geddes |
| 8,075,956 | B2 | 12/2011 | Geddes et al. |
| 8,722,428 | B2* | 5/2014 | Geddes ............... G01N 21/6408 436/525 |
| 2003/0228682 | A1* | 12/2003 | Lakowicz ......... G01N 21/6408 435/287.2 |
| 2004/0150818 | A1* | 8/2004 | Armstrong ............. B82Y 10/00 356/301 |
| 2005/0025676 | A1* | 2/2005 | Ehrfeld ................ G01B 11/065 436/164 |
| 2005/0053974 | A1 | 3/2005 | Lakowicz et al. |
| 2005/0186565 | A1 | 8/2005 | Malak |
| 2006/0147927 | A1 | 7/2006 | Geddes et al. |
| 2006/0194346 | A1 | 8/2006 | Knoll |
| 2006/0216696 | A1* | 9/2006 | Goguen ............. G01N 33/54326 435/5 |
| 2007/0269826 | A1 | 11/2007 | Geddes et al. |
| 2008/0174774 | A1 | 7/2008 | Bratkovski |
| 2008/0215122 | A1 | 9/2008 | Geddes et al. |
| 2009/0021727 | A1* | 1/2009 | Sepulveda Martinez .............. G01N 21/553 356/128 |
| 2009/0022766 | A1 | 1/2009 | Geddes et al. |
| 2009/0325199 | A1 | 12/2009 | Geddes et al. |
| 2010/0062545 | A1 | 3/2010 | Geddes et al. |
| 2010/0209937 | A1 | 8/2010 | Geddes et al. |
| 2010/0297016 | A1 | 11/2010 | Geddes et al. |
| 2011/0020946 | A1 | 1/2011 | Geddes |
| 2011/0129942 | A1* | 6/2011 | Ohtsuka ................ G01N 21/648 436/501 |
| 2011/0207236 | A1 | 8/2011 | Geddes |
| 2011/0285986 | A1* | 11/2011 | Wang et al. .............. 356/152.1 |
| 2012/0028270 | A1* | 2/2012 | Geddes ............. G01N 33/54373 435/7.1 |
| 2012/0282630 | A1* | 11/2012 | Geddes ................ G01N 21/648 435/7.9 |

FOREIGN PATENT DOCUMENTS

| | | |
|---|---|---|
| WO | WO2004/024191 | 3/2004 |
| WO | WO2006/074130 | 7/2006 |
| WO | WO2010/033677 | 3/2010 |
| WO | WO2010/096414 | 8/2010 |

OTHER PUBLICATIONS

Chowdhury (2006) J Fluor 16:295-299.*
Yu (2003) Anal Chem 75:2610-2617.*
Chowdhury (2006) Ap Phys Ltr 88:173104-1 to 173104-3.*
Johnson and Christy (1972) Phys Rev 6: 4370-4379 (Year: 1972).*
Johnson and Christy (1974) Phys Rev 9:5056-5070 (Year: 1974).*
https://www.thermofisher.com/us/en/home/brands/molecular-probes/key-molecular-probes-products/alexa-fluor/alexa-fluor-dyes-brightest-conjugates.html downloaded Dec. 3, 2017 (Year: 2017).*

Aslan, Kadir et al. "Directional, Broad, and Fixed Angle Surface Plasmon Coupled Fluorescence from Iron Thin Films." Journal of Physical Chemistry C, vol. 113, No. 48, Dec. 3, 2009, p. 20535-20538; figure 1.
Aslan, Kadir et al. "Surface plasmon coupled chemiluminescence from zinc substrates: Directional chemiluminescence." Applied Physics Letters, AIP, American Institute of Physics, vol. 94, No. 7, Feb. 17, 2009, pp. 73104-73104; figures 1-3.
Aslan, Kadir et al. "Metal-Enhanced Fluorescence from Nanoparticulate Zinc Films." Journal of Physical Chemistry C, vol. 112, Nov. 5, 2008, pp. 18368-18375; figures 1A, 8B.
Mayer, C. et al. "Robust nano cluster layers for structural amplified fluorescence biochips." Reviews on Advanced Materials Science Advanced Study Center Russia, vol. 5, No. 1, 2003, pp. 53-56.
Chowdhury, Mustafa et al. "Multicolor Directional Surface Plasmon-Coupled Chemiluminescence." The Journal of Physical Chemistry B, vol. 110, No. 45, Nov. 1, 2006, pp. 226444-22651; figure 1.
Pribik, R. et al. "Metal-Enhanced Fluorescence from Chromium Nanodeposits." Journal of Physical Chemistry C, vol. 112, No. 46, Nov. 20, 2008, pp. 17969-17973.
Weisenberg, M. et al. "Directional surface plasmon coupled chemiluminescence from nickel thin films: Fixed angle observation." Chemical Physics Letters, vol. 473, No. 1-3, Apr. 29, 2009, pp. 120-125; figures 1, 2A.
Anantha, V., and Taflove, A., Efficient modeling of infinite scatterers using a generalized total-field/scattered-field FDTD boundary partially embedded within PML, (2002) *Ieee Transactions on Antennas and Propagation* 50, 1337-1349.
Aslan, K., Badugu R., Lakowicz, J.R., Geddes, C.D, Metal-Enhanced Fluorescence from Plastic Substrates, (2005) *Journal of Fluorescence* 15, 99-104.
Aslan, K., Gryczynski, I., Malicka, J., Lakowicz, J. R. and Geddes, C. D. (2005) Metal-Enhanced Fluorescence: Application to High-Throughput Screening and Drug Discovery, in Drug Discovery Handbook (ed S. C. Gad), John Wiley & Sons, Inc., Hoboken, NJ, USA.ch14.
Aslan, K., Lakowicz, J.R., and Geddes, C.D., Metal-enhanced fluorescence using anisotropic silver nanostructures: critical progress to date, (2005) *Analytical and Bioanalytical Chemistry* 382, 926-933.
Aslan, K., Lakowicz,J.R., Szmacinski, H., and Geddes, C.D., Metal-enhanced fluorescence solution-based sensing platform, (2004) *Journal of Fluorescence* 14, 677-679.
Aslan, K., Lakowicz, J.R., Geddes, C.D., Nanogold-plasmon-resonance-based glucose sensing , (2004) *Analytical Biochemistry* 330, 145-155.
Aslan, K., Leonenko, Z., Lakowicz, J.R., and Geddes, C.D., Fast and slow deposition of silver nanorods on planar surfaces: Application to metal-enhanced fluorescence, (2005) *Journal of Physical Chemistry B* 109, 3157-3162.
Aslan, K., Leonenko, Z., Lakowicz, J.R., Geddes, C.D., Annealed Silver-Island Films for Applications in Metal-Enhanced Fluorescence: Interpretation in Terms of Radiating Plasmons (2005) *Journal of Fluorescence* 15, 643-654.
Aslan, K., Gryczynski, I., Malicka, J., Matveeva, E., Lakowicz, J.R., and Geddes, C.D., Conversion of just-continuous metallic films to large particulate substrates for metal-enhanced fluorescence (2005) *Current Opinion in Biotechnology* 16, 55-62.
Aslan, K., Lakowicz, J.R., and Geddes, C.D., Metal-enhanced fluorescence using anisotropic silver nanostructures: critical progress to date. (2005) *Journal of Physical Chemistry B* 109, 6247-6251.
Aslan, K., Malyn, N., and Geddes, C.D., Metal-enhanced fluorescence from gold surfaces: Angular dependent emission, (2007) *J Fluoresc* 15, 7-13.
Aslan, K.; Malyn, S. N.; Geddes, C. D., Microwave-accelerated surface plasmon-coupled directional luminescence: Application to fast and sensitive assays in buffer, human serum and whole blood (2007) *Journal of Immunological Methods*, 323, 5564.
Aslan, K., Malyn, S.N., Bector, G., and Geddes, C.D., Microwave-accelerated metal-enhanced fluorescence: an ultra-fast and sensitive DNA sensing platform, (2007) *Analyst* 132, 1122-9.

(56) References Cited

OTHER PUBLICATIONS

Aslan, K., Previte, M.J.R., Zhang, X.Y., Baillie, L., and Geddes, C.D., Ultra-fast and sensitive DNA hybridization assays: Application to genomic anthrax detection in < 30 seconds, (2007) *Biophysical Journal*, 552A-552A.

Aslan, K., Zhang, Y., Hibbs,S., Baillie, L., Previte, M.J., Geddes, C.D., Microwave-accelerated metal-enhanced fluorescence: application todetection of genomic and exosporium anthrax DNA in ,30 seconds (2007) *Analyst* 132, 1130-8.

Aslan, K.,Previte, M.J.R., Zhang and Geddes, C.D., Metal-Enhanced Fluorescence from Nanoparticulate Zinc Films, (2008) Journal of Physical Chemistry C. 112, 18368-18375.

Aslan, K., Zhang, Y.X., and Geddes, C.D., Conversion of just-continuous metallic films to large particulate substrates for metal-enhanced fluorescence, (2008) *Journal of Applied Physics* 103, 084307.

Aslan, K.; Previte, M. J.; Zhang, Y.; Geddes, C. D., Extraction and Detection of DNA from Vacillus anthracis Spores and the Vegetative Cells within 1 min., (2008) *Anal Chem*, 80, 7304-7312.

Barnes, WL, Fluorescence near interfaces: the role of photonic mode density, (2005) *Journal of Modern Optics* 45, 661.

C. D. Geddes, CD and J. R. Lakowicz, JR., Metal-Enhanced Fluorescence (2002) *Journal of Fluorescence* 12, 121-129.

Drexhage, KH, Influence of a Dielectric Interface on Fluorescence Decay Time, (1970): J. Luminesc, 693-701.

Gryczynski, I.; Malicka, J.; Gryczynski, Z.; Nowaczyk, K.; Lakowicz, J. R., Ultraviolet surface plasmon-coupled emission using thin aluminum films, (2004) *Analytical Chemistr*, 76, 4076-4081.

Gryczynski, I.; Malicka, J.; Nowaczyk, K.; Gryczynski, Z.; Lakowicz, J. R., Effects of sample thickness on the optical properties of surface plasmon-coupled emission, (2004) *Journal of Physical Chemistry B*, 108, 12073-12083.

Knoll, W., Interfaces and thin films as seen by bound electromagnetic waves, (1998) *Annu Rev Phys Chem*, 49, 569-638.

Knoll, W.; Zizlsperger, M.; Liebermann, T.; Arnold, S.; Badia, A.; Liley, M.; Piscevic, D.; Schmitt, F. J.; Spinke, J., Streptavidin arrays as supramolecular architectures in surface-plasmon optical sensor formats, (2000) *Colloids and Surfaces A—Physicochemical and Engineering Aspects*, 161, 115-137.

Kwon, S. H.; Hong, B. J.; Park, H. Y.; Knoll, W.; Park, J. W., DNA-DNA interaction on dendron-functionalized sol-gel silica films followed with surface plasmon fluorescence spectroscopy, (2007) *J Colloid Interface Sc*, 308, 325-331.

Liebermann, T.; Knoll, W.; Sluka, P.; Herrmann, R., Complement hybridization from solution to surface-attached probe-oligonucleotides observed by surface-plasmon-field-eahanced fluorescence spectroscopy, (2000) *Colloids and Surfaces A—Physicochemical and Engineering Aspects*, 169, 337-350.

Liebermann, T.; Knoll, W., Surface-plasmon field-enhanced fluorescence spectroscopy, (2000) *Colloids and Surfaces A—Physicochemical and Engineering Aspects*, 171, 115-130.

Liu, J.; Tiefenauer, L.; Tian, S.; Nielsen, P. E.; Knoll, W., PNA-DNA hybridization study using labeled streptavidin by voltammetry and surface plasmon fluorescence spectroscopy, (2006) *Anal Chem*, 78, 470-476.

Matveeva E., Gryczynski, Z., Myoglobin Immunoassay Utilizing Directional Surface Plasmon-Coupled Emission, Anal. Chem. 2004, vol. 76 pp. 6287-6292, see figures 1-3.

Previte, M. J. R.; Zhang, Y. X.; Aslan, K.; Geddes, C. D. Surface plasmon coupled fluorescence from copper substrates, (2007) *Applied Physics Letter*, 91, 15, 1519021-3.

Pribik, R., Aslan, K., Zhang, Z., and Geddes, C.D., Metal-Enhanced Fluorescence from Chromium Nanodeposits, (2008) *Journal of Physical Chemistry C.*, 112, 17969-17973.

G. Bauer, F. Pittner and Th. Schalkhammer, Metal Nano-Cluster Biosensors, Mikrochim. Acta 131, 107-114 (1999).

Th. Schalkhammer, Metal Nano Clusters as Transducers for Bioaffinity Interactions, Monatschefte für Chemie 129, 1067-1092 (1998).

Strekal, N., Maskevich, A., Maskevich,S., Jardillier, J.C., Nabiev, I., Selective Enhancement of Raman or Fluorescence Spectra of Biomolecules Using Specifically Annealed Thick Gold Films (2000) *Biopolymers* 57, 325-8.

Tawa, K.; Yao, D.; Knoll, W., Matching base-pair number dependence of the kinetics of DNA-DNA hybridization studied by surface plasmon fluorescence spectroscopy (2005) *Biosens Bioelectron*, 21, 322-329.

Yu, F.; Persson, B.; Lofas, S.; Knoll, W., Attomolar sensitivity in bioassays based on surface plasmon fluorescence spectroscopy, (2004) *J Am Chem Soc*, 126, 8902-8903.

Zhang, Z., Aslan, K., Previte, M.J.R., and Geddes, C.D. Metal-enhanced fluorescence from copper substrates , (2007) *Applied Physical Letters* 90, 173116.

Zhang, Y., Aslan, K., Previte, M.J.R., and Geddes, C.D., Plasmonic engineering of singlet oxygen generation, (2008) *Proceedings of the National Academy of Sciences of the United States of America* 105, 1798-1802.

Knoll, Wolfgang; "Interfaces and Thin Films as Seen by Bound Electromagnetic Waves," Annu. Rev. Phys. Chem., 1998, pp. 569-638, vol. 449.

Liebermann, Thorsten, et al.; "Surface-plasmon field-enhanced fluorescence spectroscopy," Colloids and Surfaces A: Physicochemical and Engineering Aspects, 2000, pp. 115-130, vol. 171.

\* cited by examiner

DIRECTIONAL SURFACE PLASMON COUPLED FLUORESCENCE AND CHEMILUMINESCENCE FROM THIN FILMS OF NICKEL, IRON OR PALLADIUM AND USES THEREOF

CROSS-REFERENCE TO RELATED APPLICATIONS

This application is filed under the provisions of 35 U.S.C. § 371 and claims the priority of International Patent Application No. PCT/US2010/000542 filed on Feb. 23, 2010, which in turn claims priority to U.S. Provisional Patent Application Nos. 61/154,568 and 61/154,636 both filed on Feb. 23, 2009 the contents of which are hereby incorporated by reference herein for all purposes.

BACKGROUND OF THE INVENTION

Field of the Invention

The present invention relates to electromagnetic emissions from fluorescence, chemiluminescence, bioluminescence, and luminescence molecule, and more specifically, to detection of such emissions in wavelengths from UV-visible to near IR and at a directional or fixed angle.

Background of Related Technology

Surface plasmon fluorescence spectroscopy (SPFS),[1] a technique that utilizes the interactions of fluorescent species with thin metal films, is becoming a useful tool in the analytical biosciences. In SPFS, fluorescent species typically attached to biomolecules that are brought within close proximity to the metal surface via biorecognition events between metal surface bound biomolecules and the fluorescently-labeled biomolecules as part of the bioassays constructed on the metal surface. The fluorescence emission detected from the sample side (free-space emission) or through the prism (surface plasmon coupled fluorescence, SPCF) is then used to quantify the biomolecule of interest. In this regard, attomolar sensitivity in immunoassays based on SPFS has been reported.[2] One can also find other reports on SPSF for DNA hybridization[3-5] and protein detection.[6]

In SPFS, two modes of excitation of the fluorescent species can be achieved: 1) Kretschmann (KR) configuration: through a prism, 2) reverse Kretschmann (RK) configuration: directly from the air or sample side.[1] The description of both modes of excitation has been given elsewhere.[7] In fluorescence-based biosensing applications that utilize optically dense medium, such as whole blood, the KR configuration is typically considered for the excitation of fluorescent species. This is due to the effective excitation of fluorescent species by the excitation light in the form of an evanescent wave which penetrates several hundred nanometers into the optically dense medium from the surface of the metal. On the other hand, in RK configuration, the efficiency of excitation of the fluorescent species in optically dense medium can be considerably less than as compared to KR due to the sample thickness and inner filter effect. Regardless of the excitation mode, the fluorescence emission can be detected as both free-space isotropic emission and/or highly directional SPCF emission. One can visually see the SPCF emission as a cone or as a "ring" from the back of the film when a hemispherical prism is employed.

The choice of metal in SPSF is usually gold[1,8] since it is inert and amenable to chemical modification without the loss of physical and electronic properties. Despite their versatility, the use of gold thin films is limited to the visible spectral range. In recent years, there has been a resurgence in the investigation of other metals to alleviate this problem: silver[9] and aluminum[10] and zinc thin films[7] were shown the work in the UV and UV to visible spectral range, respectively. It was also shown that copper thin films[11] can also be used with fluorophores emitting >550 nm. It is important to also note that the angle of reflectivity minimum varies with the type and thickness of the metal used due to the optical properties of the metal. In this regard, Fresnel calculations have been shown to be an excellent tool for prediction of the interaction of light with metals.

Near-infrared fluorescence is attractive in many settings such as in optical imaging and immunoassays, because it circumvents some of the problems associated with fluorescence in the visible region. However, the detection limits and sensitivity are still limited by the photostability and quantum yield of the near IR-fluorophore (label) and therefore still remain a primary concern in fluorescence spectroscopy and imaging today. Thus, it would be advantageous to develop a system that provides strong signals with increased photostability for a near IR-fluorophore. As such, there is a continued search for metal(s) that can function in a broad wavelength range with the possibility of covering the wavelengths for many commercially available fluorophores. That is, a single metal thin film can utilize fluorophores from the UV to NIR without the need to change metal.

Chemiluminescence is a very useful analytical technology for the quantitative detection of biomolecules of interest. Chemiluminescence emission, which is a result of chemical reactions between an organic dye and an oxidizing agent in the presence of a catalyst, is the primary tool in this technology. Chemiluminescence emission occurs as the energy from the excited states of organic dyes, which are chemically induced, decays to ground state. The duration and the intensity of the chemiluminescence emission are mostly dependent on the extent of the chemical reagents present in the reaction solution. Despite the usefulness of the chemiluminescence technology, chemiluminescence emission is isotropic and the efficiency of detection of chemiluminescence emission by current optical detectors is very low. In this regard, the chemiluminescence technology still requires much needed improvement in the efficiency of detection of chemiluminescence emission.

Thus it would be advantageous to overcome the shortcomings discussed above and it would be ideal to develop a system to wherein the reflectivity minimum for such a metal thin film would occur at a fixed wavelength, which would alleviate the need to change the observation angle, which is one of the disadvantages of using silver, gold, copper and/or zinc thin films.

SUMMARY OF THE INVENTION

The present invention relates methods of enhancing emissions from fluorescence, chemiluminescence, bioluminescence, and luminescence molecules, both intrinsic and extrinsic, and reactions that exhibit emissions in wavelengths from UV-visible to near IR.

The present invention relates to detection methods using plasmonic emissions from metallic surfaces, both thin films and nanostructures, caused by fluorescence or luminescence molecules and chemiluminescence or bioluminescence based reactions. These plasmonic emissions emitted from metallic surface plasmons are generated either with an external excitation or without such external excitation due to chemically induced electronically excited states.

The present invention relates to a system for providing direction and fixed angle detection, the system comprising;

a) a substrate comprising a thin layer of metallic material, wherein the metallic material is nickel, iron or palladium comprising a film layer in a thickness from about 1 to 25 nm;
b) at least one energy emitting molecule that is positioned near the metallic material in a range from about 5 nm to 100 nm; wherein the energy emitting molecule has an emission wavelength in the range of about 400 to 900 nm;
c) a source of electromagnetic energy or a chemical trigger agent for providing excitation energy to excite the energy emitting molecule;
d) a detector for detecting directional emissions from the excited energy emitting molecule and/or the metallic surface.

Importantly, the detected emissions are directional and at a fixed 10 degree wide observation angle for the nickel, iron and palladium thin metallic layers.

Another aspect of the invention relates to a method of enhancing emissions from fluorescence, luminescence molecules and chemical reactions such as reaction that exhibit chemiluminescence and bioluminescence, all of which exhibit emissions in UV/visible/near IR wavelengths.

Preferably, the metallic surfaces take the form of thin metallic films, ranging from 5 to 25 nm. In the alternative, metallic islands, nanostructures, colloids or porous matrix may be used.

In yet another aspect, the present invention relates to a method of metal-enhanced luminescence sensing, comprising:
a) applying a Ni, Pd, or Fe metallic material to a surface used in a detection system;
b) introducing a solution containing at least one excitable molecule for disposing near the metallic surface, wherein the molecule is capable of a chemically induced electronically excited state or radiatively excited state, wherein the radiatively excited state is induced by application of electromagnetic energy;
c) triggering the chemically induced electronically excited state or radiatively excited of the excitable molecule; and
d) detecting the directional emissions for measuring the luminescent intensity, wherein the luminescence includes fluorescence, chemiluminescence and bioluminescence.

In yet another aspect, the present invention relates to a method for detecting a target molecule in a sample, the method comprising:
a) providing a system comprising:
  i. a layer of immobilized Ni, Pd or Fe metallic film or particles positioned on a surface substrate, wherein the immobilized Ni metallic film or particles have attached thereto a captured biomolecular probe with an affinity for the target molecule; and
  ii. a free biomolecular probe with an affinity for the target molecule, wherein the free biomolecular probe has attached thereto a fluorophore;
b) contacting the sample with the immobilized biomolecular probes, wherein the target molecules binds to the immobilized biomolecular probes; and
c) contacting the bound target molecule with the free biomolecular probe, wherein binding of the free biomolecular probe to the target molecule causes the fluorophore to be positioned a sufficient distance from the immobilized metal particles to enhance fluorescence emission when excited by an irradiating source.

In yet another aspect, the present invention relates to a detection system for determining a target molecule in an optically dense material, the system comprising:
a) a metallic material applied to at least a portion of a substrate surface, wherein the metallic material is Ni, Pd or Fe;
b) a fluid comprising the optically dense material and at least one fluorescent species exhibiting an emission wavelength from UV to NIR, wherein the fluorescent species has the ability to attach to the target molecule;
c) a container for holding the fluid and wherein the at least one fluorescent species attached to any target molecule, wherein the fluorescent species is positioned from the metallic material at a distance sufficient to enhance emission intensity;
d) a source of electromagnetic energy for applying excitation energy to the at least one fluorescent species in the detection system; and
e) a detector positioned at a detection angle for measuring fluorescence emission;

A further aspect of the present invention, relates to a kit for detecting a target molecule in a sample, the kit comprising
a) a container including metallic particles that are fabricated of a metallic material that generate plasmonic emissions when irradiated with electromagnetic energy, wherein the metallic material is Ni, Pd or Fe, wherein the metallic particles are sized to scatter light and comprise immobilized receptors or probes and wherein the immobilized receptors or probes have an affinity for the target molecule in a test sample.

Yet another aspect relates to a system for providing increased detection limits and photostability of a near IR-fluorophore, the system comprising;
a) a substrate comprising a thin layer of metallic material, wherein the metallic material is nickel comprising a film layer in a thickness from 1 to 15 nm;
b) at least one fluorophore that is positioned near the metallic material in a range from about 5 nm to 40 nm; wherein the fluorophore has an emission wavelength in the range of 420 to 900 nm;
c) a source of electromagnetic energy for providing excitation energy to excite the fluorophore; and
d) a detector for detecting emissions from the fluorophore and/or the metallic surface.

Preferably, the metallic material takes the form of metallic islands, nanostructures, colloids, porous matrix or a continuous metallic surface. The substrate for all embodiments may include, glass, quartz, cellulose and/or a polymeric material.

Other aspects and advantages of the invention will be more fully apparent from the ensuing disclosure and appended claims.

DETAILED DESCRIPTION OF THE INVENTION

Figure 1:
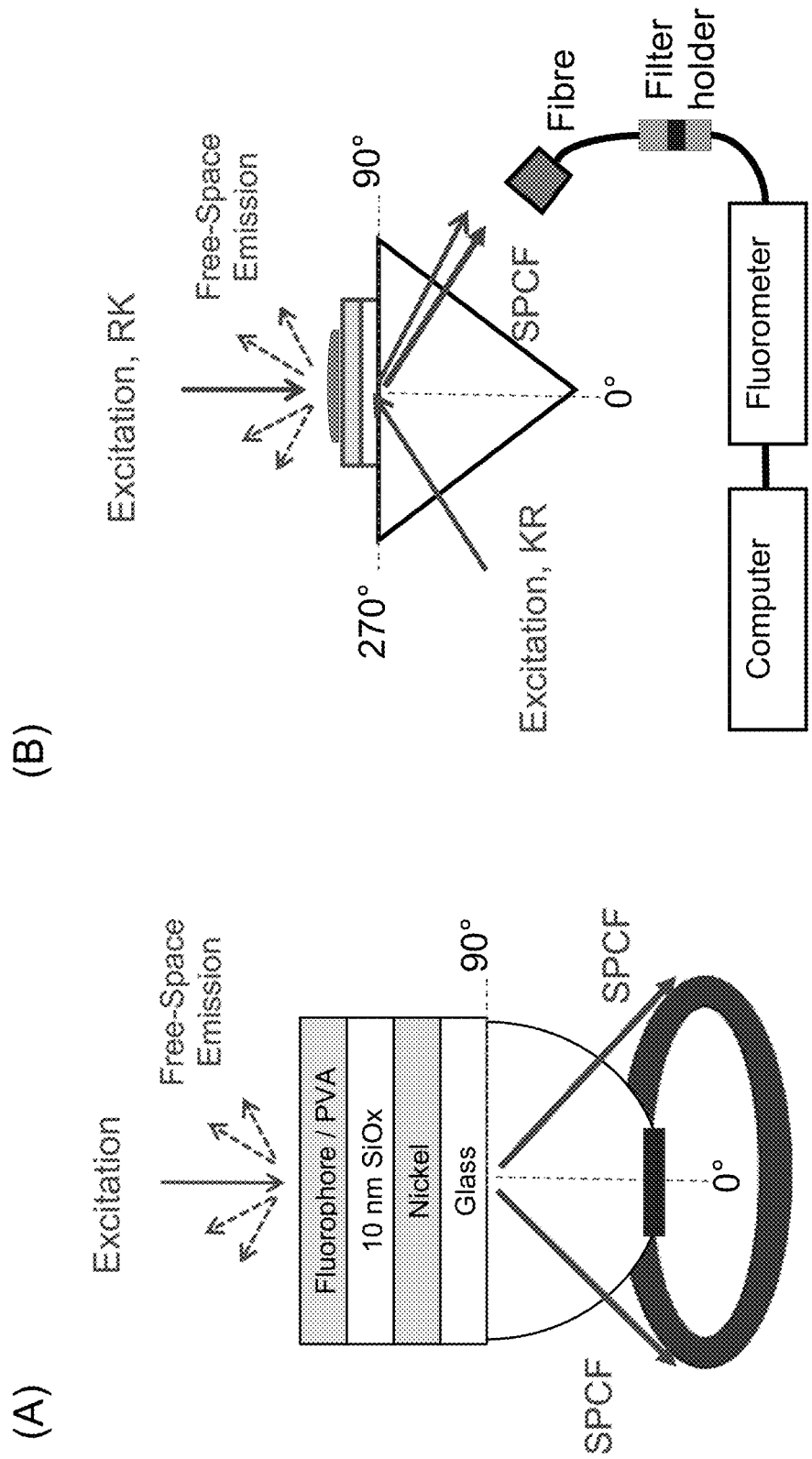
FIG. 1 shows a schematic representation of experimental setup for Surface Plasmon Coupled Fluorescence (SPCF) measurements carried out with (A) a hemispherical prism is used to collect the "ring" of emission and from nickel substrates (B) a 45-degree prism that affords for Kretschmann (KR) and Reverse Kretschmann (RK) geometries to be used.

Surface plasmons are collective oscillations of free electrons at metallic surfaces. When a metallic article or surface is exposed to an electromagnetic wave, the electrons in the metal (plasmons) oscillate at the same frequency as the incident wave. Subsequently, the oscillating electrons radiate electromagnetic radiation with the same frequency as the oscillating electrons. It is this re-radiation of light at the same incident wavelength that is often referred to as plasmon emission. In the present invention chemically or radiatively induced electronic excited states couple to surface plasmons to produce emission intensities greater than from about 5 to 1000-fold, as compared to a control sample containing no metallic surface.

Fluorophore," as used herein, means any substance that can be excited by electromagnetic energy and induce a mirror dipole metallic surface in close proximity to the metallic surface and is intended to encompass a chemical or biochemical molecule or fragments thereof that is capable of interacting or reacting specifically with an analyte of interest in a sample to provide one or more optical signals.

Fluorophore within its meaning can include but not limited to, Quantum Dots (Qdots); Chemiluminescence Alkaline Phosphatase and other chemiluminescence labels; Fluorospheres, i.e. fluospheres and Transfluospheres; Polymer beads doped with one or more fluorescent labels; Fluorescent Microspheres; Silicon nanoparticles; Silica and silicate doped materials; Semi conductor materials; E-type fluorescent luminophores; P-type fluorescent luminophores; Fluo-3 and Fluo-4 Calcium indicators; Calcium Green indicator; Fluozin Zinc indicators; Phen Green for the detection of a broad range of ions including Cu2+, Cu+ etc; Newport Green for the detection of Zn2+; Leadmium Green dye for the measurement of lead and cadmium; Magnesium green for the electric detection of free magnesium; Mag-fura-2 and Mag-indo-1 for magnesium detection; Mag-fluo-4 for both calcium and magnesium detection in both free solution and intercellular; Phycobiliproteins (many different forms); Bucky balls, $C_{60}$ etc; Carbon nanotubes; Cardio green/indocyanine green fluorescent indicators; Metallic colloids of Ag, Au, Pt, Fe Pd, Cu, Zn, Rh, Cr, Pb etc and mixed colloidal metal combinations; pH indicators such as SNARF-1, SNARF-4F, SNARF-5F, Dextran BCECF etc; 6-chloro-9-nitro-5-oxo-5H-benzo{a}phenoxazine (CNOB) for the detection of nitroreductase and nitrate reductase activity; SYTOX dead cell stains, such as SYTOX Blue, green, Orange, Red; DAPI and the Propidium Iodide labels; Probes for double stranded DNA detection such as Ethidium bromide, Picogreen and Syber green; Alexa fluorophore range of dyes; BODIPY and related structural dyes; Cellular and Organelle lights (genetically encoded proteins); Green Fluorescent Protein (GFP) and its analogues; Coumarin dyes; Prodan and related structural dyes; Voltage sensitive probes such as $DisBAC_4(3)$ and CC2-DMPE; and/or Ncode miRNA labeling fluorophores Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl) naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phosphatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 lodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1, 4', 6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, green fluorescent proteins and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Embodiments of the present invention are applicable to chemiluminescence labels or moieties which participate in light-producing reactions in the presence of a triggering agent or cofactor. In the present application, for purposes of example and without limitation, a preferred embodiment will be discussed in terms of chemiluminescence labels and triggering agent. The label affixed to the detector molecule will be referred to as the "label" or "label agent". For purposes herein, "triggering agent or cofactor" is broadly used to describe any chemical species, other than the chemiluminescence labels which participate in a reaction and which produces a detectable response. Chemiluminescence labels and triggering agents produce a light response.

Examples of suitable chemiluminescence labels include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen.

Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) proprionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

Techniques for attaching antibodies or antigens to solid substrates are also well known in the art. For example, antibodies may be coupled covalently using glutaraldehyde to a silane derivative of borosilicate glass.

The term "biomolecule" means any molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Preferably, the biomolecule has a dipole moment when excited and thus can induce a mirror dipole in a metallic material in close proximity. Exemplary biomolecules include nucleic acids, aromatic carbon ring structures, NADH, FAD, amino acids, carbohydrates, steroids, flavins, proteins, DNA, RNA, oligonucleotides, peptide, nucleic acids, fatty acids, myoglobin, sugar groups such as glucose etc., vitamins, cofactors, purines, pyrimidines, formycin, lipids, phytochrome, phytofluor, peptides, lipids, antibodies, bilirubin, tryptophan and phycobiliproptein.

There are many important assays that can directly benefit from immediate readouts and quicker kinetics. For example, myoglobin concentrations for heart attack patients, patients of toxic shock and pancreatitis. Thus, the present invention may optionally include the use of microwave energy or sonic energy to increase any reaction rates in an assay detection system.

Microwave radiation may be provided by an electromagnetic source having a frequency in a range between 0.3 and 10 GHz, more preferably from about 1 GHz and 5 GHz, and a power level in a range between about 10 mwatts and 400 watts, preferably from 30 mwatts to about 200 watts, and more preferably from about 50 watts to 300 watts. Any source, known to one skilled in the art may be used, such as a laser having the capacity to emit energy in the microwave range. The microwave radiation may be emitted continuously or intermittently (pulsed), as desired, to maintain the metallic particles at a predetermined temperature such that it is capable of increasing the speed of chemical reactions not only in the assay system but also the luminescence species.

In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

In one embodiment the present invention provides for a metallic surface and a molecule capable of luminescing, wherein the metallic surface and the molecule are separated by at least one film spacer layer. The thickness of said film may be chosen so as to enhance the luminescence of the molecule by positioning the molecule an optimal distance from the metallic surface. The film spacer layer may be one or multiple layers of a polymer film, a layer formed from a fatty acid or a layer formed from an oxide. In a preferable embodiment, the film spacer layers and the metallic surface are chemically inert and do not bind to the molecules to be detected or to intermediates that are bound to the compounds to be detected, for example covalently bound. The layer formed from a fatty acid may be formed by a Langmuir-Blodgett technique. The film spacer layer may be a spin coated polymer film. The oxide layer may be formed from a deposition technique, such as vapor deposition.

The emission enhancement may be observed at distances according to the type of luminescence species to be detected and the type of metal. For example, emission enhancement may be observed when a luminescence species is positioned about 4 nm to about 200 nm to metal surfaces. Preferable distances are about 4 nm to about 30 nm, and more preferably, 4 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Various optical detectors, such as photodiode, charge-coupled device (CCD), photomultiplier tube (PMT), or photon counting detector, have different degree of sensitivity and may be used in the present invention. PMT and photon counting detectors can achieve an electronic amplification factor as high as $10^6$-$10^8$. Conventional PMTs require a ~1 kV power source, but new miniaturized detector requires only a 5 V. Most of the chemiluminescence emission wavelengths are in the visible region. A narrow-band optical filter may be used to ensure detecting luminescence wavelengths. The system may include a microactuator, detector, microprocessor, electronics, a display, and translation stage. The output of the detector may be interfaced to an analog to digital converter and a microprocessor to calculate analyte concentration.

The assay systems of the present invention may further comprise a light or laser source for directing an energy beam on any included fluorophore to provide excitation energy. The laser beam may be positioned adjacent to the system for directing the beam at the molecular components. The laser may be any device capable of focusing an energy beam at a particular point on the solid or liquid source material for excitation and the laser may transmit RF, infrared, microwave to UV energy.

Any source, known to one skilled in the art may be used, such as a laser that emits light, wherein light is used in its broad sense, meaning electromagnetic radiation which propagates through space and includes not only visible light, but also infrared and ultraviolet radiation. Thus, a single instrument placed above the surface of the assay can be used to generate the energy to excite fluorescing molecules. The light can be emitted from a fiber continuously or intermittently, as desired.

Further, 2-photon excitation may be used at approximately 375 to 900 nm using continuous or short pulse width (<50 ps), high repetition rate (>1 MHz), laser diode sources. A variety of pulsed laser diode sources that will be compatible with fluorophores can be used with the present invention and are commercially available.

Still further, the present invention can be used with tunable Ti:Sapphire laser excitation and multiphoton microscopy.

The present invention provides for metallized islands of elliptical, spherical, triangular or rod-like forms. In exemplary cases, the elliptical islands have aspect ratios of 3/2, and the spherical colloids have diameters of 5-60 nm. However, the invention is not limited to any particular geometry. Using known coating techniques, the placement of metallic islands could be controlled precisely, as close as 10 to 50 nm apart.

In yet another embodiment, a surface substrate is modified by adhering metallic surfaces fabricated to form a geometric shape such as triangle, square, oblong, elliptical, rectangle, or any shape that provides at least one apex area of the metallic surface. Further multiple metallic geometric shapes may be adhered to a surface in the form of a pattern to provide at least one reactive zone positioned between the apex areas. It is envisioned that the apex area includes not only pointed regions but regions with rounded edges such as found in an oblong or elliptical shape. The apex areas are preferably arranged so that one apex area is opposite from another apex area and aligned to cause the reactive zone to be positioned therebetween.

The geometric shapes can be formed on the surface substrate by any means known to those skilled in the art, including masking the surface substrate with subsequent deposition of the metallic material, fixing preformed metallic geometric shapes directly onto the substrate surface, or impregnating a geometric shaped recess in the surface substrate with a metallic material that provides for a continuous planar surface on the substrate.

The metallic material may be in the form of a porous three dimensional matrix. The three dimensional matrix may be a nano-porous three dimensional matrix. The metallic material may include metal colloid particles and/or metal-silica composite particles. The metallic material may comprise agglomerated metal particles and/or binary linked particles or metal particles in a polymer matrix. The three dimensional matrix may be formed from controlled pore glasses or using matrices assembled from the aggregation of metal-silica composites themselves. The matrices may be metallic nanoporous matrix, through which species will flow and be both detected and counted more efficiently.

Different surface enhanced fluorescence effects are expected for sub-wavelength or semi-transparent metal surfaces, metallic island films or metal colloids. More dramatic effects are typically observed for islands and colloids as compared to continuous metallic surfaces. The metallic islands had the remarkable effect of increasing the intensity at least about 5-fold while decreasing the lifetime 100-fold. Such an effect can only be explained by an increase in the radiative decay rate. The island particles are prepared in clean beakers by reduction of metal ions using various reducing agents.

In one embodiment of the present invention, a detailed investigation of the utility of nickel thin films for surface plasmon coupled fluorescence spectroscopy is presented. Fresnel calculations were used to predict the optimum thickness of the nickel thin film and the wavelength range of light that can couple to the nickel thin films. The optimum thickness of the films was determined to be in the 15-20 nm range. The spectral regions of light that can couple to nickel thin films were calculated to be ≈344 to 1240 nm. Fresnel calculations predict the reflectivity minimum for nickel thin films to occur at a range of angles from 60-70 degrees for light at 428-827 nm. The experimental confirmation of Fresnel calculations for nickel thin films was undertaken with five different fluorophores with emission wavelengths falling in the range of 428-814 nm. The maximum value of SPCF emission intensity for all fluorophores occurred at an angle of ≈65 degrees as predicted by Fresnel calculations. From the experimental results it was concluded that 20 nm nickel thin films have potential utility in whole blood assays, which was demonstrated with a long wavelength fluorophore, Zn PhCy. Fresnel calculations were also used to predict the penetration depth of light (evanescent field), above the metal surface. It was calculated that the evanescent field penetrates to greater depth in solution than other metals used for SPFS to date, making nickel thin films an excellent choice of metal to be used in SPCF applications today.

Examples

Methods and Materials.

All fluorophores, 1,4-Bis(5-phenyl-2-oxazolyl)benzene (POPOP), fluorescein isothiocyanate (FITC), Zinc Phthalocyanine (Zn PhCy), Sulforhodamine 101(S101), Ir-780 Iodide (IR780), poly(vinyl)alcohol (PVA, 98% hydrolyzed 13,000-23,000 MW), Poly(methyl methacrylate) (PMMA, 100,000 MW), toluene, chloroform (99.8% ACS Reagent), whole blood, silicone isolator sample holders (press-to-seal) and Silane-prep™ glass microscope slides (were purchased from Sigma-Aldrich Chemical Company (Milwaukee, Wis., USA). Nickel thin films (15 and 20 nm) with 10 nm thick SiOx overlayer were separately deposited onto Silane-prep™ glass microscope slides by AccuCoat Inc., Rochester, N.Y., USA.

Sample Preparation. The method for the deposition of fluorophores onto metallic thin films was published elsewhere.[7] In short, fluorophores were deposited onto nickel thin films by spin coating a solution of polymers containing the fluorophores. Stock solutions of POPOP and Zn PhCy (1 mM) were prepared in toluene and mixed with a 5% PMMA solution to make a POPOP solution with the following final concentrations: 0.1 mM POPOP and 0.1 mM Zn PhCy in 1% PMMA. Stock solutions of FITC, S101 and IR780 (1 mM in water) were then diluted with a solution of 5% PVA in water.

The final concentrations of fluorophore/polymer solutions were adjusted to 0.1 mM of fluorophore and 0.1% PVA. Forty microliters of fluorophore/polymer solutions were spin-coated onto nickel thin films (1 cm×1 cm) using a Chemat Technology Spin Coater (Model KW-4A) with the following speeds: setting 1: 9 seconds, setting 2: 20 seconds. The thickness of the polymer films was previously measured to be ≈25 nm for 0.1% PVA films, and a 1% PMMA film. It was previously shown that the thickness of the polymer film spin coated onto metal films is dependent on the size of the support, the type and the settings of the spin coater itself.[7] Thus, similar solution preparation conditions and settings were used to reproduce the results presented in this study.

Silane-prep™ glass microscope slides were purchased from the Sigma-Aldrich Chemical Company (Milwaukee, Wis., USA). Nickel thin films (15 nm) with a 10 nm thick $SiO_2$ overlayer were deposited onto Silane-prep™ glass microscope slides by AccuCoat Inc., Rochester, N.Y., USA. Blue, green and turquoise chemiluminescent solutions were purchased from Omniglow (West Springfield, Mass.). These solutions are part of a chemiluminescent kit that contains reactants (hydrogen peroxide and diphenyl oxalate) to produce chemiluminescence emission, which were encapsulated within different glass tubes inside a plastic tube. A very intense chemiluminescence emission, lasting ≈2 hours, was observed after the glass tubes were broken and the chemicals were completely mixed.

Surface Plasmon Fluorescence Spectroscopy (SPSF). Free-space and SPCF emission measurements were made according to previously published methods.[7] In this regard, the fluorophore-coated nickel thin films were attached to a either a hemispherical or right-angle prism made of BK7 glass with index matching fluid, c.f. FIG. 1. The sample was excited using either the Kretschmann (KR) or Reverse Kretschmann (RK) configuration in SPSF measurements. A hemispherical prism was used only to collect the photographs of the SPCF "ring". The excitation of FITC, S101, Zn PhCy and IR780 was undertaken with a laser (473, 532, 594 and 594 nm, respectively) at an angle normal to the surface. The excitation of POPOP was from a UV light source (Mikropack D-2000 Deuterium) that was collimated to a 5 mm spot on the sample geometry at an angle normal to the surface using the RK configuration. The observations of the surface plasmon coupled and free-space emission were performed with a 600 um diameter fiber bundle, covered with a 200 um vertical slit, positioned about 15 cm from the sample. This corresponds to an acceptance angle below 0.1°. The output of the fiber was connected to an Ocean Optics HD2000+ spectrofluorometer to measure the florescence emission spectra through a 400, 600, 700, 800 nm long-pass filters for POPOP, S101, Zn PhCy and IR 780, respectively and a 488 nm super notch filter (Semrock) for FITC. Real-color photographs of the SPCF emission were taken through an emission filter used for the excitation of the samples placed on a hemi-spherical prism.

SPCF measurements in whole blood were performed using both KR and RK configurations. In this regard, various concentrations of Zn PhCy (emission peak at 710 nm) was mixed with whole blood (1:1 v/v) and placed in two different types of commercially available sample holders attached to nickel thin films. The dimensions of the circular sample holders were (diameter×depth): 2×1.5 mm or 9×2 mm. Total sample volume was 30 and 100 uL for the 2×1.5 mm or 9×2 mm sample holders, respectively.

Fresnel Calculations. Penetration depth calculations were performed for metals using three-phase (glass/metal/water) Fresnel calculations. The maximum value for the z-component of the electric field ($E_z^2$) that occurs at the angle of reflectivity minimum is normalized with respect to the highest value and plotted against the thickness (depth) above the metal.[12] Fresnel calculations (using a macro procedure written for Igor Pro software)[7] were performed to account for each the different optical properties of each dielectric layer (4-phase: glass, iron thin film, silicon dioxide, chemiluminescent dye) and their respective thicknesses (iron: 15 nm, silicon dioxide: 10 nm, dye: 20 nm).

Emission Measurements

Metallic thin films were placed onto a hemispherical prism that was attached to stationary stage. A fiber optic assembly that can rotate 360 degrees at a fixed distance to the hemispherical prism was fitted around the stage. Fifty microliters of the chemiluminescent solution was placed onto the iron thin films and SPCC (from the back of the iron thin films) and free-space emission intensity at observation angles of 0-360 degrees was collected using a spectrofluorometer (Model No: HD2000+, Ocean Optics, USA), which is connected to the fiber optic assembly. A polarizer was placed in front of the fiber optic to collect s- or p-polarized emission.

Optical Spectroscopy. The absorption spectra of the nanostructured films of varying thicknesses were collected using a Varian Cary 50 UV-Vis spectrophotometer. Fluorescence spectra of the fluorophores were measured with blank glass sandwiches and glass-nanostructured film sandwiches using an Ocean Optics HD2000 fluorometer.

Atomic Force Microscopy (AFM). AFM images were performed on a Molecular Imaging Picoplus Microscope. Samples were imaged at a scan rate of 1 Hz with 512×512 pixel resolution in a tapping mode.

Mie Scattering. Mie scattering calculations for a 100 nm Nickel nanoparticle in water were performed using freeware MieCalc software version 1.5.

FDTD Calculations. The FDTD method was employed here to determine the electric field intensities and distributions at the surface of Nickel nanoparticles in a Total Field Scattered Field (TFSF), recalling that an enhanced e-field is one of the two mechanisms thought to contribute to fluorescence enhancement. TFSF sources are used to divide the computation area or volume into total field (incident plus scattered field) and scattered field only regions.[30,31] The incident p-polarized electric field is defined as a plane wave with a wavevector that is normal to the injection surface. The scattered and total fields were monitored during the simulation such that the total or scattered transmission can be measured. Using Lumerical FDTD Solution software, the simulation region is set to 800×800×800 nm with a mesh accuracy of 6. The overall simulation time was set to 500 ns and calculated over a frequency range from 300-800 nm for silver nanoparticles and 300-800 nm for the nickel nanoparticles.

Figure 2:
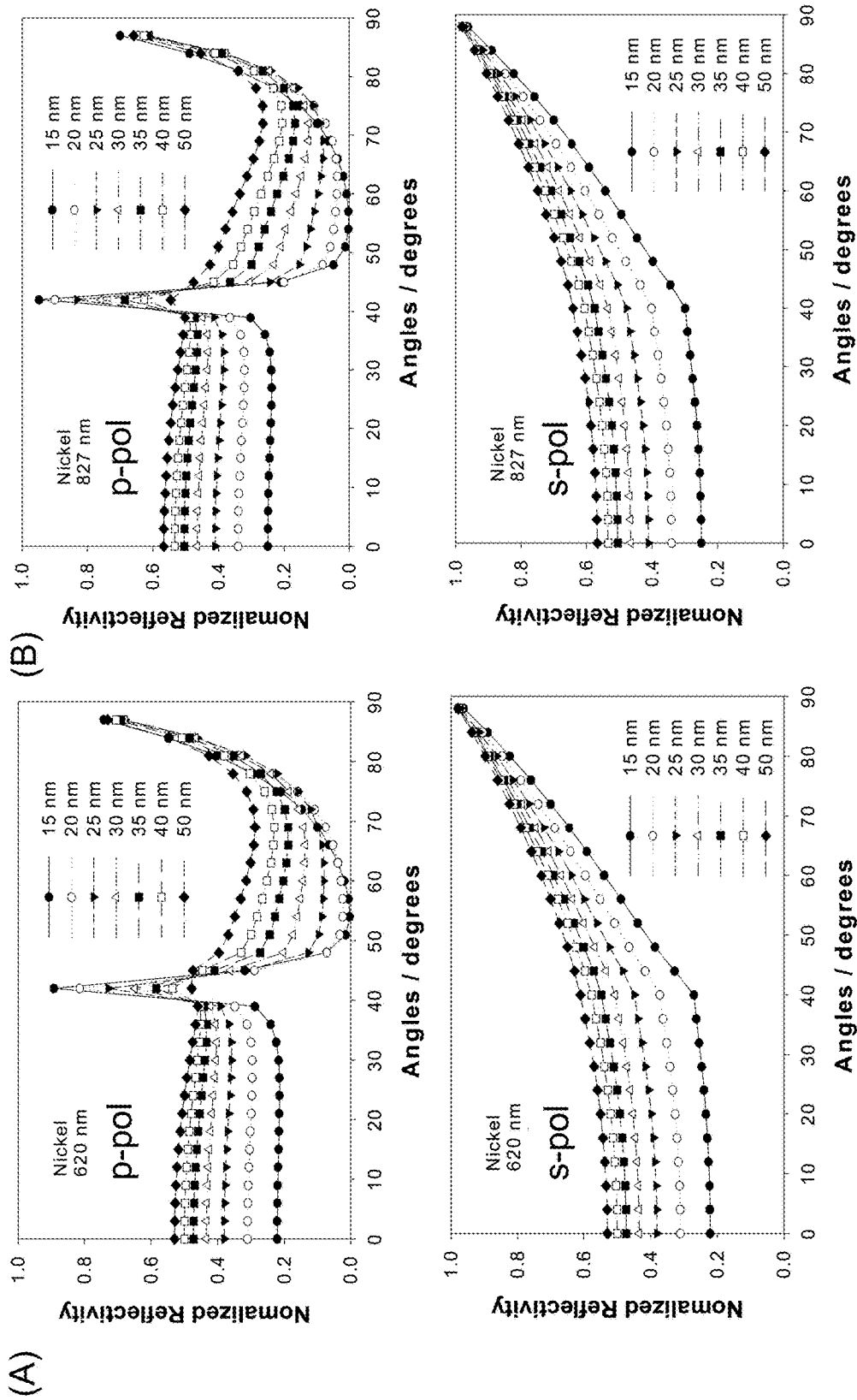
FIG. 2 shows determination of nickel substrate thickness for Surface Plasmon Coupled Fluorescence. Four-phase Fresnel reflectivity curves for p-(top) and s-(bottom) polarized light at (A) 620 nm and (B) 827 nm for nickel substrate thicknesses ranging from 15 nm to 50 nm with a 10 nm $SiO_x$ overlayer.

FIG. 2 shows the results of Fresnel calculations that were employed to predict the interactions of p- and s-polarized light at 620 and 827 nm with nickel thin films with various thicknesses (15-50 nm). The reflectivity values in FIG. 2 were normalized to compare the angle of minimum reflectivity for the nickel thin films of different thicknesses. It is important to note that the reflectivity minimum is indicative of the efficiency of surface plasmon generation in metals.[12] In SPFS, excited states (dipole) can couple/induce to surface plasmons more effectively at the angle of reflectivity minimum, i.e., coupled fluorescence quanta radiates at this angle. In addition, the extent of coupling of luminescence increases as the reflectivity value decreases. Thus, normalized reflectivity values can be semi-qualitatively used to assess the utility of the thickness of thin metal films in SPFS.

Figure 10:
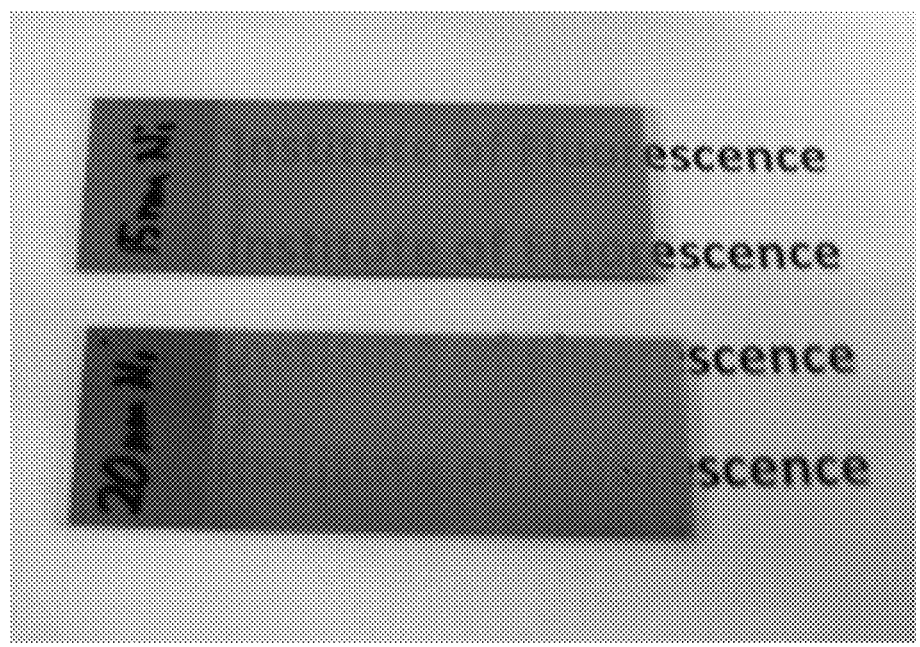
FIG. 10 shows photographs of nickel substrates depicting the semi-transparent nature of the nickel substrates.

FIGS. 2A—Top and 2B—Top show that the normalized reflectivity for incident p-polarized light at 620 and 827 nm is minimal at 52-56 degrees for 15 nm nickel thin films. A closer look at FIGS. 2A—Top and 2B—Top reveals that 20 nm thick nickel films can also be used for SPCF since the normalized intensity and the angle of reflectivity minimum were similar to that of 15 nm nickel films. In addition, the extent of coupling of s-polarized light to surface plasmons is predicted to be the largest for 15 and 20 nm nickel thin films as shown in FIGS. 2A—Bottom and 2B—Bottom. Fresnel calculations also predict that as the thickness of the nickel thin film is increased the s-polarized component of coupled light is decreased. Nevertheless, the extent of coupling of p-polarized light is predicted to be much larger than the extent of coupling of s-polarized light for 15 and 20 nm nickel thin films as compared to 25-50 nm nickel thin films, c.f. FIG. 2. In this regard, the ideal thickness for the nickel thin films for SPFS was concluded to be 15→20 nm. Real-color photographs of nickel thin films (FIG. 10) show the semitransparent nature of these thin films.

Figure 3:
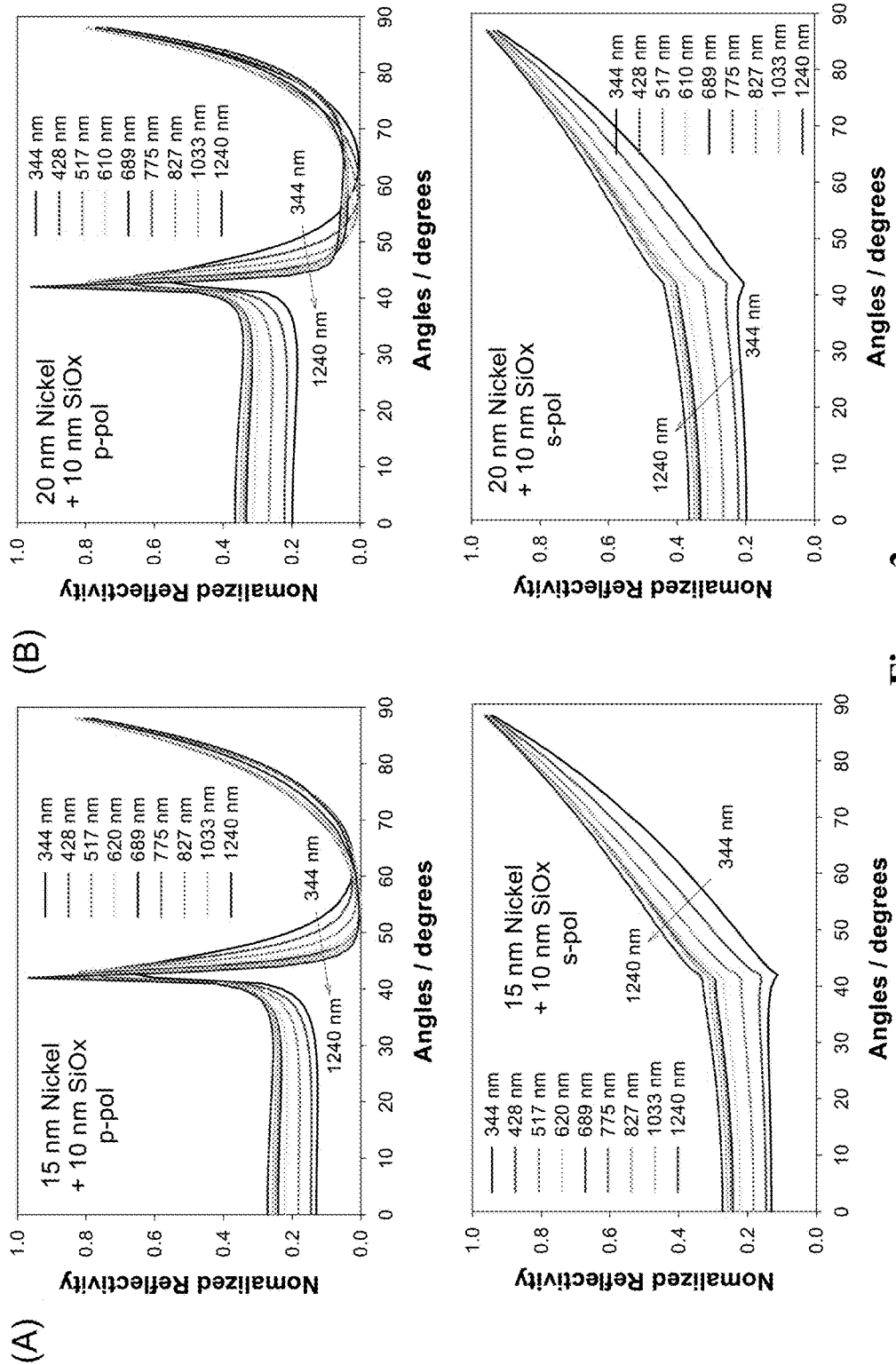
FIG. 3 shows determination of nickel substrate wavelength range for Surface Plasmon Coupled Fluorescence. Four-phase Fresnel reflectivity curves for p-(top) and s-(bottom) polarized light at 344, 428, 517, 620, 689, 775, 827, 1033, and 1240 nm for (A) 15 nm Ni and (B) 20 nm Ni with a 10 nm $SiO_x$ overlayer.

Subsequently, the range of fluorophores that will most efficiently couple to nickel thin films was determined from four-phase Fresnel reflectivity curves that were calculated for a wide range of wavelengths (344-1240 nm) and are shown in FIG. 3. As shown in FIGS. 3A—Top and 3B—Top, Fresnel calculations predicted that p-polarized light in the wavelength range of 428-1240 nm can induce surface plasmons at a fixed range of angles (50-60 degrees and 55-65 degrees for 15 and 20 nm nickel thin films, respectively). It was also found that the angle of reflectivity minimum for 344 nm incident light is shifted to wider angles (60-70 degrees). From these calculations it can be concluded that 15 and 20 nm nickel thin films can be used in SPCF applications over the wavelength range of 344-1240 and 428-1240 nm without the need to change the observation angle, respectively. This is an interesting prediction which has never been reported for metal thin films for SPCF applications to date.[1,7,8,9,10,11] The extent of coupling of s-polarized light to nickel thin films is predicted to decrease as the wavelength of light is increased as shown in FIGS. 3A—Bottom and 3B—Bottom.

It is important to emphasize the possible implications of the results shown in FIG. 3. Most of the commercially available bioassays today employ fluorophores, fluorescent proteins and quantum dots emitting at wavelengths >400 nm. Subsequently, nickel thin films are predicted to be a single assay platform in SPFS, for use in both the ultraviolet and NIR spectral range, a much better choice than other metallic thin films. It is also interesting to place these theoretical predictions in context with the use of other metals for SPCF. In these other reports,[9,10,11] the wavelength dependence of the reflectivity minimum of the metals, allows for the angular separation of different wavelengths, at different angles. Here, nickel thin films can provide for emission at the same angle, but over a broad wavelength range, making them particularly attractive for fixed angle and fixed geometry experimental settings.

Figure 4:
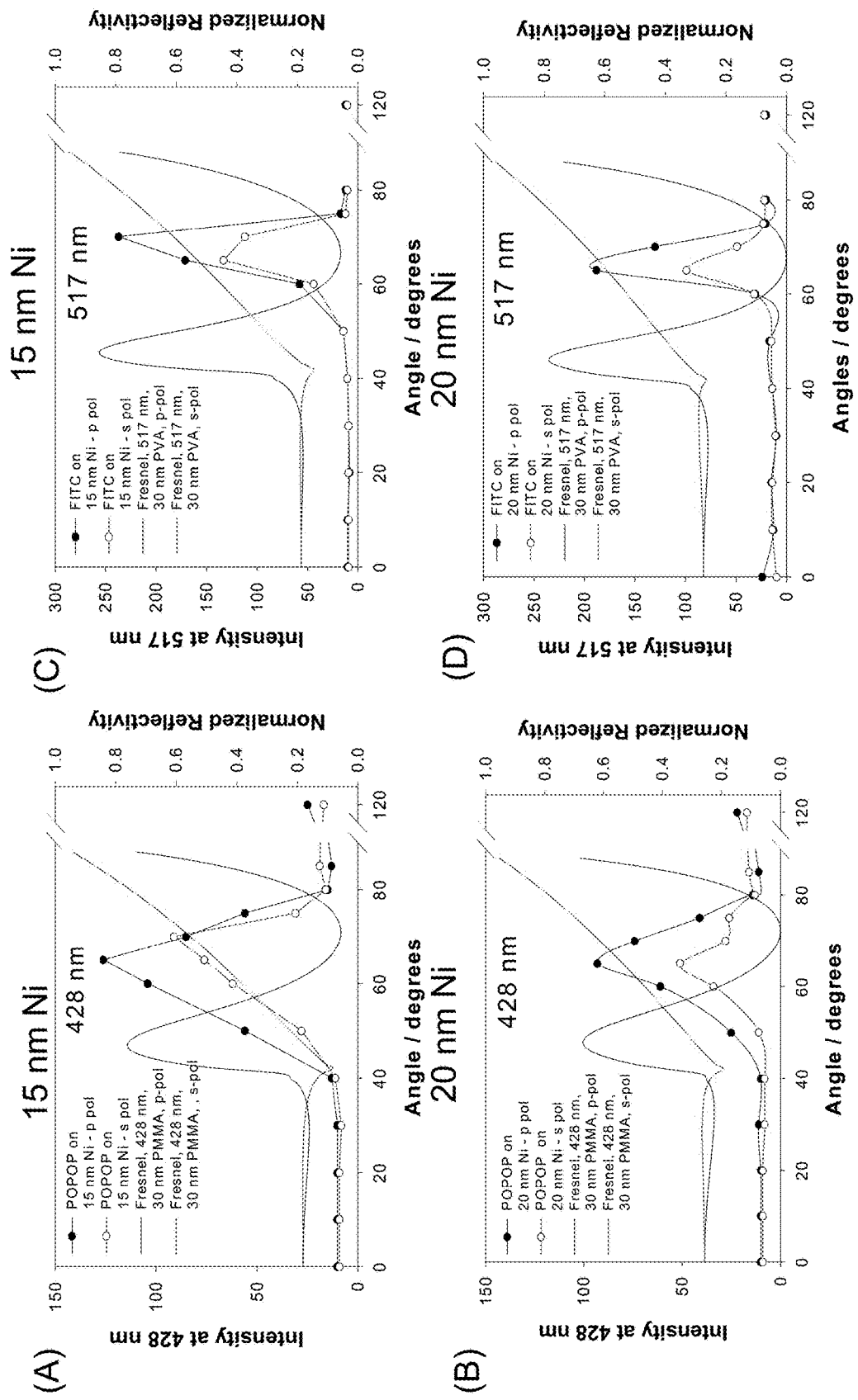
FIG. 4. shows surface Plasmon Coupled Fluorescence on nickel substrates from POPOP and FITC. Five-phase Fresnel reflectivity curves showing p- and s-polarized light for (A) 15 and (B) 20 nm nickel substrates with 10 nm $SiO_x$ and 30 nm PVA overlayers. Experimental p- and s-polarized emission collected at 428 nm from 100 mL solution (POPOP in PMMA and toluene) on nickel substrates with 10 nm $SiO_x$. Five-phase Fresnel reflectivity curves showing p- and s-polarized light for (C) 15 and (D) 20 nm nickel substrates with 10 nm $SiO_x$ and 30 nm PVA overlayers. Experimental p- and s-polarized emission collected at 517 nm from 100 mL solution (FITC in PVA) on nickel substrates with a 10 nm $SiO_x$ overlayer.
Figure 11:
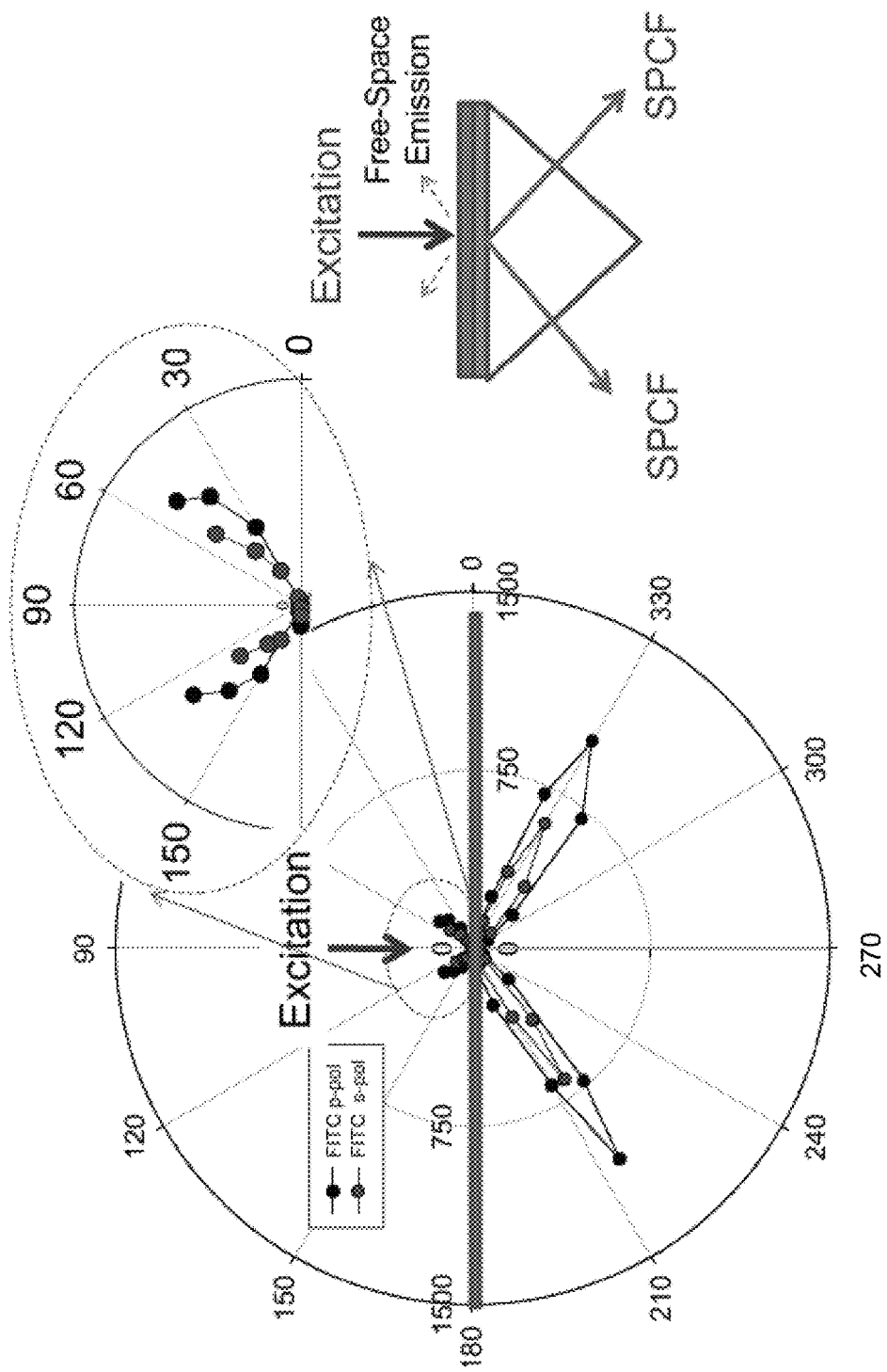
FIG. 11 shows angular distribution of emission from FITC on 20 nm nickel substrate with 10 SiOx overlayer (left). Experimental geometry for nickel SPCF with a reverse Kretschmann configuration.

The experimental confirmation of the theoretical predictions of the Fresnel calculations was undertaken with a series of experiments, where SPCF from five different fluorophores emitting in the 428-814 nm wavelength range was measured and compared with the Fresnel calculations, which additionally account for polymer layer where fluorophores are embedded. Since both 15 and 20 nm thick nickel films were predicted to have utility in SPSF, both of these samples were used. FIG. 4 shows these results for POPOP (FIGS. 4A and 4B) and FITC (FIGS. 4C and 4D). It is important to note that the thickness of the polymer film containing the fluorophores were kept ≈25 nm to avoid waveguide modes that results in emission at multiple observation angles.[9] The maximum SPCF intensity for POPOP appears to occur at 65 degrees on both 15 and 20 nm nickel thin films as predicted by the Fresnel calculations. The SPCF intensity was significantly larger than the free-space emission (120 degrees). In addition, the extent of p-polarized emission was larger than the s-polarized emission (up to 2-fold), unlike the free-space emission where the extent of p- and s-polarized emission were somewhat similar, providing strong experimental evidence for SPCF from nickel thin films. Similar results were also observed from samples containing FITC, FIGS. 4C and 4D, respectively. The maximum SPCF intensity was observed at ≈65 degrees and the ratio of p-polarized to s-polarized emission was ≈2-fold. In addition, the angular distribution of FITC emission on 20 nm nickel thin films was also measured to demonstrate the unique features (emission at a specific angle and preferential emission of p-polarization) SPCF as compared to the traditionally observed isotropic free-space emission (FIG. 11).

The free-space emission was significantly less than the SPCF, which was due the efficient coupled emission from fluorophores placed in close proximity to the metal. It is also important to note that the free-space emission is expected to increase as the thickness of the polymer film containing fluorophores is increased.[7] Based on the results described above, it is concluded that the performance of both 15 and 20 nm nickel thin films for SPCF from POPOP and FITC were similar.

Figure 5:
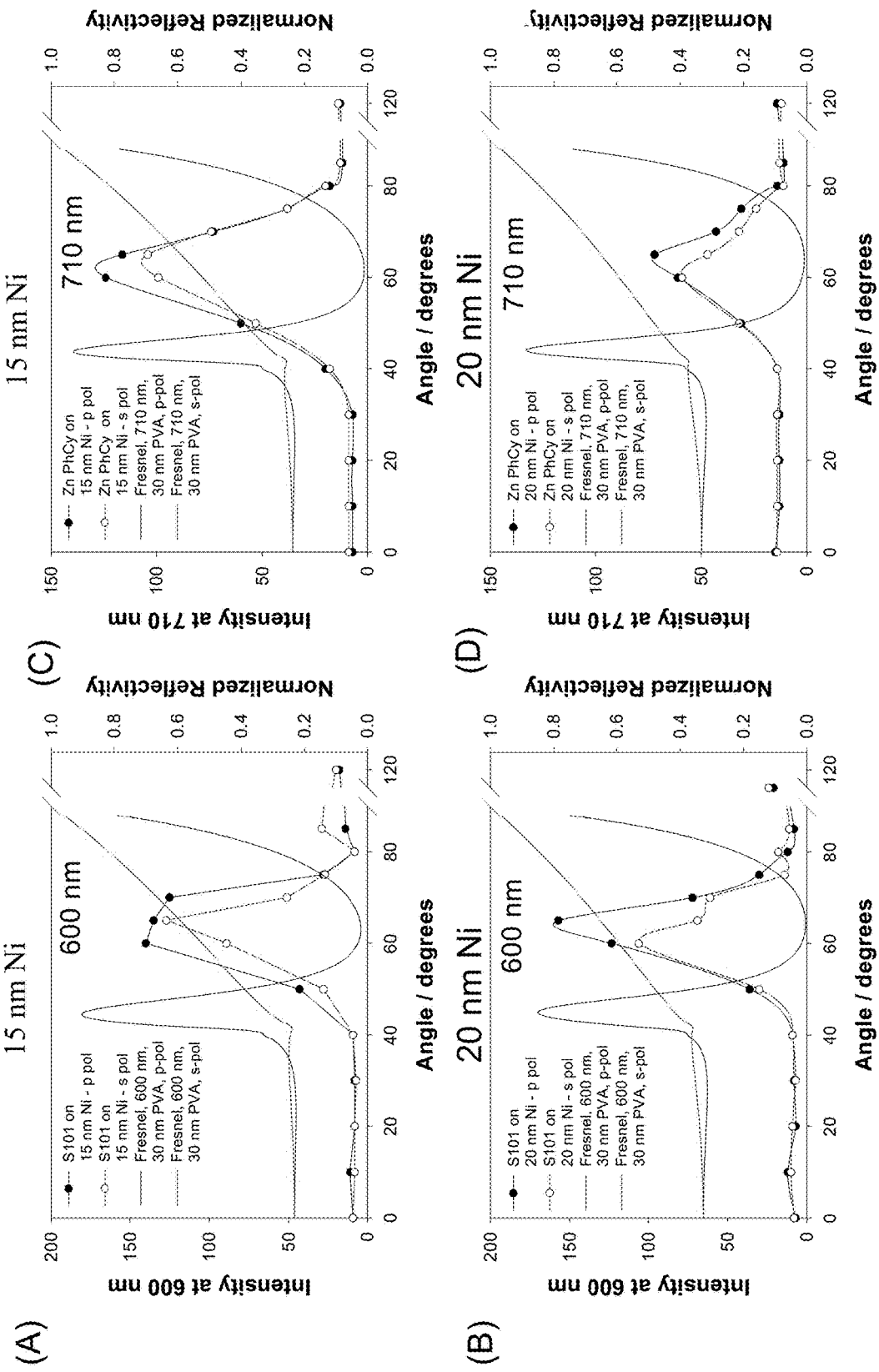
FIG. 5 shows Surface Plasmon Coupled Fluorescence on nickel substrates from S101 and Zn PhCy. Five-phase Fresnel reflectivity curves showing p- and s-polarized light for (A) 15 and (B) 20 nm nickel substrates with 10 nm $SiO_x$ and 30 nm PVA overlayers. Experimental p- and s-polarized emission collected at 600 nm from 100 mL solution (S101 in PVA) on nickel substrates with 10 nm $SiO_x$. Five-phase Fresnel reflectivity curves showing p- and s-polarized light for (C) 15 and (D) 20 nm nickel substrates with 10 nm $SiO_x$ and 30 nm PVA overlayers. Experimental p- and s-polarized emission collected at 710 nm from 100 mL solution (Zn PhCy in toluene and chloroform) on nickel substrates with a 10 nm $SiO_x$ overlayer.
Figure 6:
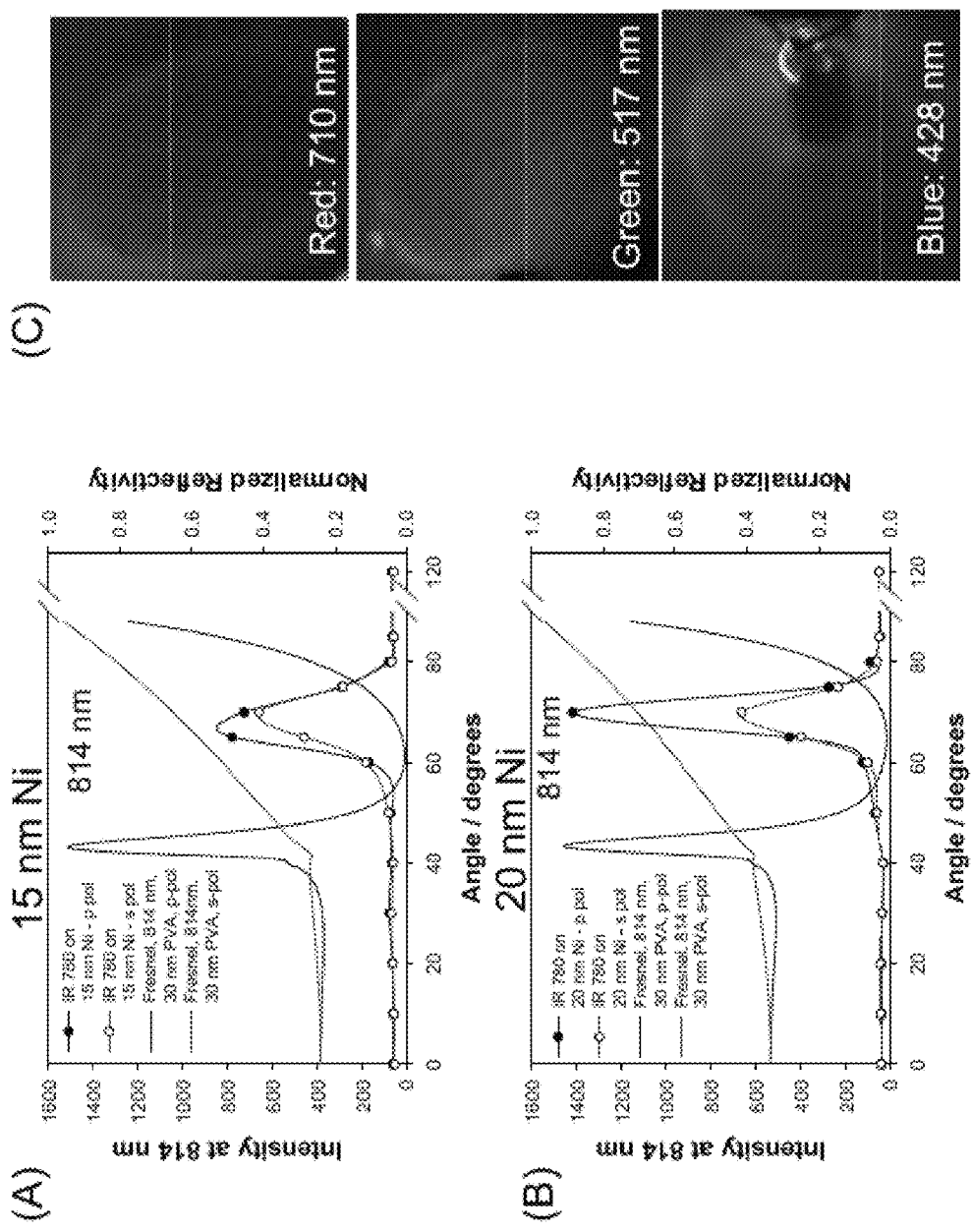
FIG. 6 shows Surface Plasmon Coupled Fluorescence on nickel substrates from IR 780. Five-phase Fresnel reflectivity curves showing p- and s-polarized light for (A) 15 and (B) 20 nm nickel substrates with 10 nm $SiO_x$ and 30 nm PVA overlayers. Experimental p- and s-polarized emission collected at 814 nm from 100 mL solution (IR 780 in PVA) on nickel substrates with 10 nm $SiO_x$ overlayer. (C) Real-color photographs of red (710 nm), green (517 nm) and blue (428 nm) SPCF emission from samples placed on a hemispherical prism. An excitation filter corresponding to the wavelength of excitation was placed in front of the digital camera.

Current fluorescence-based bioassays run in whole blood typically employ fluorophores emitting at wavelengths >600 nm due to the absorption of light by unseparated whole blood for the visible spectral range. In this regard, to assess the potential utility of SPCF from nickel thin films in whole blood bioassays, three more fluorophores emitting at wavelengths 600, 710 and 814 nm were employed and the results of these experiments and Fresnel reflectivity curves calculated at the wavelength of the corresponding fluorophore's emission are shown in FIGS. 5 and 6. FIGS. 5A and 5B show that the maximum SPCF intensity at 600 nm from S101 on both 15 and 20 nm nickel thin films occurs at an observation angle of 65 degrees as predicted by Fresnel calculations. The extent of coupled s- and p-polarized emission was similar from 15 nm nickel thin films (FIG. 5A), and it was larger for p-polarized emission from 20 nm nickel thin films (FIG. 5B). This can be explained by the differences in coupling of light at 65 degrees as predicted by Fresnel calculations: for a 15 nm nickel thin film, Fresnel calculations predict that the normalized s-component of light to be 0.6 while the same value for a 20 nm nickel film is 0.7. That is, more s-polarized light is expected to couple to a 15 nm nickel thin film as compared to a 20 nm nickel thin film. FIGS. 5C and 5D show that the maximum SPCF intensity at 710 nm for Zn PhCy is observed at 65 degrees. The extent of coupled p-polarized emission at 710 nm was slightly larger than s-polarized emission both for 15 and 20 nm nickel thin films. In addition, the SPCF intensity for S101 and Zn PhCy was larger than the free-space emission, which is due to the placement of fluorophores within close proximity of the nickel surface.

FIGS. 6A and 6B show the Fresnel reflectivity curves calculated for s- and p-polarized light at 814 nm and the experimental SPCF intensity values collected at 814 nm from the IR780 dye on 15 and 20 nm nickel thin films. Similar to all the fluorophores studied here, the maximum SPCF intensity from IR780 on both 15 and 20 nm nickel thin films occur at an observation angle of ≈65 degrees, which is indeed a significant benefit of our approach. These observations were consistent with the Fresnel calculations, where the reflectivity minimum was predicted to occur at ≈65 degrees. The extent of coupled p-polarized emission was larger than the s-polarized emission, up to ≈2-fold. The results presented in FIGS. 5 and 6A show that nickel thin films in combination with a long wavelength fluorophore or even potentially quantum dots or fluorescent proteins have potential utility in SPCF-based whole blood assays.

The visual demonstration of SPCF from nickel thin films over a wide range of wavelengths was undertaken by capturing the "ring" of emission with a digital camera. The real-color photographs of the plasmon-coupled emission are shown in FIG. 6C. In this regard, fluorophore-doped nickel thin films were placed onto a hemispherical prism and the fluorophores were excited in the RK configuration (from the sample side at an angle normal to the nickel surface). The SPCF is emitted as a "ring" from the back of the hemispherical prism. Since SPCF intensity is significantly larger than the background (i.e., p/s contrast ratio), the image of the emission "ring" was captured with a digital camera when projected onto a screen. FIG. 6C shows the emission "ring" for red (710 nm), green (517 nm) and blue (428 nm) wavelengths, demonstrating the utility of nickel thin films for SPCF applications for all three primary colors of emission.

Figure 7:
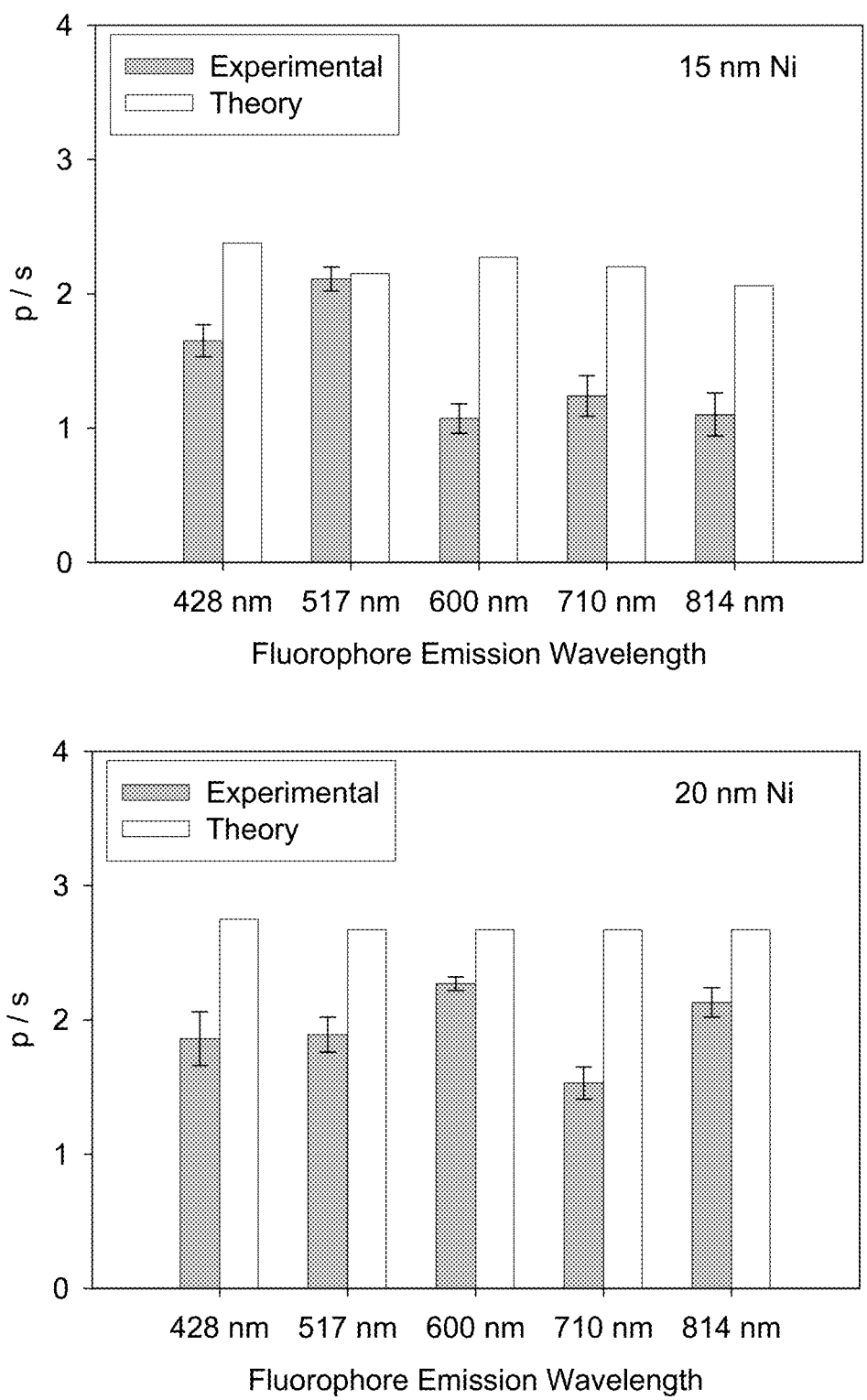
FIG. 7 shows comparison of s- and p-polarized emission. Ratio of p- to s-polarized light for fluorophores ranging from 428 nm to 814 nm on 15 nm and 20 nm nickel substrates.

One of the interesting features of SPCF is the preferential emission of p-polarized light over s-polarized light.[8, 13] In this regard, the theoretical values of the ratio of p- to s-polarized light (p/s) were calculated from normalized Fresnel reflectivity curves and compared with the p/s values extracted from experimental data for all fluorophores used in this study, c.f. FIG. 7. Fresnel calculations predict the p/s values to be ≈2.3 and 2.8 for 15 and 20 nm nickel thin films (428-814 nm). The experimental p/s values appear to be similar, for the most part, to the theoretical p/s values for 20 nm nickel films. On the other hand, the theoretical and experimental p/s values only totally agree for fluorophores with emission wavelengths of 428 and 517 nm and deviate for the fluorophores with emission wavelengths ≥600 nm for 15 nm nickel films. Thus, it is concluded that 20 nm nickel thin films are the best choice for SPCF applications employing fluorophores with emission wavelengths in the visible to NIR spectral regions. It is also interesting to note that 15 nm nickel thin films can be employed for SPCF applications using fluorophores emitting in the visible spectral range.

The utility of nickel thin films in SPCF-based whole blood assays was investigated using the fluorophore Zn PhCy (emission peak at 710 nm) and 20 nm nickel thin films. In this regard, a solution of Zn PhCy, at various concentrations was mixed with whole blood and placed in a sample holder that is attached to nickel thin films. Since whole blood is an optically dense medium, two different sample holders (Diameter×Depth)=9×2 mm and 2×1.5 mm) were employed to investigate the effect of sample volume on the measured SPCF intensity. Total sample volume (including whole blood and a solution of fluorophores) was 30 and 100 uL for 2×1.5 mm and 9×2 mm sample holders, respectively. In addition, two configurations for excitation, KR and RK configurations were also used. In the RK configuration, the fluorophores are excited from the sample side normal to the surface, and the excitation of fluorophores is through the prism placed under the nickel thin films in the KR configuration as shown in FIGS. 1B and 8A—Inset.

Figure 8:
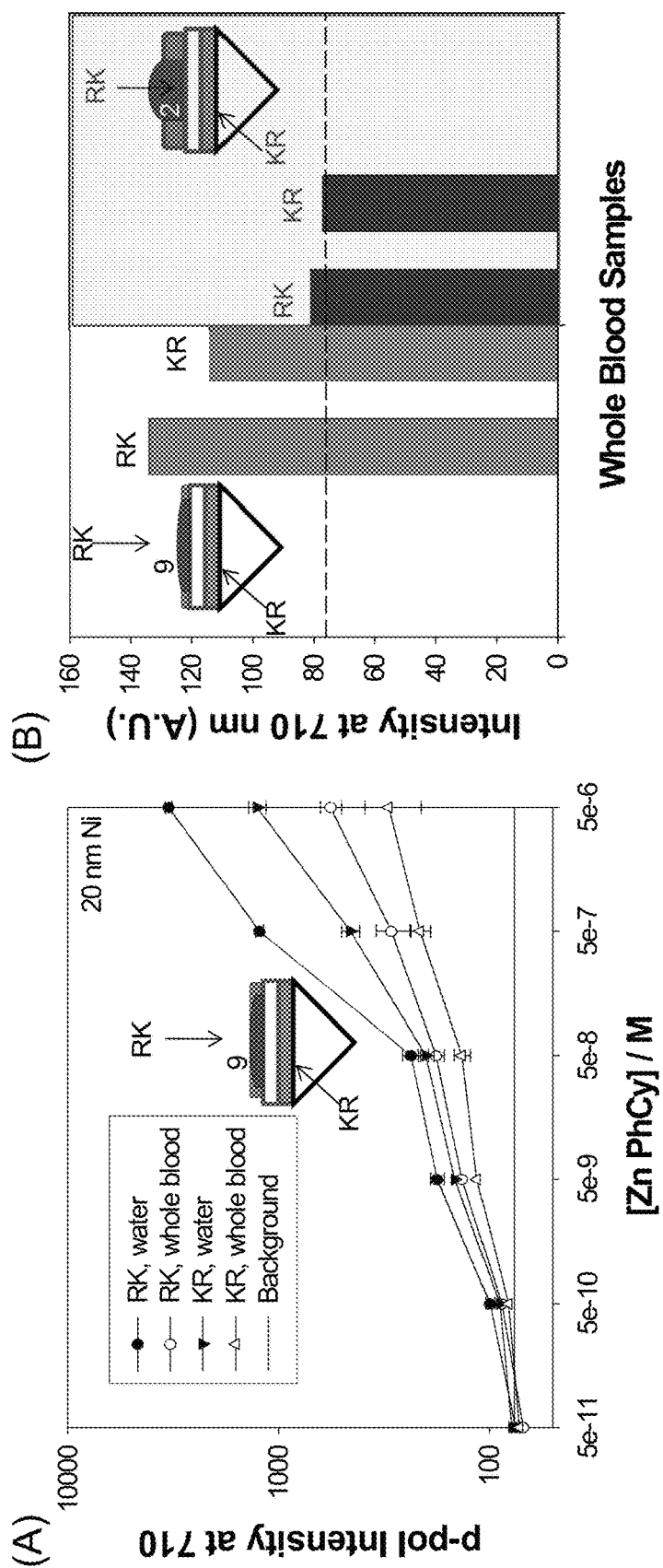
FIG. 8 shows whole blood measurements. (A) Surface Plasmon Coupled Fluorescence measurements in whole blood using Kretschmann (KR) and Reverse Kretschmann (RK) geometries (B) Investigation of the effect of sample (containing whole blood) volume and thickness on the SPCF intensity. The solution of fluorophore was omitted in the sample labeled "background".

FIG. 8A shows the SPCF intensity at 710 nm for the various concentrations of Zn PhCy mixed with whole blood (in the 9×2 mm sample holder) using KR and RK configurations. In additional experiments, whole blood was replaced by water to simulate SPCF-based bioassays run in buffer using both KR and RK configurations. As expected, the SPCF intensity from fluorophores mixed with whole blood was lower than for fluorophores in water. Larger SPCF intensities were measured from all samples in the RK configuration. It is important to note that the depth of the sample holder (9 mm) allowed the mixture of fluorophores in whole blood to spread throughout the sample holder affording for the excitation of fluorophores and thus the detection of SPCF emission.

In addition, the effect of the volume and the shape of sample holder on the SPCF intensity were investigated using another commercially available sample holder (2×1.5 mm, 30 uL sample volume) and compared with the results obtained using the larger sample holder (100 uL). FIG. 8B shows the comparison of SPCF intensity collected from a mixture of 50 nM Zn PhCy mixed with whole blood in both sample holders. The use of the smaller sample holder resulted in SPCF intensities very close to background levels, in comparison to detectable SPCF intensities from the larger sampler holder using both KR and RK configuration. In the smaller sample holder the mixture of fluorophore solution and whole blood prevented the appropriate excitation of fluorophores to yield any detectable signal. Thus, it was concluded that SPCF-based whole blood assays using nickel thin films can be carried out with the appropriate choice of sample volume, i.e, >30 ul whole blood.

Figure 9:
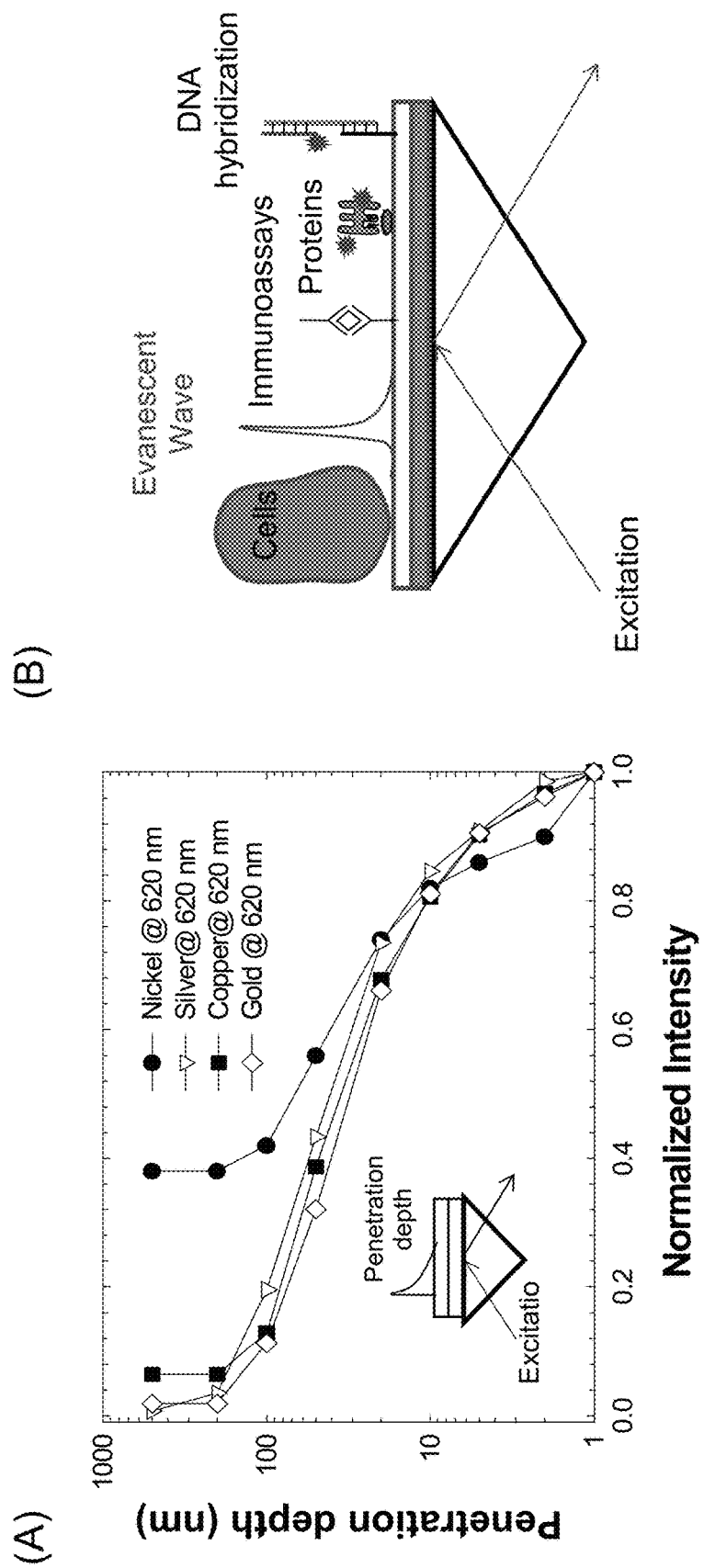
FIG. 9 shows penetration depth calculations. Potential bioassays using surface plasmon coupled fluorescence on nickel substrates. (A) A plot of calculated electric field intensity ($Ez^2$) for penetration depths above several metals using three-phase Fresnel calculations. (B) Opportunities for fluorescence-based detection of bio-species of interest based on SPCF using nickel thin films.

It is well known that light incident upon on a metallic thin film can propagate as an evanescent wave along the metal thin film/dielectric interface (x-direction).[12] In addition, the evanescent wave has an amplitude perpendicular to the metal thin film/dielectric interface and decays exponentially in the z-direction.[12] The penetration depth of this light into the dielectric is in the order of several hundred nanometers and indeed provides for the opportunity for the selective excitation of fluorophores in close-proximity to the metal thin film. FIG. 9A shows the comparison for the calculated penetration depths (using Fresnel calculations) for light at 620 nm above nickel, silver, copper and gold thin films. Fresnel calculations predict that at a distance of 500 nm above nickel thin films, light at 620 nm wavelength can retain 40% of its original intensity as compared to 1% of light that can penetrate to that distance for other metal films used in SPCF. This prediction makes nickel thin films highly attractive in SPCF-based bioassays as compared to gold, silver, zinc and aluminum given that:

- More light can be detected from fluorescent species (greater sample depth) present above nickel thin films, which potentially affords for lower detection limits in bioassays.
- A wide variety of biological assays (immunoassays, DNA hybridization, ELISAs and cell-based assays) can be constructed on nickel thin films,
- Nickel is an inexpensive metal to prepare surfaces for SPCF applications, as compared to gold and silver.
- Fresnel calculations show broad wavelength transmission, suggesting applicability to analytical sensing in the ultraviolet to NIR spectral regions.

Thus, the use of nickel thin films in Surface Plasmon Fluorescence Spectroscopy to generate highly polarized and directional emission is demonstrated. Fresnel calculations predict that light at 344-1240 nm can effectively couple to 10 and 30 nm nickel thin films, and more preferably from 15 to 20, at a fixed 10 degree wide observation angle, located between 60 and 70 degrees from the normal of the surface. SPCF from five different fluorophores with emission wavelengths falling in the range of 428-814 nm were experimentally observed at an angle of ≈65 degrees, in excellent agreement with Fresnel calculations. It was found that the extent of measured p-polarized light was larger than (up to ≈2.8 fold) that of s-polarized light, confirming the observed emission from the back of the nickel film is indeed nickel plasmon-coupled. From the experimental results it was concluded that 20 nm nickel thin films have potential utility in whole blood assays, which was demonstrated with a near-IR fluorescent probe Zn PhCy (emission peak at 710 nm). Fresnel calculations also predict that light can penetrate to a greater distance than other metal thin films, making the nickel thin films an excellent choice of metal to be used in SPCF applications today.

Further in another embodiment, similar to SPCF emission, the present invention relates to using the above-discussed nickel films in a technique called Surface Plasmon Coupled Chemiluminescence. SPCC emission is observed at specific observations angles from the back of the metal thin films. In addition, due to the preferential coupling of p-polarized light to surface plasmons, SPCF and SPCC emission is nearly exclusively p-polarized. Subsequently, SPCF and SPCC emission can be visually seen as a cone, or as a "ring" from the back of the film when a hemispherical prism is employed[7].

Notably, the use of nickel thin films for fixed angle of observation of SPCC is demonstrated herein. Free-space and SPCC emission from blue, green and turquoise chemiluminescent solutions, which have an emission peaks at 492, 509 and 549 nm respectively, were measured using a rotating stage equipped with a fibre optic detection system. The optimum thickness of the nickel thin films for effective coupling of light at these wavelengths was determined to be ~15 nm, using theoretical Fresnel calculations. A 10 nm $SiO_2$ overlayer was also used to protect the nickel surface. Experimental SPCC emission for all the chemiluminescence solutions, which occurred at a fixed angle due to broad wavelength/angle of reflectivity of the metal, was found to be in good agreement with the results of the Fresnel calculations. The observation angles for SPCC emission (492-549 nm) from silver thin films were also calculated and were found to shift as a function of wavelength, in contrast to nickel thin films. To investigate whether nickel thin films have a catalytic effect on the chemiluminescence emission, the decay rates of both free-space and SPCC emission were calculated from time-dependent emission intensity measurements. It was found that the decay rate of the free-space and SPCC emission were very similar, which strongly suggests that nickel thin films have no catalytic effect on chemiluminescence emission. Our findings suggest that 15 nm thick nickel films can be potentially useful for high-sensitivity chemiluminescence-based applications, such as ELISA's, operating at a fixed angle observation.

SPCC and free-space emission from chemiluminescent solutions on nickel thin films were measured according to the following procedure: nickel thin films were placed on a hemispherical prism that is attached to a rotary stage equipped with a fibre optic and fluorometer (Model HD2000, Ocean Optics, Inc., Florida, USA). Freshly mixed (70 ul) chemiluminescent solutions were placed on the nickel thin films and the chemiluminescence emission spectrum and emission intensity at observation angles of 0-360 degrees were recorded. The decay rates of free-space and SPCC emission were recorded at 270 and 60 degrees, respectively (FIG. 12A).

Figure 12:
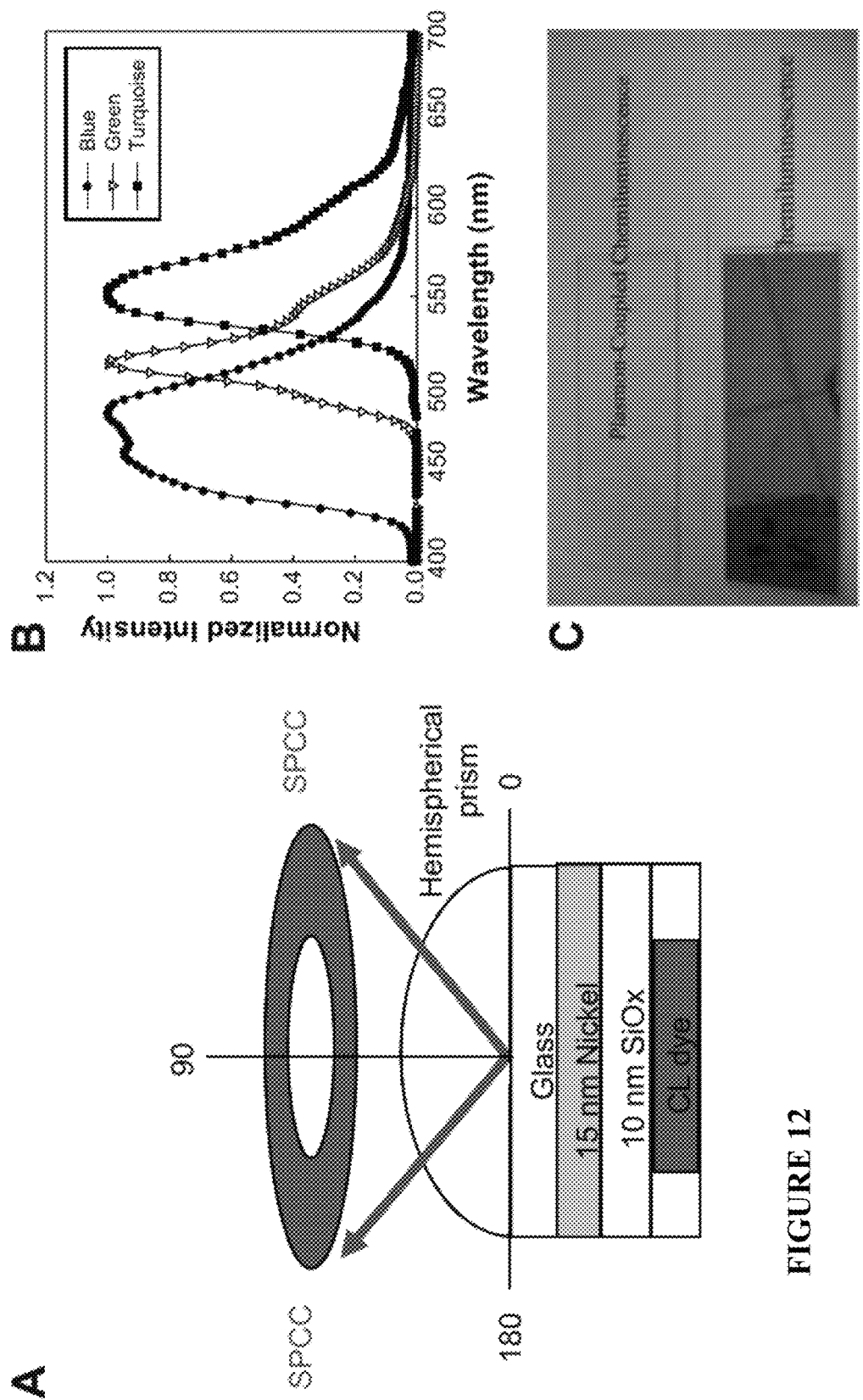
FIG. 12 (A) Experimental configuration of surface plasmon coupled chemiluminescence (SPCC). (B) Normalized spectra of blue, turquoise, and green coupled chemiluminescence through the prism. (C) Photographs of 15 nm nickel thin films compared to a blank glass slide. The text below the slides demonstrates the transmission of the films.

FIG. 12B shows the chemiluminescence emission spectrum for blue, green and turquoise chemiluminescent solutions used in this study. Each chemiluminescent solution has an emission peak at different wavelengths of the spectrum: blue: 492 nm; green: 509 nm and turquoise: 549 nm. FIG. 12C shows the real-color photographs of a nickel thin film deposited onto a glass support and also a blank glass support respectively, demonstrating the semi-transparent nature of the nickel thin films.

FIG. 13A shows the angular-dependent SPCC (0-180 degrees, back of the prism) and free-space (180-360 degrees, sample side) p- and s-polarized emission measured at 492 nm from the blue chemiluminescent solution placed on the nickel thin films. An isotropic free-space emission is observed from the sample side, which is typical for free-space dipoles.[14] In addition, the extent of s- and p-polarized free-space emission was identical, as expected for free-space emission, which is simply the result of the decay of chemically excites states of the randomly oriented chemiluminescent solutions. On the other hand, the SPCC emission is highly p-polarized and highly directional. A maximum SPCC p-polarized emission is detected at observation angles of 60 and 110 degrees. The observation of maximum SPCC p-polarized emission at two angles is due to the symmetry conditions of the dipoles above the metal. Since the same hemispherical prism and nickel thin films are used for all the chemiluminescent solutions in this study, the SPCC emission has a maximum at two observation angles (in the 2D plane) for all the chemiluminescent solutions. In comparison, SPCC s-polarized emission is significantly less ($\sim 1/3^{th}$) that of the p-polarized emission and is observed over a wide range of angles (35-70 and 110-145 degrees, FIG. 13A).

The comparison of the experimental observations with the predictions of the theoretical Fresnel calculations was also made, and is shown in FIG. 13B. In this regard, Fresnel calculations for s- and p-polarized light at 492 nm (corresponds to a maximum emission peak of the blue chemiluminescent solution) were undertaken and plotted side-by-side with the experimental data. In addition, total chemiluminescence emission (measured separately without a polarizer) is measured and all the experimental data is normalized to the largest value of the total emission. Total chemiluminescence emission is the sum of s-, p-polarized SPCC emission and background light. FIG. 13B shows that p-polarized SPCC emission has a maximum value at an observation angle of about 60 degrees, which corresponds to the angle where the reflectivity is a minimum, as predicted by Fresnel calculations. Similarly, total chemiluminescence emission has a maximum value at about 60 degrees, which implies that the measured chemiluminescence emission is surface plasmon coupled and thus is directional.

In addition, the real-color photographs of total free-space and SPCC emission (FIG. 13A) are identical in color (and spectra (data not shown)), which indicates that SPCC emission is indeed from the blue chemiluminescence solution. As described earlier s-polarized SPCC emission is observed over a 30 degree range.

It is important to comment on the utility of Fresnel calculations for SPCC. Fresnel calculations are performed for incident light that enters the prism and induces surface plasmons in metal thin films placed on the prism itself. In this regard, Fresnel calculations are typically employed in the surface plasmon coupled fluorescence (SPCF) technique, where the incident light is used to excite near-field fluorophores. Using Fresnel calculations, the optimal thickness of the nickel thin films was previously determined to be $\approx 15$ nm for SPCF. Since both SPCC (chemically induced electronically excited states) and the SPCF (optically pumped electronically excited states) techniques involve the interactions of excited states of solutions with surface plasmons, the same metal thin films can be employed in both techniques. In this regard, the theoretical Fresnel calculations are a useful predictive tool for applications based on the surface plasmon coupled phenomena.

FIG. 14A shows the angular-dependent SPCC, free-space, and p- and s-polarized emission measured at 509 nm from the green chemiluminescent solution placed on thin nickel films. Similar to SPCC emission from the blue chemiluminescence solution, SPCC emission from the green chemiluminescence solution is highly p-polarized (3-fold larger than s-polarized emission) and highly directional: a maximum SPCC p-polarized emission is detected at observation angles of 70 and 110 degrees in the 2D plane. Free-space emission from green chemiluminescence solution is observed to be isotropic and the extent of s- and p-polarized emission is similar. Fresnel calculations for the interaction of light at 509 nm with 15 nm thick nickel films were undertaken and plotted together with the corresponding experimental data, c.f. FIG. 14B. FIG. 14B shows that largest SPCC emission from the green chemiluminescence solution is observed at an angle of 70 degrees, and is preferentially p-polarized, as predicted by Fresnel calculations. Once again, the extent of coupling of the s-polarized emission was significantly less than the extent of coupling of the p-polarized SPCC emission. The real-color photographs of total free-space and SPCC emission (FIG. 14A) appear to be identical in color and indeed spectral shape (data not shown), which indicates that the SPCC emission originated from the green chemiluminescence solution.

FIG. 15A shows the angular-dependent SPCC, free-space, p- and s-polarized emission measured at 549 nm from the turquoise chemiluminescent solution also placed on the nickel thin films. Similar to SPCC emission from the blue and the green chemiluminescence solutions, SPCC emission from the turquoise chemiluminescence solution is highly p-polarized ($\sim$2.5-fold larger than s-polarized emission) and highly directional. A maximum SPCC p-polarized emission from the turquoise chemiluminescent solution is detected at observation angles of 60 and 115 degrees. Free-space emission from the turquoise chemiluminescent solution was also isotropic and was not preferentially polarized. FIG. 14A shows that the real-color photographs of total free-space and SPCC emission appear to be identical in intensity (and spectra (data not shown)), providing additional evidence that SPCC emission originates from the turquoise chemiluminescence solution. The angular-dependent turquoise chemiluminescence emission was also overlaid with the results of the Fresnel calculations undertaken for 549 nm (corresponding to the emission peak of the turquoise chemiluminescent solution) and 15 nm nickel thin films (FIG. 15B). FIG. 15B shows that there is a good agreement between the angle of minimum reflectivity predicted by Fresnel calculations and the angle where the largest SPCC emission was observed.

Figure 13:
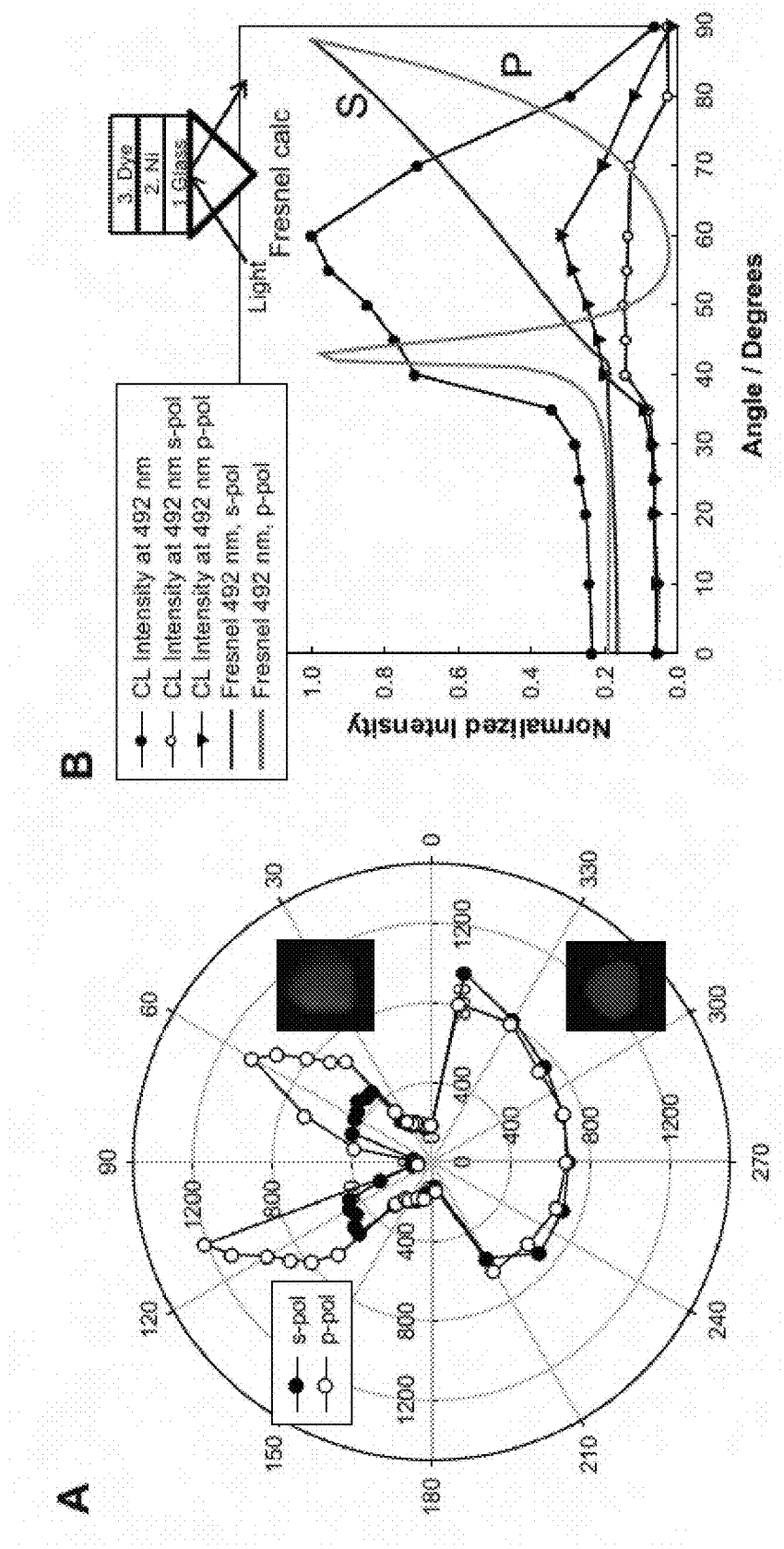
FIG. 13 (A) Polar plot of blue SPCC (0-180 degrees) and the free space chemiluminescence (180-360 degrees) with photographs of coupled (top) and free space (bottom) emissions. (B) Normalized intensity curves of blue chemiluminescence emission, s-polarized emission, and p-polarized emission from 100 ul of chemiluminescent solution on a 15 nm nickel thin films compared with the theoretical reflectivity Fresnel curves.
Figure 14:
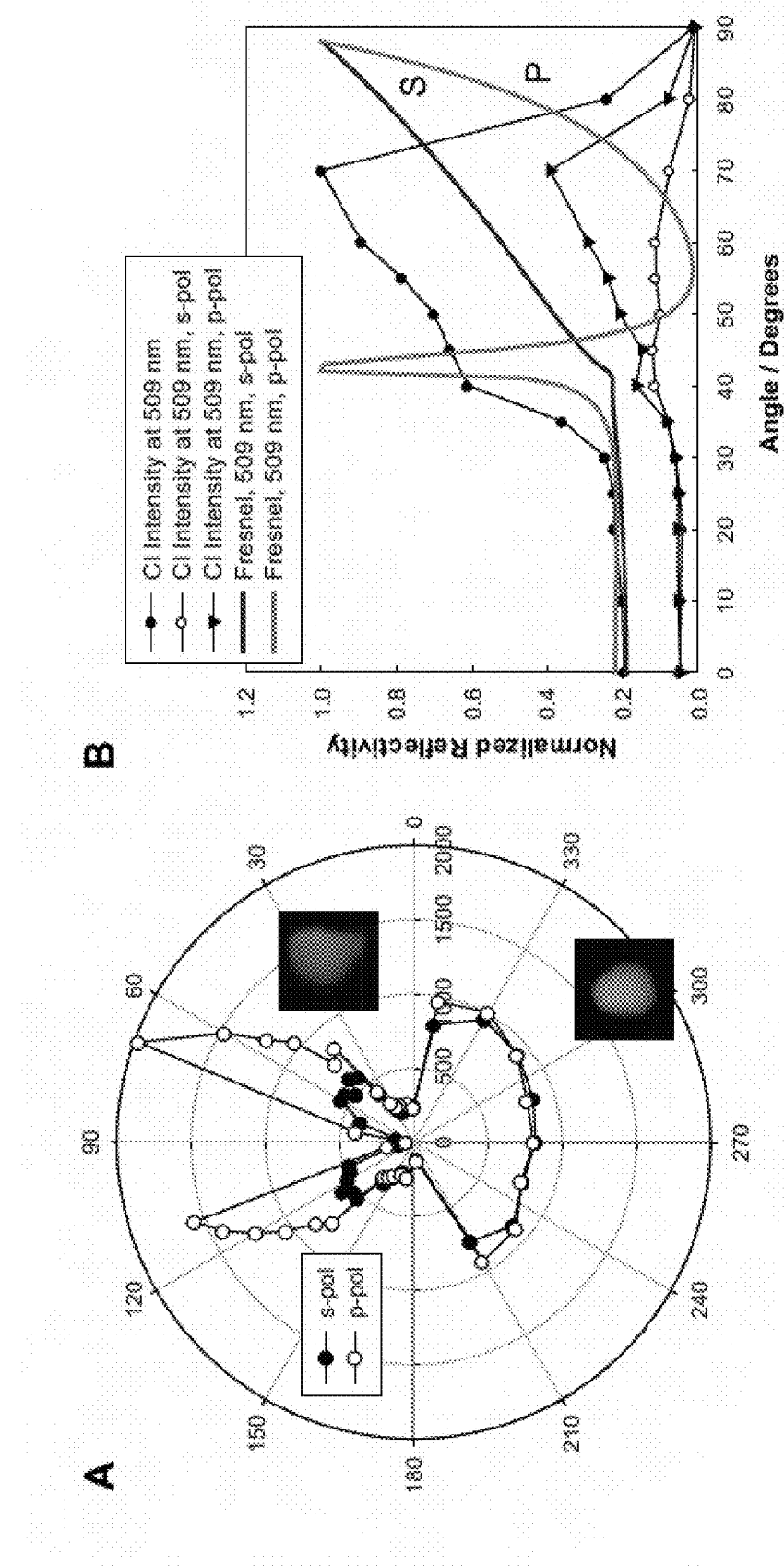
FIG. 14 (A) Polar plot of turquoise SPCC (0-180 degrees) and free space chemiluminescence (180-360 degrees) with photographs of coupled (top) and free space (bottom) emissions. (B) Normalized intensity curves of turquoise chemiluminescence emission, s-polarized emission, and p-polarized emission from 100 ul of dye on a 15 nm nickel thin films as compared with the theoretical Fresnel curves.
Figure 15:
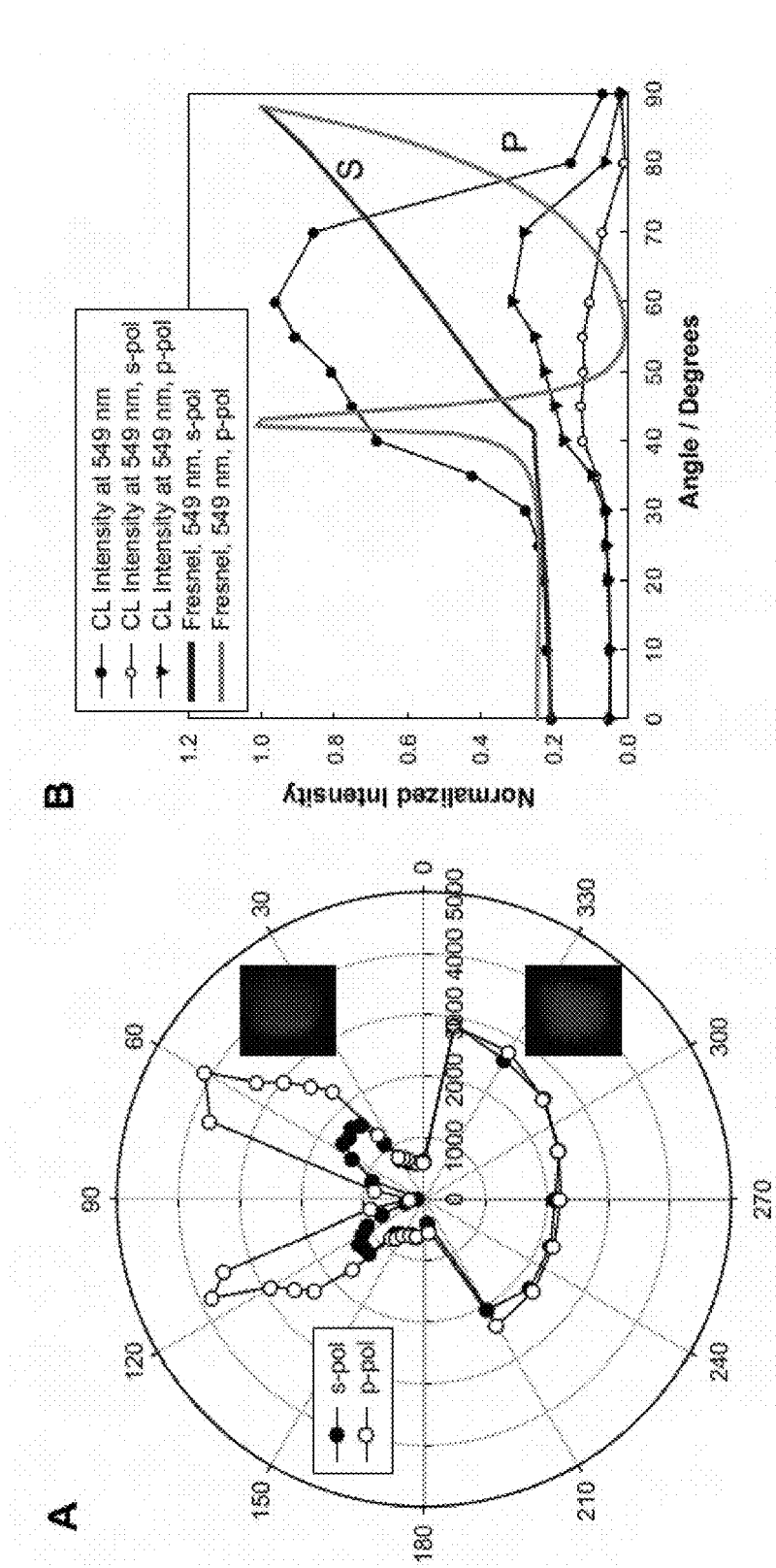
FIG. 15 (A) Polar plot of green SPCC (0-180 degrees) and free space chemiluminescence (180-360 degrees) with photographs of coupled (top) and free space (bottom) emissions. (B) Normalized intensity curves of green chemiluminescence emission, s-polarized emission, and p-polarized emission from 100 ul of dye on a 15 nm nickel thin films as compared with the theoretical Fresnel curves.
Figure 16:
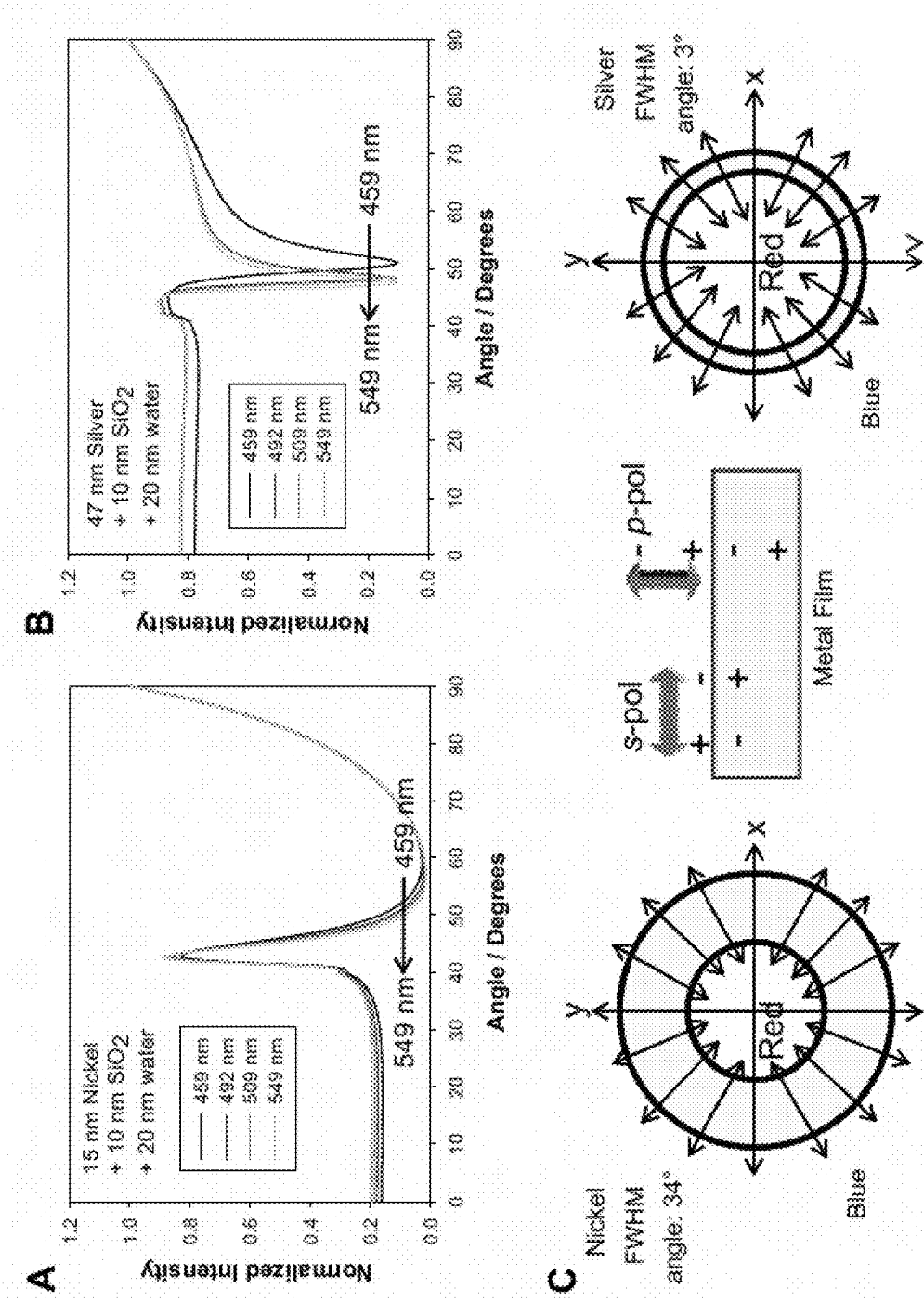
FIG. 16 shows Fresnel reflectivity curves for p-polarized light incident upon (A) 15 nm nickel thin films and (B) 47 nm silver thin films. (C) "Cone" of SPCC from nickel and silver thin films as seen from the z-axis (looking down). Depiction of s- and p-polarization of SPCC is also shown. FWHM-full width half maximum.

It is interesting to further comment on the directional chemiluminescence emission shown in FIGS. 13-15. It is known that fluorophores which are p-oriented with respect to the surface are readily coupled, with s-oriented molecules either not coupling or indeed coupling but, to a much weaker extent.[14] For the chemiluminescence solutions studied here on nickel thin films, this also appears to be the case, FIGS. 13-15, with a very weakly coupled s-polarized emission, thought due to the partially cancelled mirror dipole in the metal film (FIG. 16). In contrast p-oriented chemiluminescence molecules (perpendicular to the film surface) are both coupled efficiently and indeed thought to show a net increase in the surface induced dipole (FIG. 16).

For 15 nm nickel thin films, the reflectivity minimum for the wavelengths studied are both approximately constant and quite broad with respect to collection angle (FIG. 16A). This suggests that for a broad range of wavelengths, a fixed experimental collection geometry could be used, simplifying the collection optics. FIG. 16C shows how p-oriented dipoles for the chemiluminescence dyes are thought to produce the cone of emission from the back of the films, as viewed from the top, i.e. Z-axis. Interestingly, the chemiluminescence emission cone is likely to be broader in angle, as compared to the well studied silver films, which show angle shifts as a function of wavelength (FIG. 16B).

It is also interesting to comment on how the volume/thickness of the coupling dipoles (chemiluminescence solution) can influence the observation angle of SPCC and/or the free space and coupled emission intensity. It is known that dipoles within 10 nm of the surface show a decreased emission[15], where as free-space emission is dominant above 500 nm from the surface. At in-between distances such as for $\lambda/2$ the chemiluminescence emission, the s-oriented dipoles (parallel) will show an increased free-space emission, while the p-oriented molecules (perpendicular) will show decreased free space emission and an increased SPCC. It is this behavior which is well known to cause the oscillatory behavior for dipoles in front of mirrors.[15] For an approximately 1 mm chemiluminescence solution thickness, only a small fraction of the total light was coupled, as evidenced by the large free-space chemiluminescence intensity. For ELISA based assays, where both chemiluminescence substrates and dipoles are located close to surfaces (typically <100 nm), then a significant fraction of the total emission would be expected to couple and be highly polarized and directional.

Figure 17:
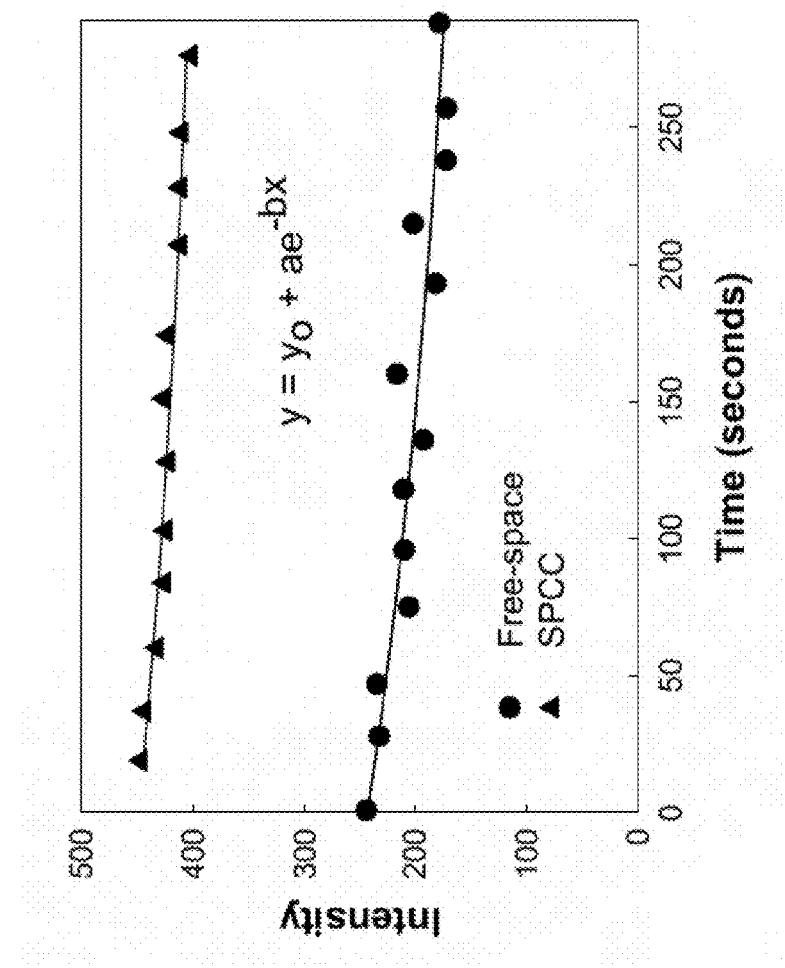
FIG. 17 The free space and SPCC emission decay curves for the green chemiluminescence solution measured at 549 nm.

Finally, metals are known to catalyze chemiluminescence reactions resulting in increased emission and thus faster kinetics of chemical reactions. Subsequently, to investigate whether nickel thin films catalyze reactions that lead to enhanced chemiluminescence emission, the decay of free-space emission (at 270 degrees, FIG. 12A) and SPCC emission (60 degrees, FIG. 12A) intensity over time was measured. FIG. 17 shows the free-space and SPCC emission (at 549 nm) decay curves for the turquoise chemiluminescence solution. The curves for all the chemiluminescence solutions could be fitted well to a single-exponential decay function (1$^{st}$ order kinetics) which closely describes the chemical reactions that lead to chemiluminescence emission. The calculated values of the decay rates are tabulated in Table 1.

TABLE 1

SPCC and free space decay rate4s for blue, turquoise and green chemiluminescence solutions

|  | Coupled Rate k (S$^{-1}$) | Free Space Rate k (S$^{-1}$) |
|---|---|---|
| Blue | 0.0006 | 0.0005 |
| Green | 0.0037 | 0.0034 |
| Turquoise | 0.0018 | 0.0024 |

These values show that free-space emission and SPCC emission rates are very similar, that is, nickel thin films do not have a catalytic effect on these chemiluminescence reactions. This can be partly attributed to the fact that a SiOx overlayer, prevented the direct contact between the chemiluminescent solutions and the nickel thin films.

The first observation of directional surface plasmon coupled chemiluminescence from nickel thin films is demonstrated. Chemiluminescence emission from blue (492 nm), green (509 nm) and turquoise (549 nm) was found to induce surface plasmons in 15 nm thick nickel films, which was subsequently emitted (preferentially p-polarized) through the back of the nickel films at observation angles of 60 an 110 degrees. The extent of coupled p-polarized emission was ≈3-fold larger than the extent of coupled s-polarized emission. Free space emission from all the chemiluminescence solutions was isotropic and did not have preferential polarization, as expected. It was also found that nickel thin films did not have any catalytic effect on the chemical reactions that lead to enhanced chemiluminescence emission. Finally, the use of nickel thin films affords for the potential construction of SPCC-fixed angle geometry devices for a wide-range of chemiluminescence emissions and applications, as compared to the use of other metals (FIG. 16), which have much narrower and sharper angular-dependencies as a function of wavelength.

Notably, it is shown herein that highly directional SPCC emission at a fixed observation angle from iron thin films. Theoretical Fresnel calculations were used to predict the optimum thickness of the iron thin films and the interaction of light at different wavelengths with the iron thin films. Free-space and SPCC emission from blue, green and turquoise chemiluminescent solutions iron films were measured on an experimental setup built in-house. It was found that SPCC emission is highly directional and can be observed at an angle of 60 degrees for all the chemiluminescent solutions. A good agreement between the theoretical Fresnel calculations and experimental data was also seen. It was also found out that iron thin films do not have a catalytic effect on chemiluminescence emission.

Figure 18:
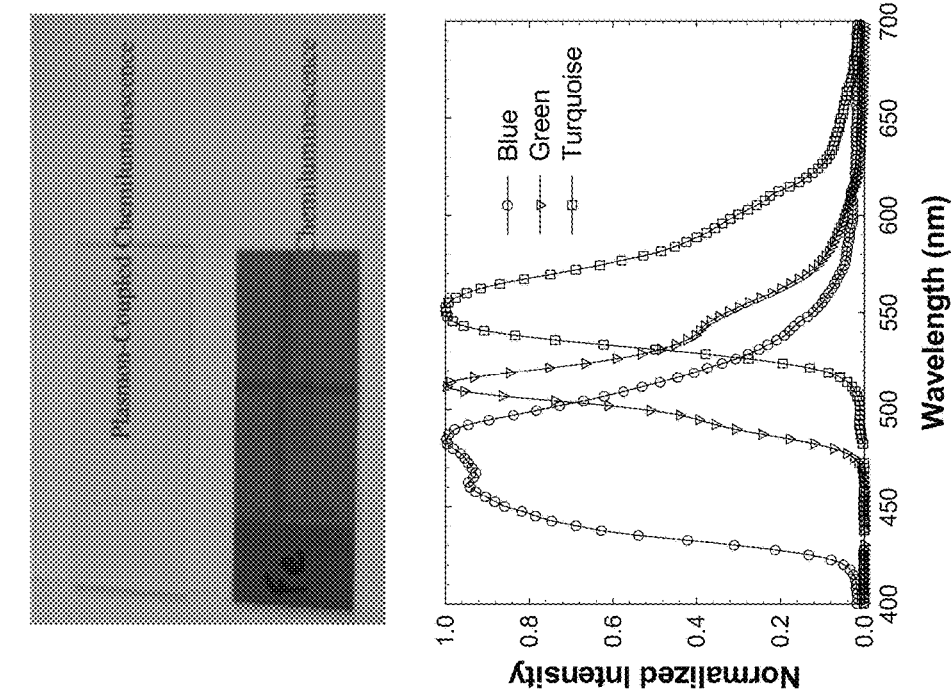
FIG. 18 (A) Schematic depiction of surface plasmon coupled chemiluminescence (SPCC) from iron thin films. (B) Photographs of 15 nm iron thin films compared to a blank glass slide. The text below the slides demonstrates the transmission of the films. (C) Normalized spectra of blue, green and turquoise emission. CL-chemiluminescent.

FIG. 18A shows the schematic depiction of the SPCC phenomenon. In SPCC, p-polarized emission (and s-polarized emission) from chemiluminescent solution induce/couple to surface plasmons in iron thin films, and SPCC is subsequently emitted from the back of the iron thin films at a specific observation angle. The observation angle occurs at the reflectivity minimum of the iron thin films, which can be predicted by theoretical Fresnel calculations. In addition, free-space emission from the sample side (is also measured for the comparison of the directionality and polarization of the SPCC emission with the emission not coupled to surface plasmons. It is also important to note that due to symmetry conditions of the hemispherical prism, SPCC emission is observed at two angles, as indicated by the arrows (FIG. 18A). The real-color photographs of an iron thin film deposited onto a glass support and also a blank glass support are shown in FIG. 18B respectively. Iron thin films appear as semi-transparent films, where the printed letters on a paper are still legible in the background. FIG. 18C shows the chemiluminescence emission spectrum of blue, green and turquoise chemiluminescent dyes, where an emission peak is observed at 492 nm for blue, 509 nm for green and 549 nm for turquoise emission. These emission wavelengths are subsequently used to collect free-space and SPCC emission at various observation angles (0-360 degrees).

Figure 19:
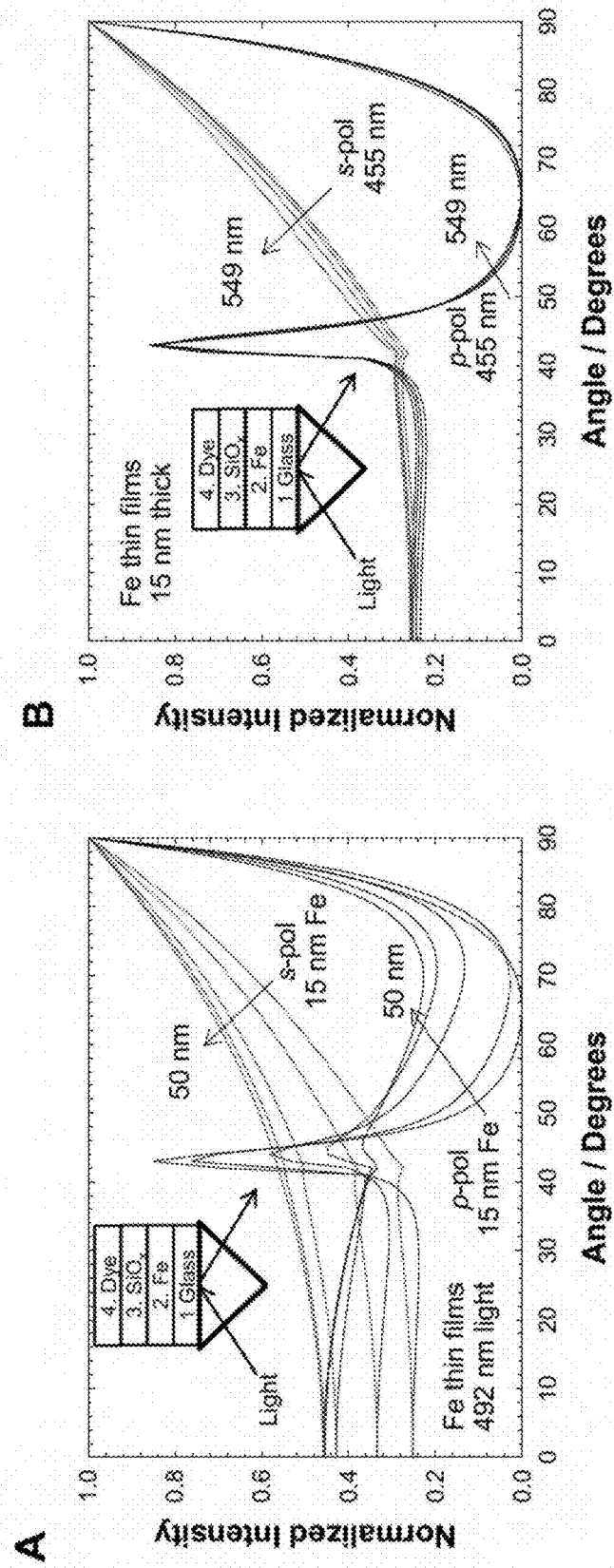
FIG. 19 (A) Four-phase Fresnel reflectivity curves for p- and s-polarized light at 492 nm for iron thin film thicknesses, ranging from 15 nm to 50 nm with a 10 nm SiOx overlayer. (B) Four-phase Fresnel reflectivity curves for p- and s-polarized light at 455, 492, 509 and 549 nm for 15 nm iron thin films with a 10 nm SiOx overlayer.

The theoretical investigation of the optimum thickness of iron thin films that can support surface plasmons was carried out using Fresnel calculations. FIG. 19A shows the Fresnel calculations for light 492 nm incident upon an iron thin film with various thicknesses (15-50 nm). The range of thickness was from about 15-50 nm thick metal thin films to support surface plasmons.[18] The reflectivity curve for p-polarized light at 492 nm has the lowest value of normalized intensity at 65 degrees, which is an indicator of efficient surface plasmon generation, for 15 nm iron thin films. As the thickness of the iron thin films are increased the predicted efficiency of surface plasmon generation is decreased. Subsequently, 15 nm thick iron films are concluded to be the best candidate for SPCC phenomenon. It is also important to note that the extent of coupling of s-polarized light is predicted by Fresnel calculations to be significantly less than the extent of coupling of p-polarized light (FIG. 19A).

Subsequently, the wavelength dependence of reflectivity curves for 15 nm iron thin films is investigated. In this regard, four-phase Fresnel calculations were carried out for light at 455-549 nm and plotted against observation angle (FIG. 19B). FIG. 19B shows that the angle of reflectivity is at a minimum at 65 degrees and the reflectivity curves are identical for light in the 455-549 nm wavelength range. This affords for the SPCC measurements for all chemiluminescent solutions to be made a fixed angle (65 degrees). In addition, Fresnel calculations predict that the extent of coupling of s-polarized light becomes slightly less as the wavelength is increased. It is also important to note that the 455-549 nm wavelength range corresponds to the wavelengths of emission peaks for the chemiluminescent solutions (FIG. 16C).

Again, it is important to discuss the relevance and usefulness of Fresnel calculations in SPCC. Fresnel calculations are originally derived for the prediction of interactions of light with surface plasmons in metals, which is typically used in Surface Plasmon Resonance technique. It is also known that surface plasmon modes in metal thin films can be generated by excited states of the fluorescent species in close proximity, i.e, in the near-field,[14] and thus Fresnel calculations were used in another technique, called Surface Plasmon Fluorescence Spectroscopy (SPFS). It is important to note that in SPFS an external light source is required to excite fluorescent species (optically pumped electronically excited states). Subsequently, the energy released by the decay of the excited states (as fluorescence emission) induces and couples to surface plasmons within several hundred nanometers. The coupled emission is then emitted from the back of the metal thin films at a specific angle, where the reflectivity of light is at a minimum. In a similar fashion, the coupling of chemiluminescence emission (chemically induced electronically excited states) to surface plasmons occurs, resulting in the emission of SPCC from the back of the thin films. Thus, one can use the theoretical Fresnel calculations as a predictive tool for applications based on the surface plasmon coupled phenomena.

Figure 20:
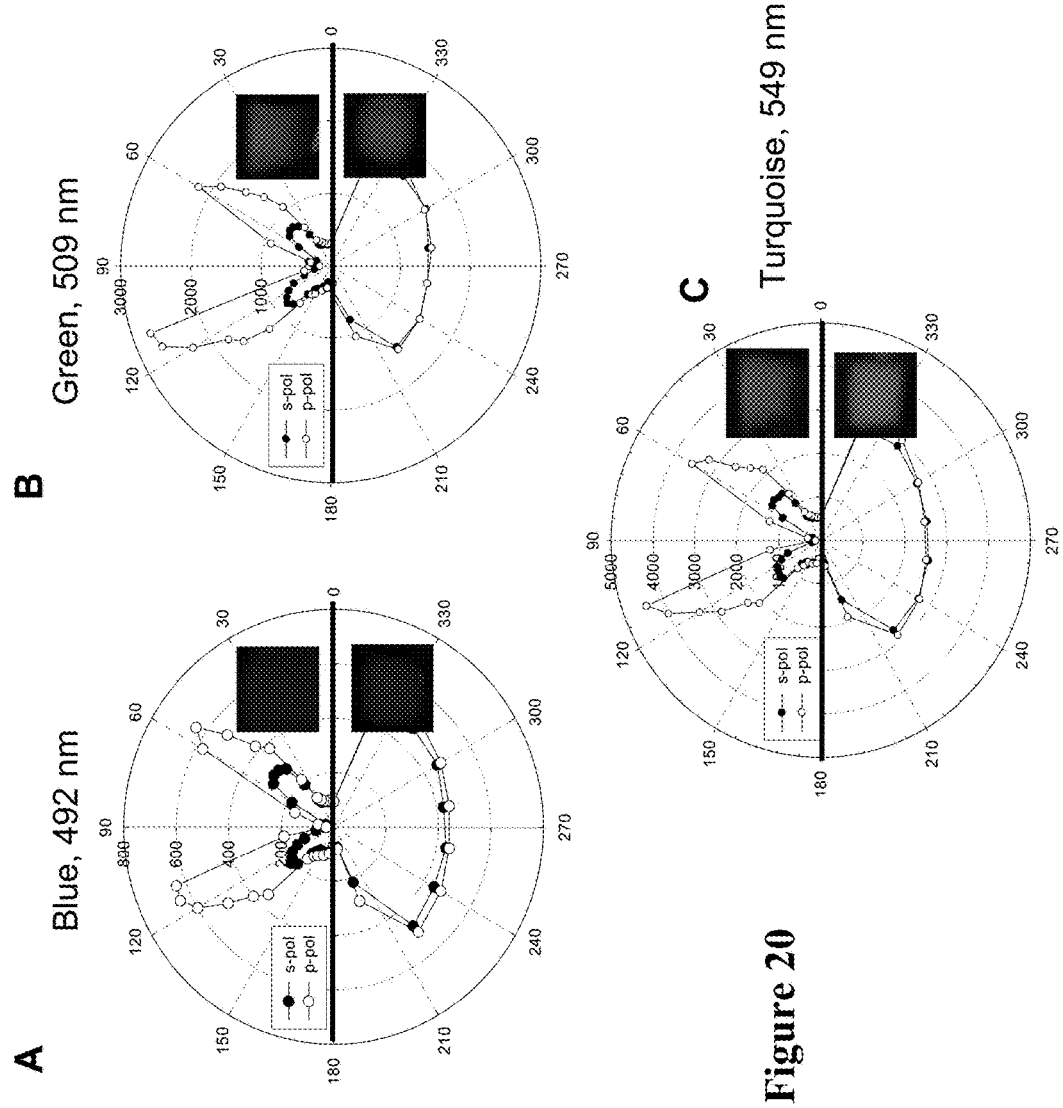
FIG. 20 Polar plot SPCC (0-180 degrees) and free space chemiluminescence (180-360 degrees) with photographs of coupled (top) and free space (bottom) emissions for (A) blue at 492 nm (B) green at 509 nm and (C) turquoise at 549 nm. Experimental geometry is also shown.

FIG. 20 shows the angular-dependent SPCC (0-180 degrees, back of the hemispherical prism) and free-space (180-360 degrees, sample side) p- and s-polarized emission from the blue (at 492 nm, FIG. 20A), green (at 509 nm, FIG. 20B) and turquoise (549 nm, FIG. 20C) chemiluminescent solution. A highly p-polarized and highly directional SPCC emission is observed for all chemiluminescent solutions. P-polarized SPCC emission was at a maximum at observation angles of ≈60 and 110 degrees. The observation of maximum SPCC p-polarized emission at two angles can be explained by the symmetry conditions of the dipoles above the iron thin films.[6,7] Since the same hemispherical prism and iron thin films are used for all the chemiluminescent solutions (separate measurements) in this study, the SPCC emission has a maximum at two observation angles (in the 2D plane) for all the chemiluminescent solutions. In comparison, SPCC s-polarized emission is significantly less (≈½-¼$^{th}$) that of the p-polarized emission, as predicted by the Fresnel calculations. On the other hand, free-space emission from the sample side was isotropic, which is typical for free-space dipoles.[6,7] In addition, the extent of s- and p-polarized free-space emission was identical, which is due to the decay of chemically excites states of the randomly oriented chemiluminescent solutions. The real-color photographs of free-space and SPCC emission for all three chemiluminescent solutions are identical in color (and spectra (data not shown)), which indicates that SPCC emission is indeed from the chemiluminescence solution.

Figure 21:
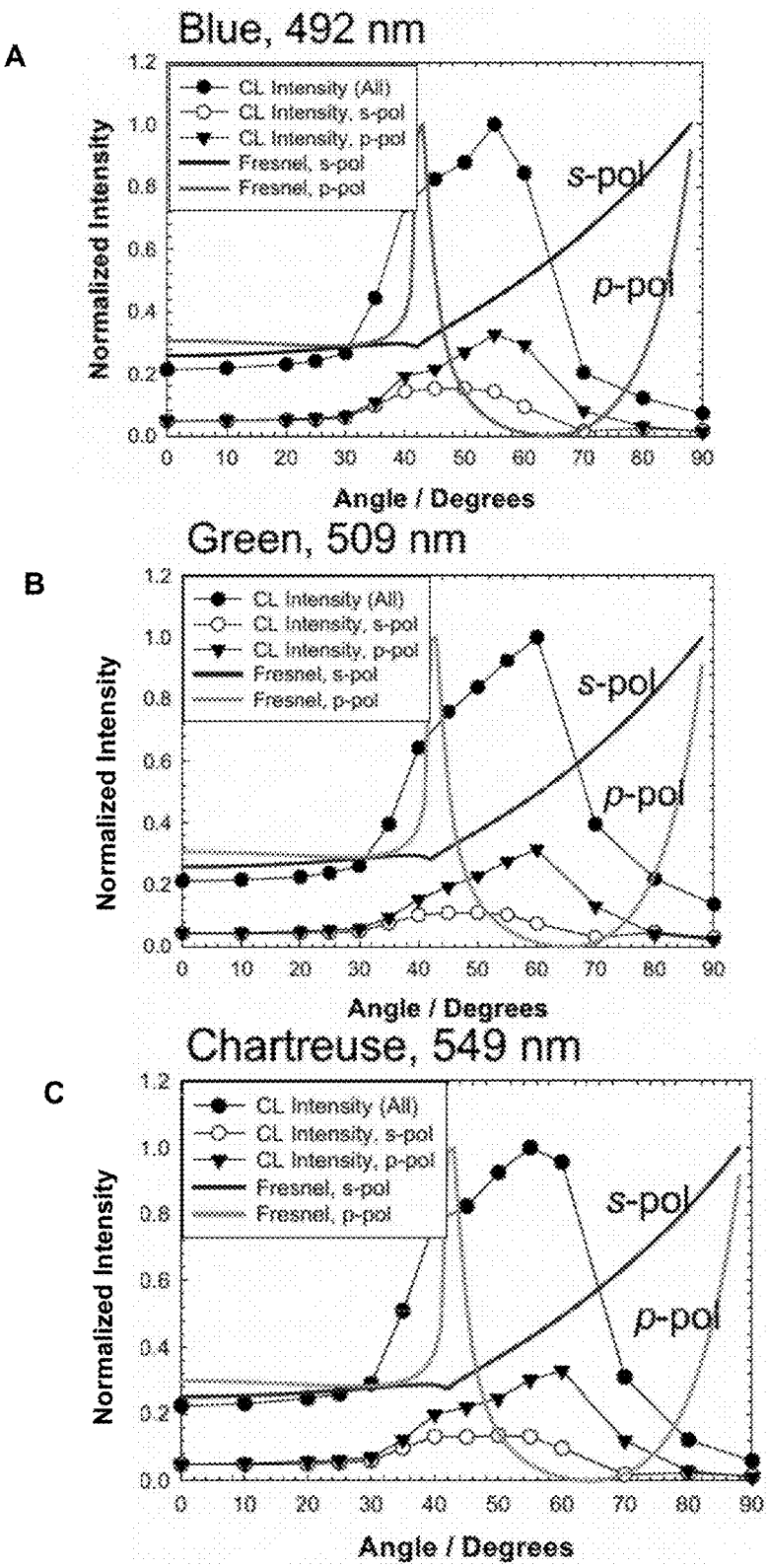
FIG. 21 Normalized intensity curves of chemiluminescence emission, s-polarized emission, and p-polarized emission from 100 μL of dye on a 15 nm iron thin films compared with the theoretical Fresnel curves for (A) blue at 492 nm (B) green at 509 nm and (C) turquoise at 549 nm.

Subsequently, the comparison of the experimental observations for all the chemiluminescent solutions with the predictions of the theoretical Fresnel calculations was made, which are shown in FIG. 21. The side-by-side comparison was made by plotting the normalized reflectivity curves for s- and p-polarized light at 492, 509 and 549 nm (in separate graphs) with the normalized SPCC emission intensity (s- and p-polarized and emission collected without polarizer (all)). FIG. 21 shows that p-polarized SPCC emission has a maximum value at an observation angle of 60 degrees, which corresponds to the angle where the reflectivity is a minimum, as predicted by Fresnel calculations. Similarly, total chemiluminescence emission has a maximum value at 60 degrees, which implies that the measured chemiluminescence emission is coupled to surface plasmon and is directional. Fresnel calculations show that for s-polarized light for light at 492, 509 and 549 nm the extent of coupling is predicted to be larger at observation angles 0-50 degrees, and is predicted to get smaller at observations angles 50-90 degrees, c.f FIG. 21. FIG. 21 also shows that the extent of coupling of the measured s-polarized emission is more at observation angles of 40-60 degrees for all chemiluminescent solutions, and is significantly less than that for p-polarized emission at 60 degrees.

Figure 22:
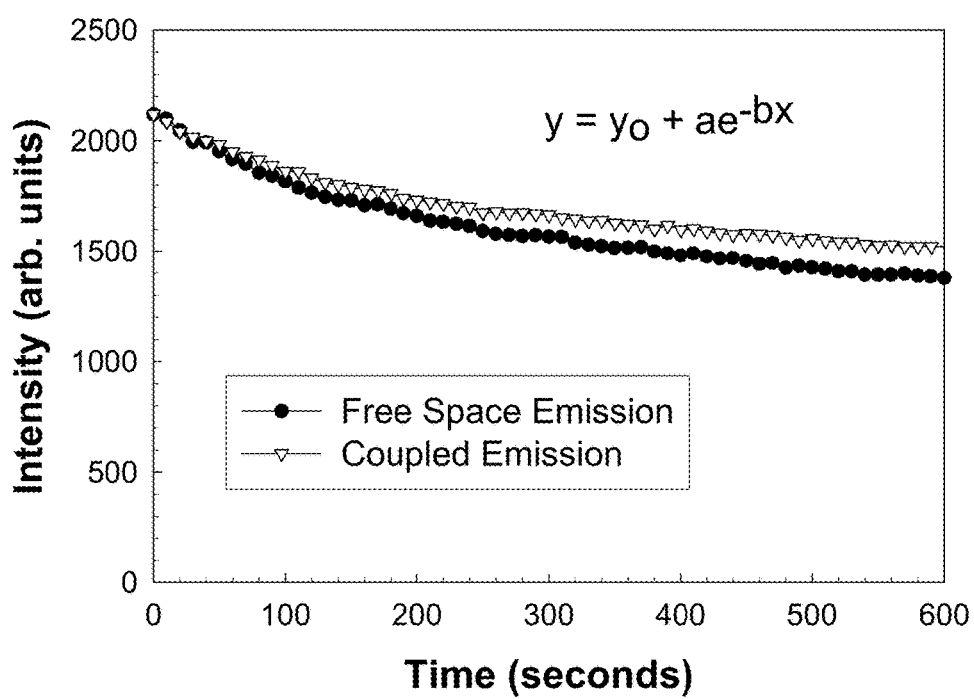
FIG. 22 shows the free space and coupled emission decay curves for turquoise chemiluminescence measured at 549 nm.
Figure 23:
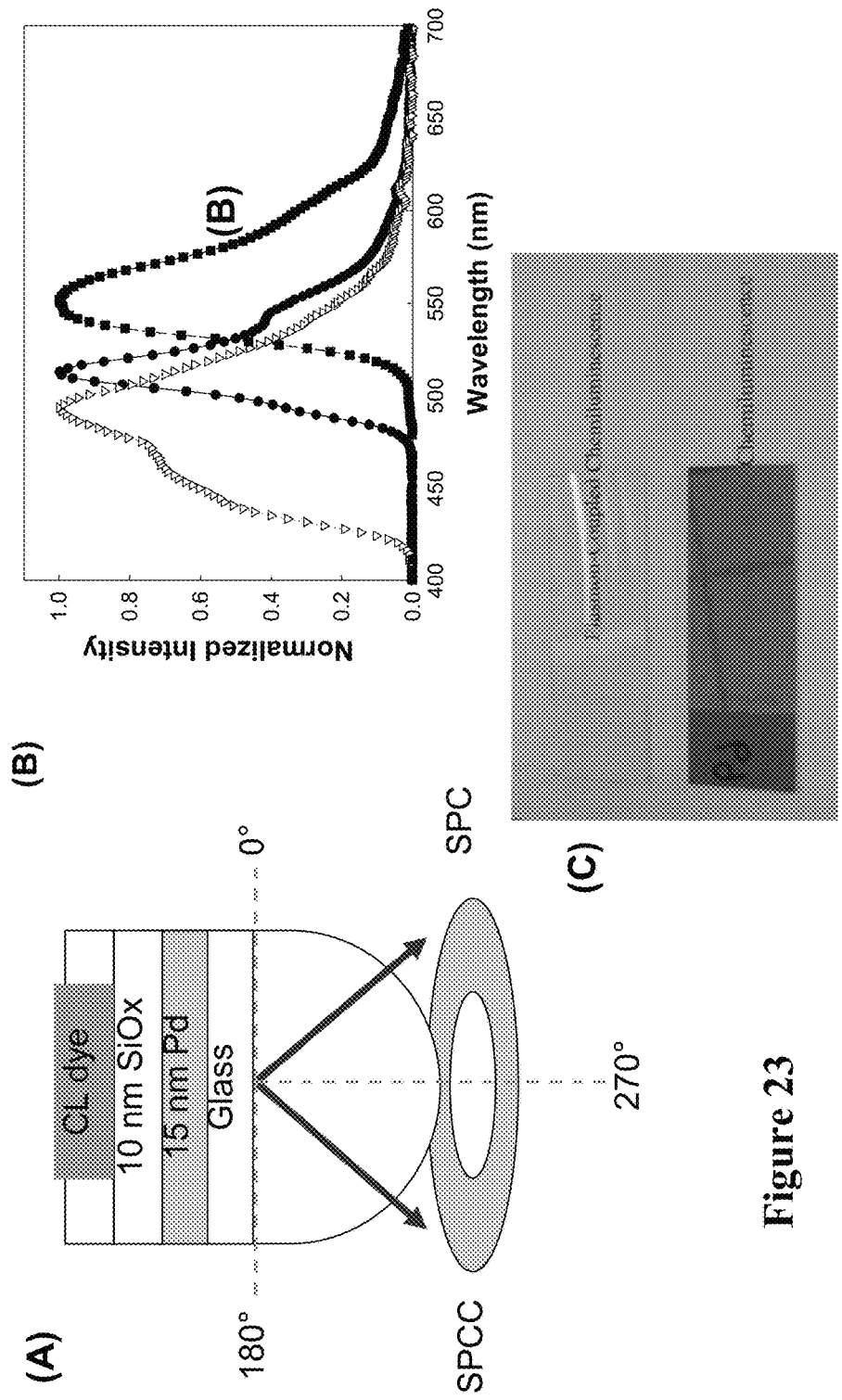
FIG. 23 (A) shows a diagram of surface plasmon coupled chemiluminescence (SPCC) setup (B) normalized spectra of turquoise, green, and blue coupled emission (C) transmission photograph of a 15 nm Palladium slide compared to a saline slide.

It is well-known that chemiluminescence reactions can be catalyzed with ionic form of several metals (e.g. copper) that results in chemiluminescence emission. In this regard, for the sake completeness, it is important to investigate a possible catalytic effect of iron thin films on the chemiluminescence emission. It was thought that if the iron thin films have indeed had a catalytic effect on the chemiluminescence emission, the decay of the free-space and SPCC emission would be different. FIG. 22 shows the SPCC and free space emission at 549 nm decay curves for turquoise chemiluminescence measured at 60 and 270 degrees, respectively. The decay curves for other chemiluminescent solutions were also measured (data now shown). The curves for all the chemiluminescence solutions were fitted to a single-exponential decay function, which closely describes the chemical reactions that lead to chemiluminescence emission. The calculated values of the decay rates are shown in Table 2.

TABLE 2

SPCC and free space decay rates for blue, turquoise, and green chemiluminescence solutions.

|  | Coupled Rate k (sec−1) | Free Space Rate k (sec−1) |
|---|---|---|
| Blue | 0.0031 | 0.0025 |
| Green | 0.0045 | 0.0043 |
| Turquoise | 0.0022 | 0.0022 |

These values show that the SPCC and free-space emission rates are very similar. Subsequently, one can conclude that iron thin films (in the configuration used in this study) do not have a catalytic effect on these chemiluminescence reactions. It is also important to note that a 10 nm thick SiOx overlayer was present on top of iron thin films, which prevented the direct contact between the chemiluminescent solutions and the iron thin films.

Surface Plasmon Coupled Chemiluminescence (SPCC) from iron thin films showed that the chemiluminescence emission coupled to iron thin films (SPCC) emitted at an observation angle of ≈60 degrees from the back of the film. SPCC emission was also predominantly p-polarized. Free-space emission showed no preferential polarization and angular dependence as expected. The comparison of the experimental results and the theoretical Fresnel calculations revealed that both were in good agreement. The investigation of the decay of free-space and SPCC emission from iron thin films revealed that there is no catalytic effect on chemiluminescence emission by iron thin films. Finally, iron thin films affords for the opportunity to make SPCC measurements for a wide range of wavelength at a fixed angle, negating the need to make adjustment to the detection optics.

Figure 24:
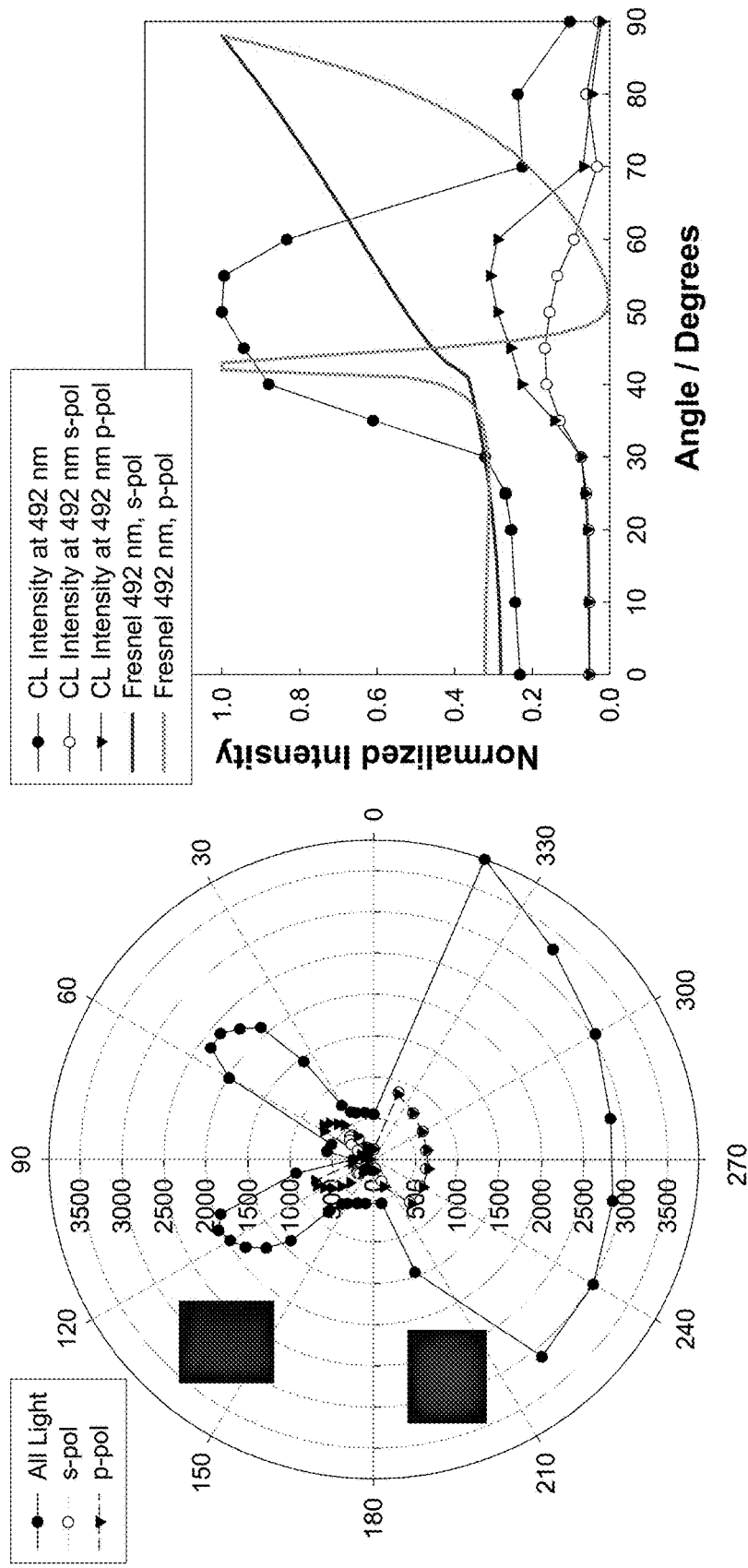
FIG. 24 (A) shows the polar plot of blue SPCC (0-180 degrees) and free space chemiluminescence (180-360 degrees) with photographs of coupled (top) and free space (bottom) emissions (B) normalized intensity curves of blue chemiluminescence emission, s-polarized emission, and p-polarized emission from 100 µL of dye on a 15 nm Pd slide compared with the theoretical Fresnel curves.
Figure 25:
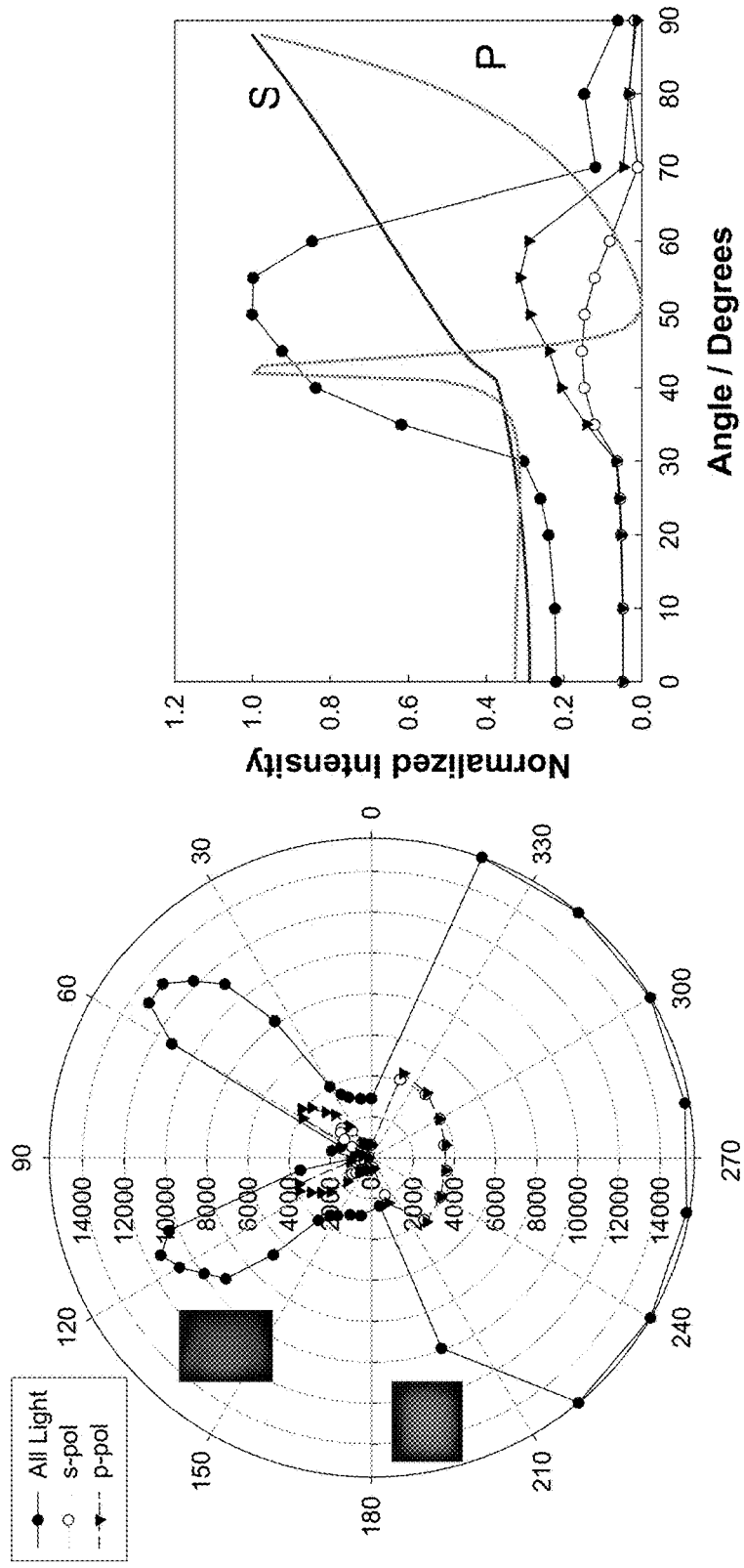
FIG. 25 (A) shows the polar plot of turquoise SPCC (0-180 degrees) and free space chemiluminescence (180-360 degrees) with photographs of coupled (top) and free space (bottom) emissions (B) normalized intensity curves of turquoise chemiluminescence emission, s-polarized emission, and p-polarized emission from 100 µL of dye on a 15 nm Pd slide compared with the theoretical Fresnel curves.
Figure 26:
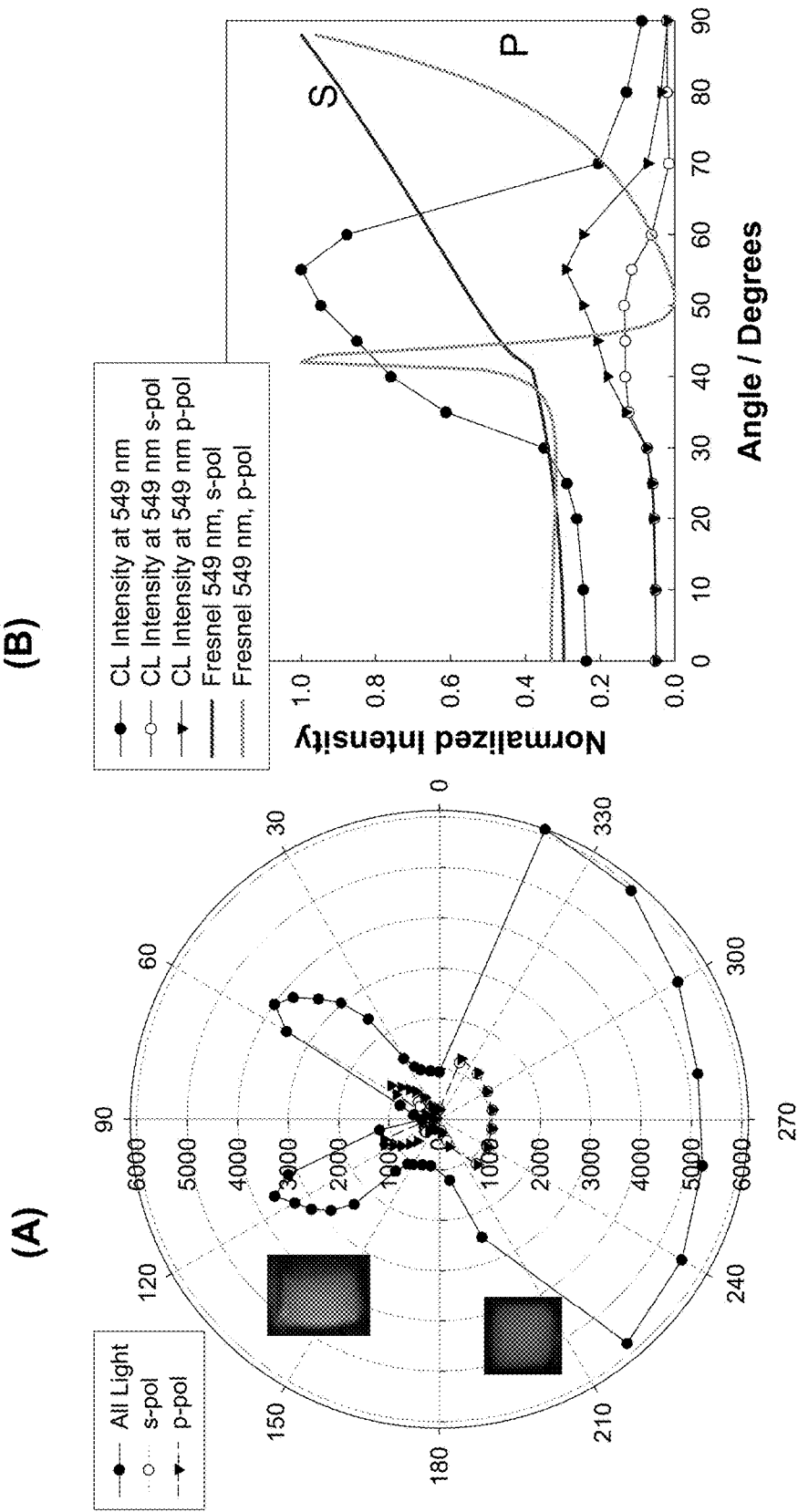
FIG. 26 (A) Polar plot of green SPCC (0-180 degrees) and free space chemiluminescence (180-360 degrees) with photographs of coupled (top) and free space (bottom) emissions (B) normalized intensity curves of green chemiluminescence emission, s-polarized emission, and p-polarized emission from 100 µL of dye on a 15 nm Pd slide compared with the theoretical Fresnel curves.
Figure 27:
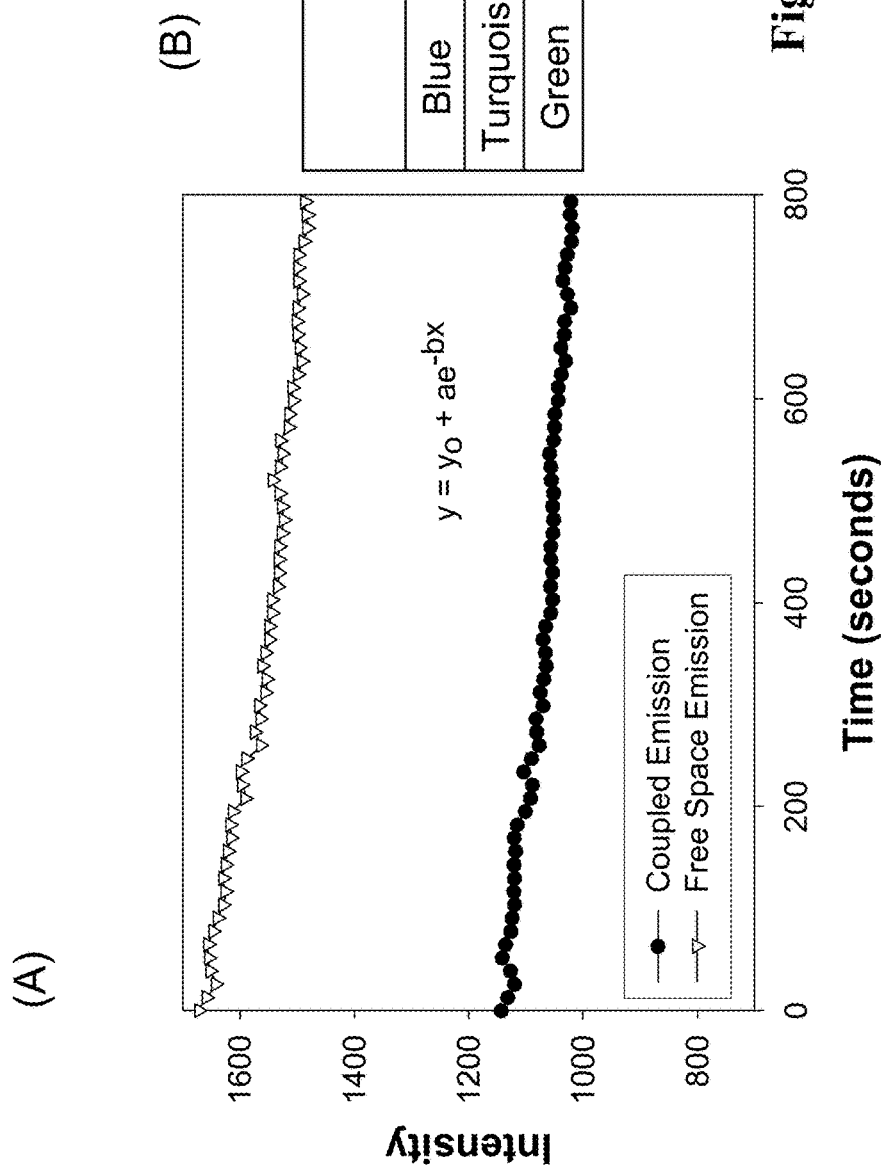
FIG. 27 shows decay rates (A) The free space and coupled emission decay curves for blue chemiluminescence measured at 492 nm (B) coupled and free space decay rates for blue, turquoise, and green chemiluminescence.

The above discussed effect were also found to be related to thin Palladium films as shown in FIGS. 23-27. FIGS. 24-26 show the angular-dependent SPCC (0-180 degrees, back of the hemispherical prism) and free-space (180-360 degrees, sample side) p- and s-polarized emission from the blue (at 492 nm, FIG. 24A), green (at 509 nm, FIG. 25A) and turquoise (549 nm, FIG. 26A) chemiluminescent solution. A highly p-polarized and highly directional SPCC emission is observed for all chemiluminescent solutions. P-polarized SPCC emission was at a maximum at observation angles of ≈55 and 110 degrees.

Figure 28:
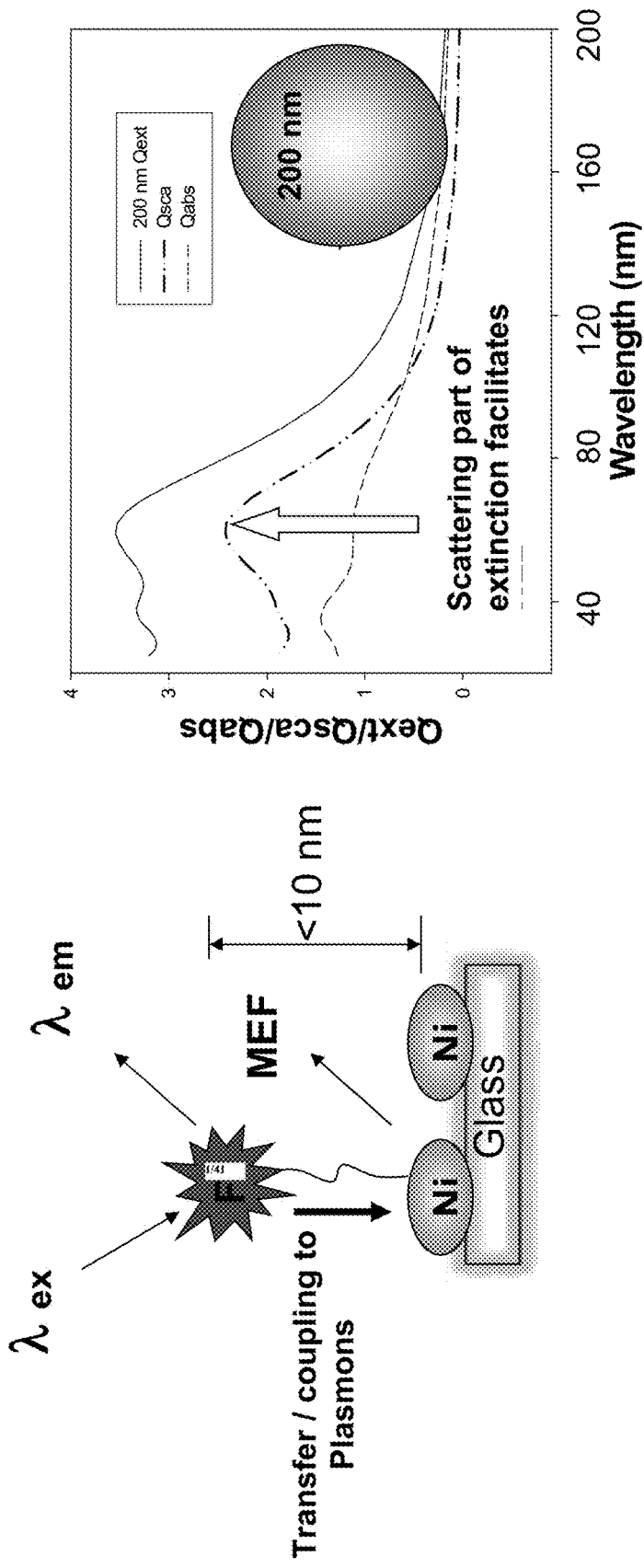
FIG. 28 shows (left) a schematic representation of Metal-Enhanced Fluorescence. (Right) Calculated Mie extinction, scattering and absorption cross section for a 200 nm Ni nanoparticle.

It has been determined that the mechanistic interpretation of MEF is underpinned by a model whereby non-radiative energy transfer occurs from excited distal fluorophores to surface plasmons in non-continuous films (FIG. 28—Left), in essence a fluorophore induced mirror dipole in the metal. The surface plasmons, in turn, radiate the photophysical characteristics of the coupling fluorophores. In essence, the system radiates as a whole. As a result, the system exhibits modified overall radiative rates. Ultimately, the increased radiative rate for the system lends to enhanced fluorescence signals or (increased system quantum yields) for fluorophores in close proximity to metallic structures, Nickel nanodeposits of various thicknesses were deposited, using thermal vapor deposition, onto glass microscope slides. FIG. 28 right shows the comparison of the scattering and absorption cross section of a 200 nm Nickel nanoparticle (spherical) in air calculated using traditional Mie theory. The extinction spectrum is dominated by the scattering component from the Visible to the NIR range. It is therefore expected that close-proximity fluorophores would demonstrate enhanced properties near-to nickel nanoparticles, where the fluorophore emission spectral overlap with the scattering portion of the nanoparticle extinction, provides for the plasmon-coupling enhancement effect in MEF.

Several fluorophores with emission wavelengths maximum ranging from 420-810 nm and with different free-space quantum yields were deposited onto Nickel substrates in a sandwich sample format. Enhancement of fluorescence emission from fluorophores was both compared and observed.

All fluorophores including Perylene, I R792, fluorescein isothiocyanate (FITC), Acridine Orange, Rose Bengal, Rhodamine 101 and Nile Blue were obtained from Sigma-Aldrich Chemical company and used as received. Silane Prep™ glass microscope slides were purchased from Sigma-Aldrich. Nickel nanostructured films of various thicknesses were deposited onto Silane-prep™ glass microscope slides using thermal vapor deposition, AccuCoat, Inc. Rochester, N.Y., USA. A solution of 200 L of a fluorophore (500 M) was sandwiched between two glass slides for the control sample and between one glass and one Nickel nanostructured film, or between two Nickel nanostructured films respectively. Each dye was excited with a source of appropriate wavelength and the fluorescence emission spectra measured as described below.

Figure 29:
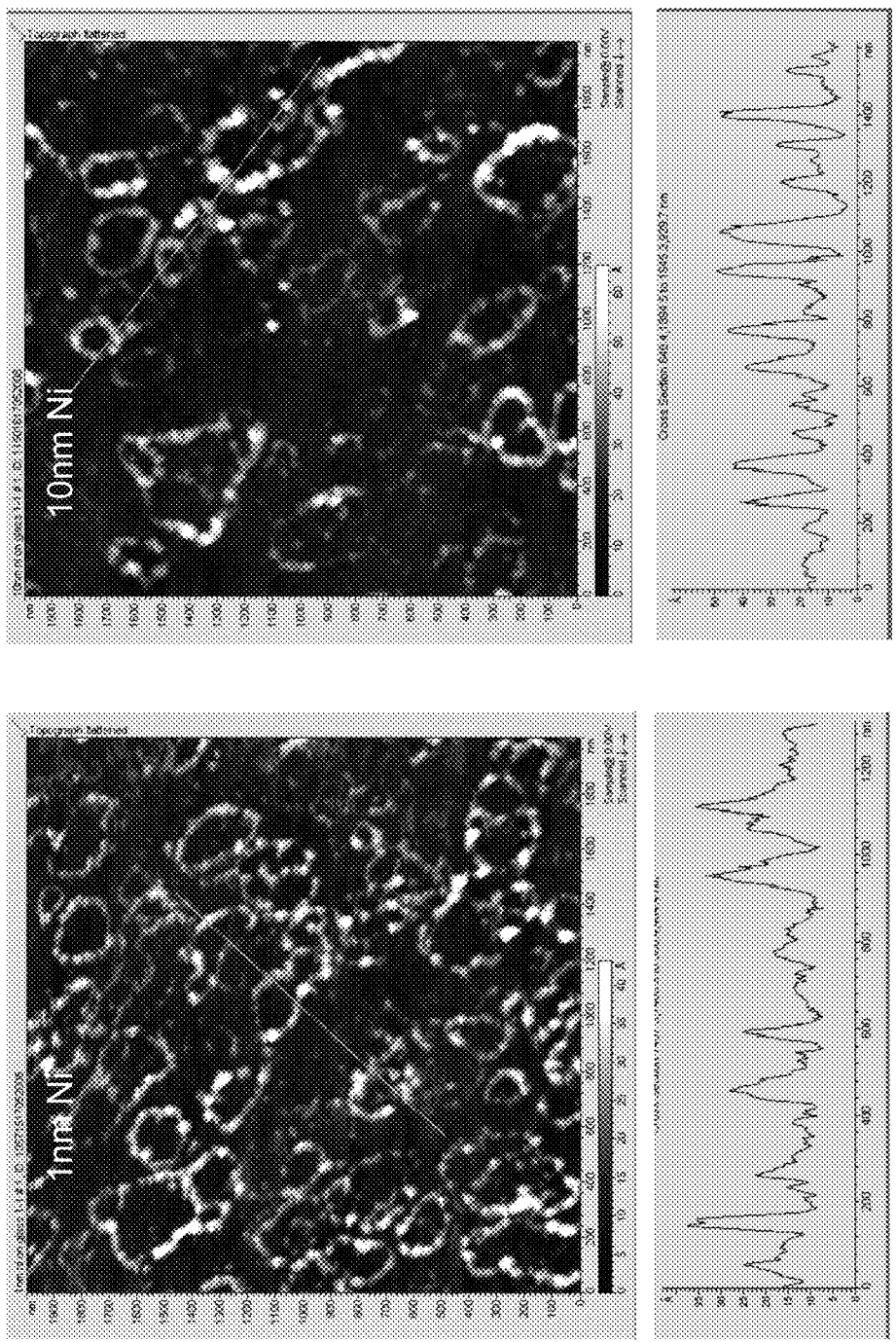
FIG. 29 shows AFM images of (Left) 1 nm Ni on glass (Right) 10 nm Ni on glass. Bottom images are the respective line scans of AFM images for 1 nm Ni on glass and 10 nm Ni on glass.
Figure 30:
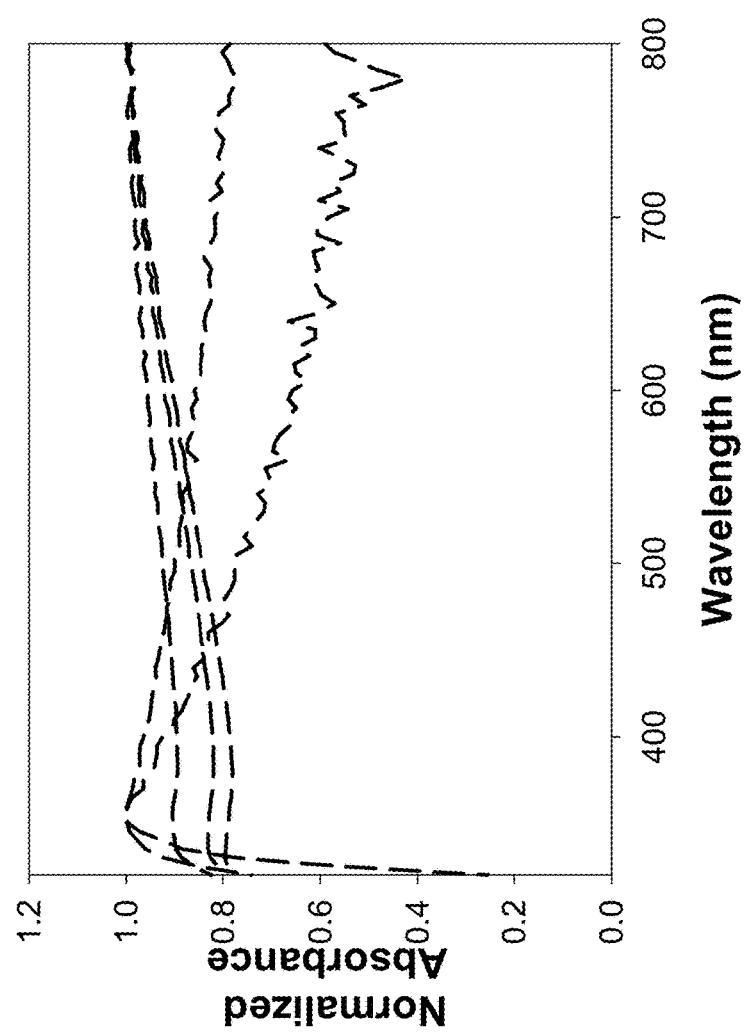
FIG. 30 shows normalized absorption spectrum of vapor deposited metallic Ni of various thicknesses, deposited onto glass slides.
Figure 35:
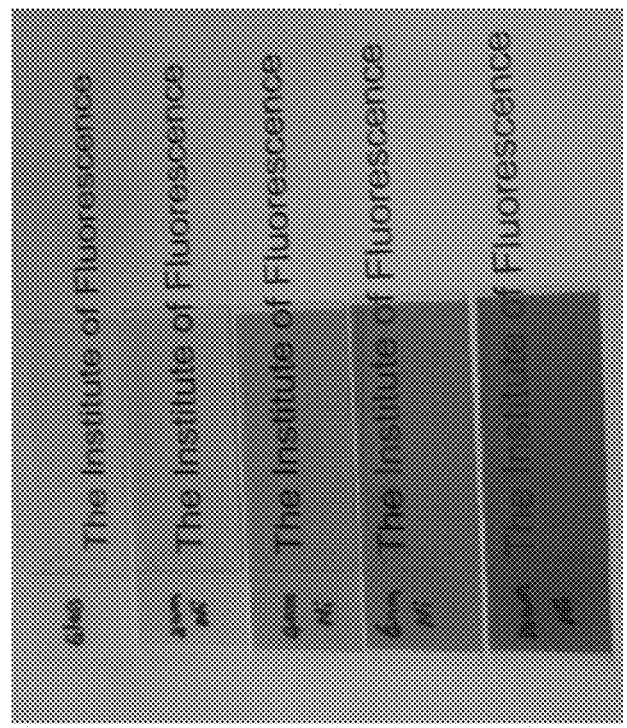
FIG. 35 shows the absorption spectrum of vapor deposited metallic Ni of various thicknesses deposited onto glass slides (Left). Photograph of glass and Ni slides with different thickness 2 nm, 4 nm, 6 nm, 10 nm (Right).
Figure 35:
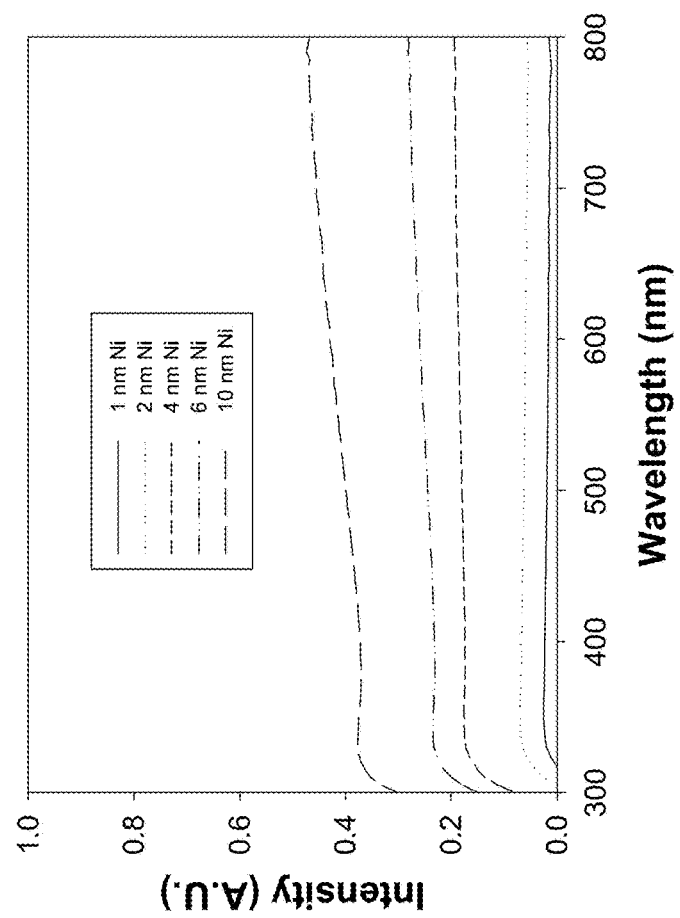
Figure 36:
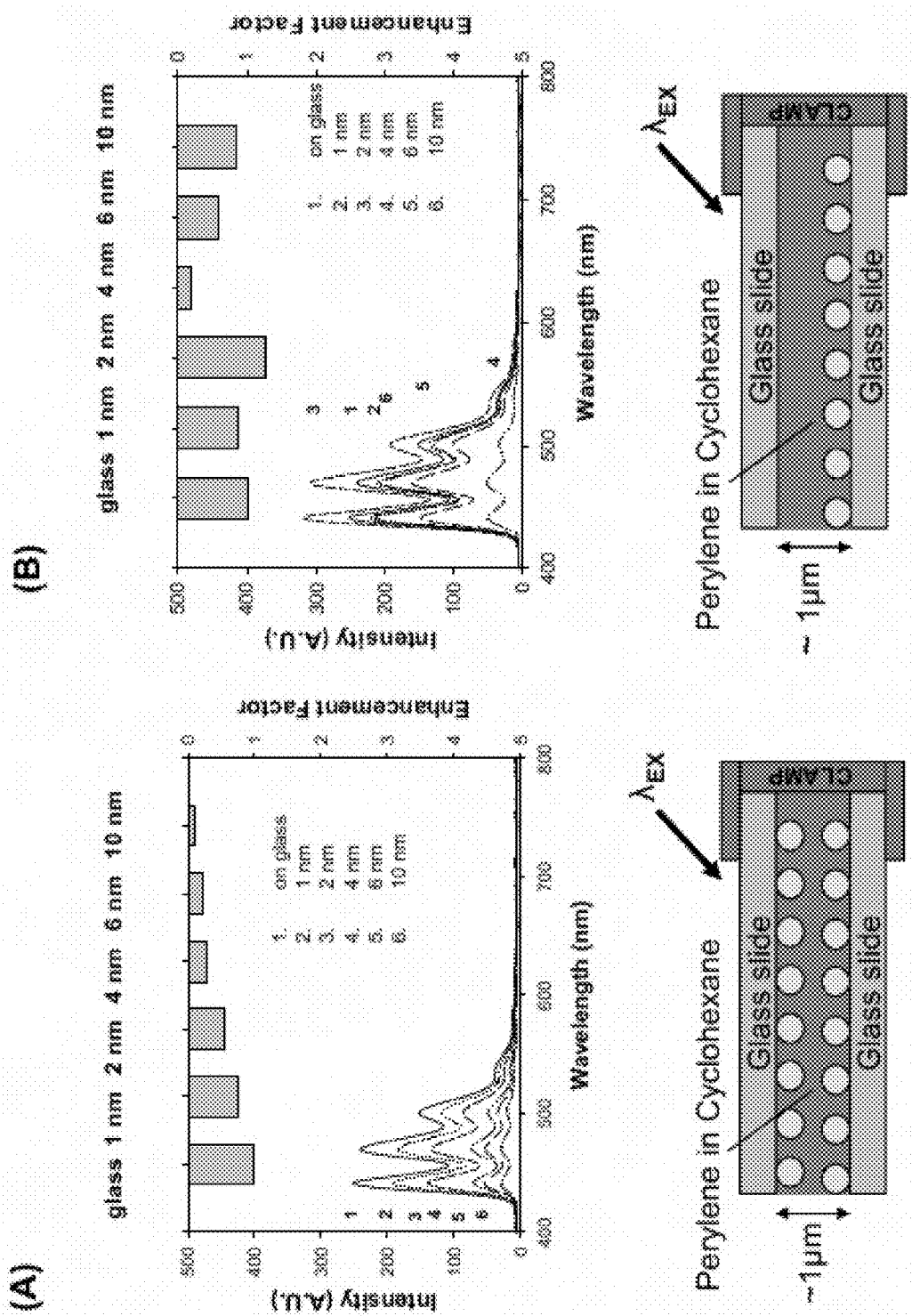
FIG. 36 shows (A) Emission spectra, enhancement factors and geometry schematic for a Perylene solution sandwiched between two Ni slides of varying thicknesses and (B) Perylene sandwiched between one blank glass slide and one Ni film glass slide.
Figure 37:
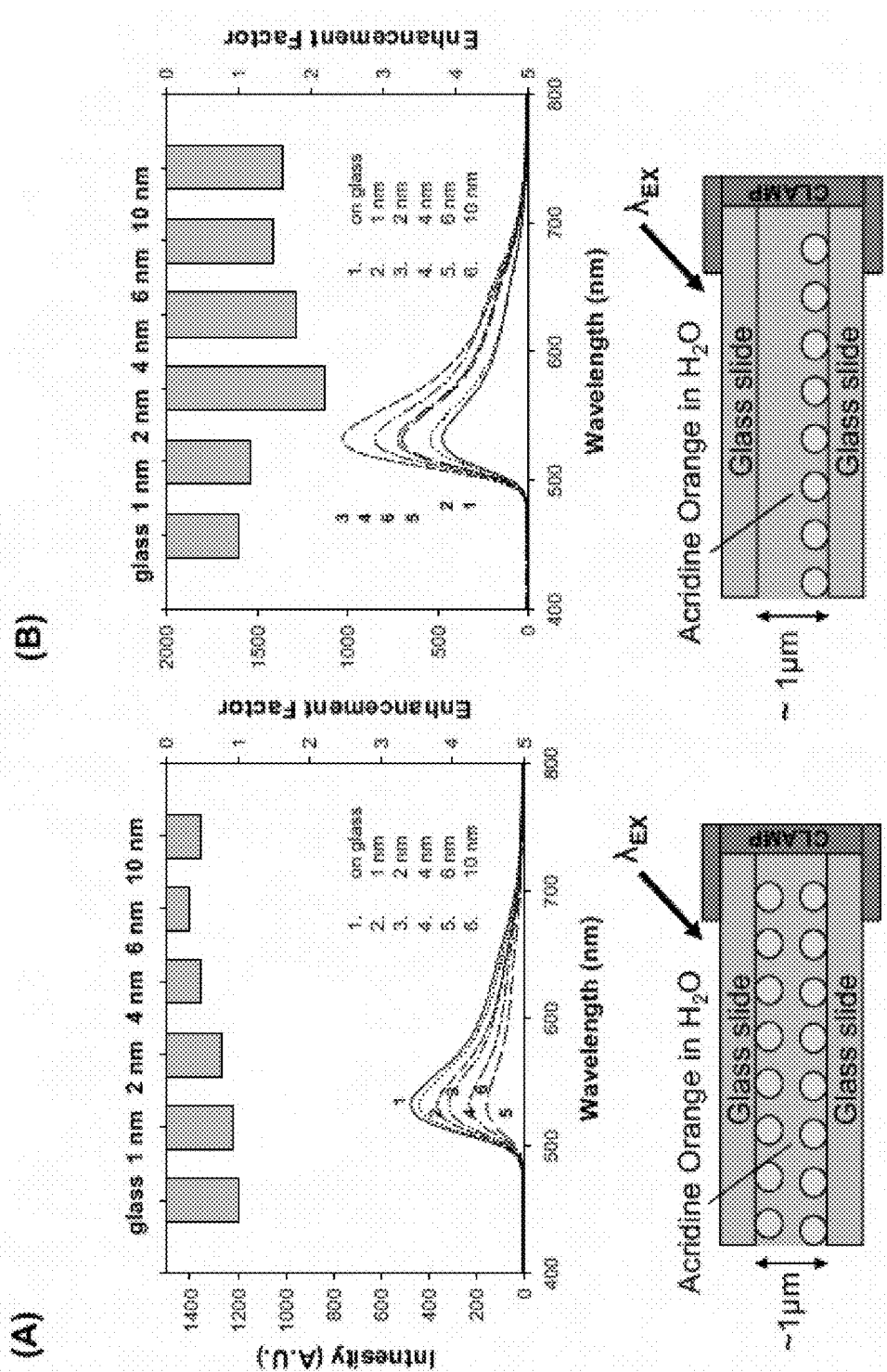
FIG. 37 shows (A) Emission spectra, enhancement factors and geometry schematic for Acridine Orange solutions sandwiched between two Ni slides of varying thicknesses and (B) Acridine Orange solutions sandwiched between one blank glass slide and one Ni film glass slide.
Figure 38:
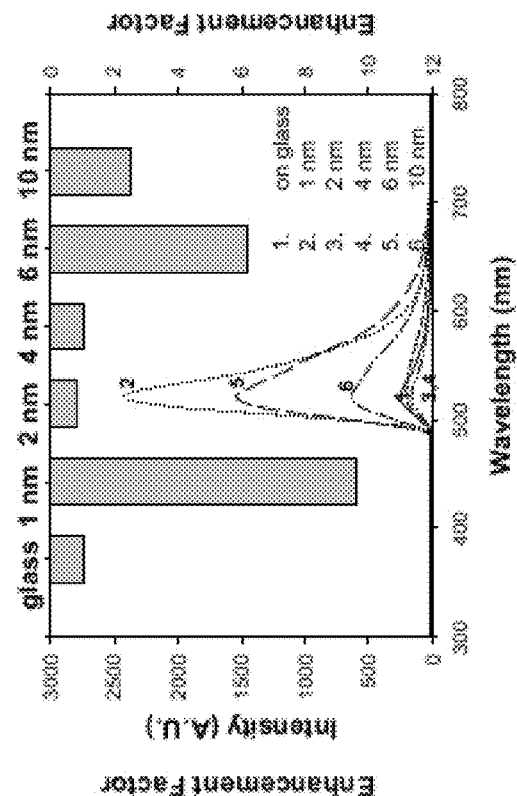
FIG. 38 shows (A) Emission spectra, enhancement factors and geometry schematic for FITC solution sandwiched between two Ni slides of varying thicknesses and (B) FITC sandwiched between one blank glass slide and one Ni film glass slide.
Figure 38:
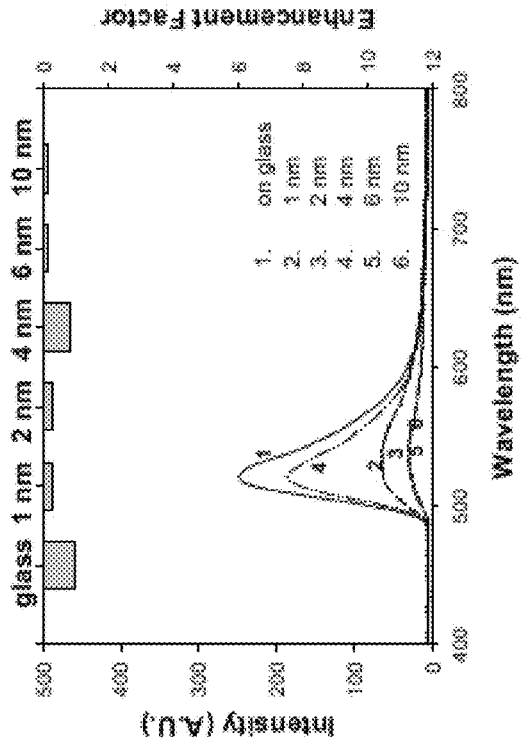
Figure 38:
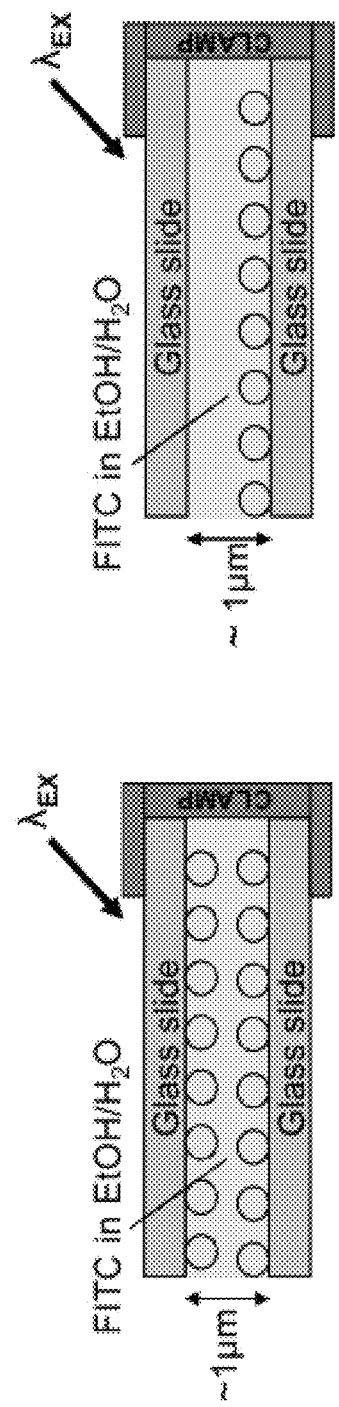
Figure 39:
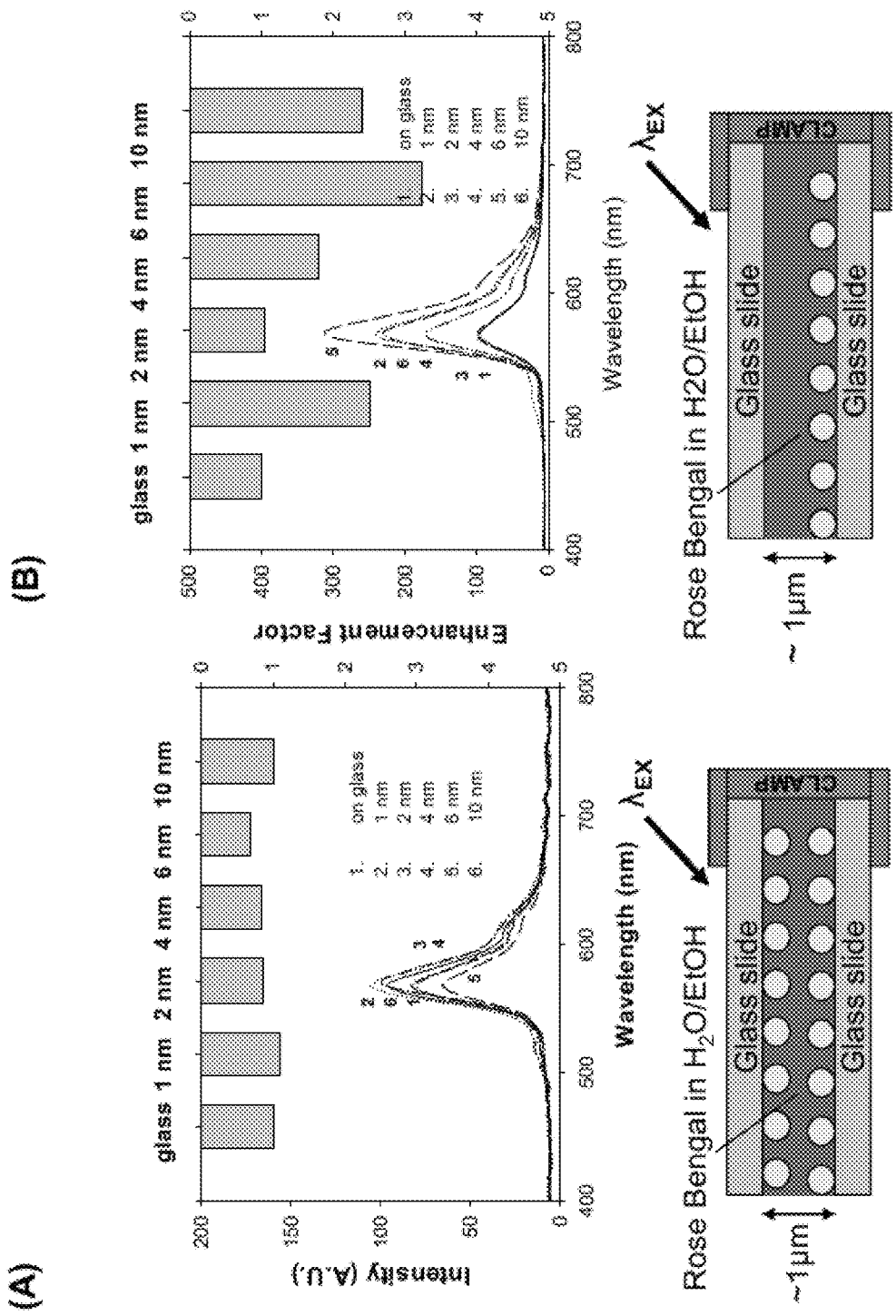
FIG. 39 shows (A) Emission spectra, enhancement factors and geometry schematic for Rose Bengal solutions sandwiched between two Ni slides of varying thicknesses and (B) Rose Bengal solution sandwiched between one blank glass slide and one Ni slide.
Figure 40:
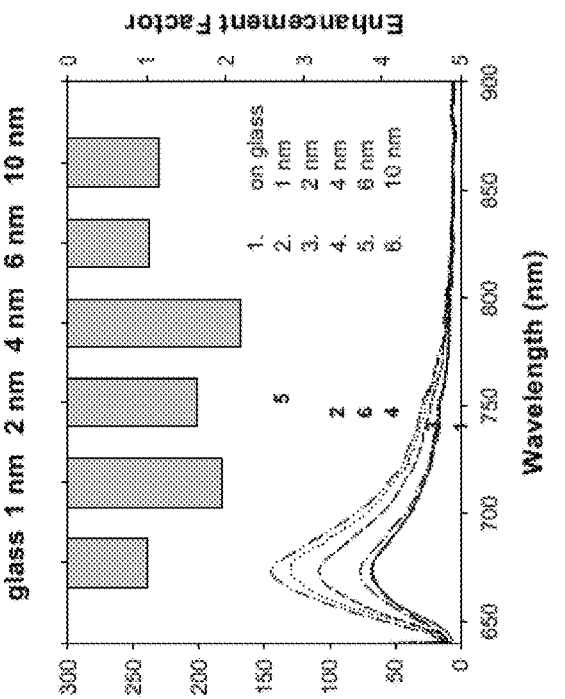
FIG. 40 shows (A) Emission spectra, enhancement factors and geometry schematic for Nile Blue solution sandwiched between two Ni slides of varying thicknesses and (B) Nile Blue solution sandwiched between one blank glass slide and one Ni slide.
Figure 40:
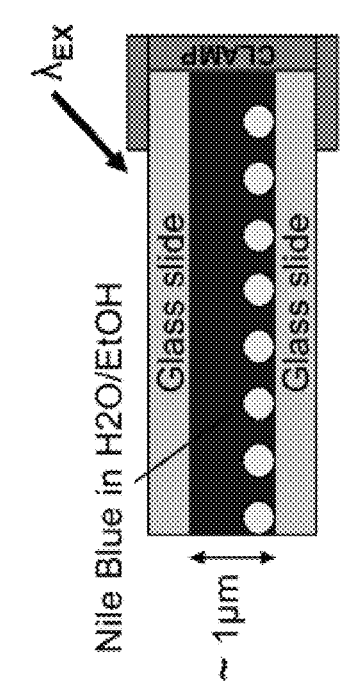
Figure 40:
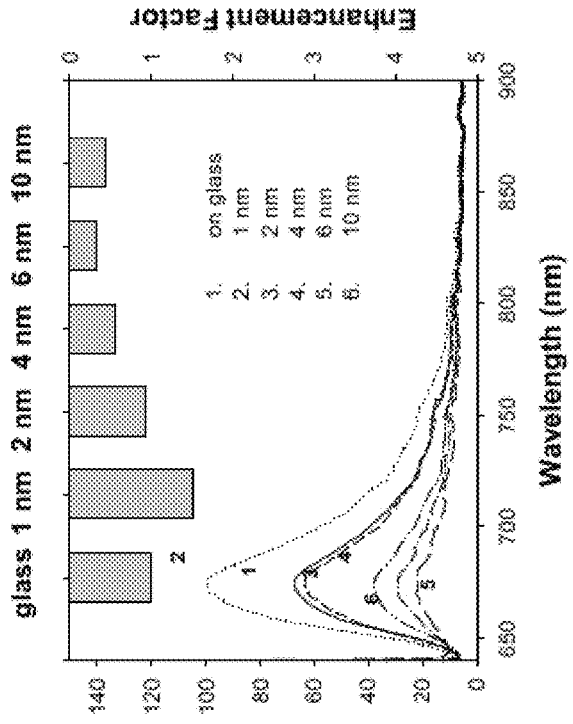
Figure 40:
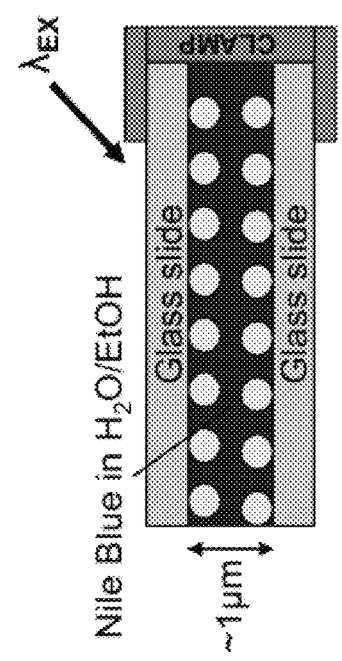
Figure 41:
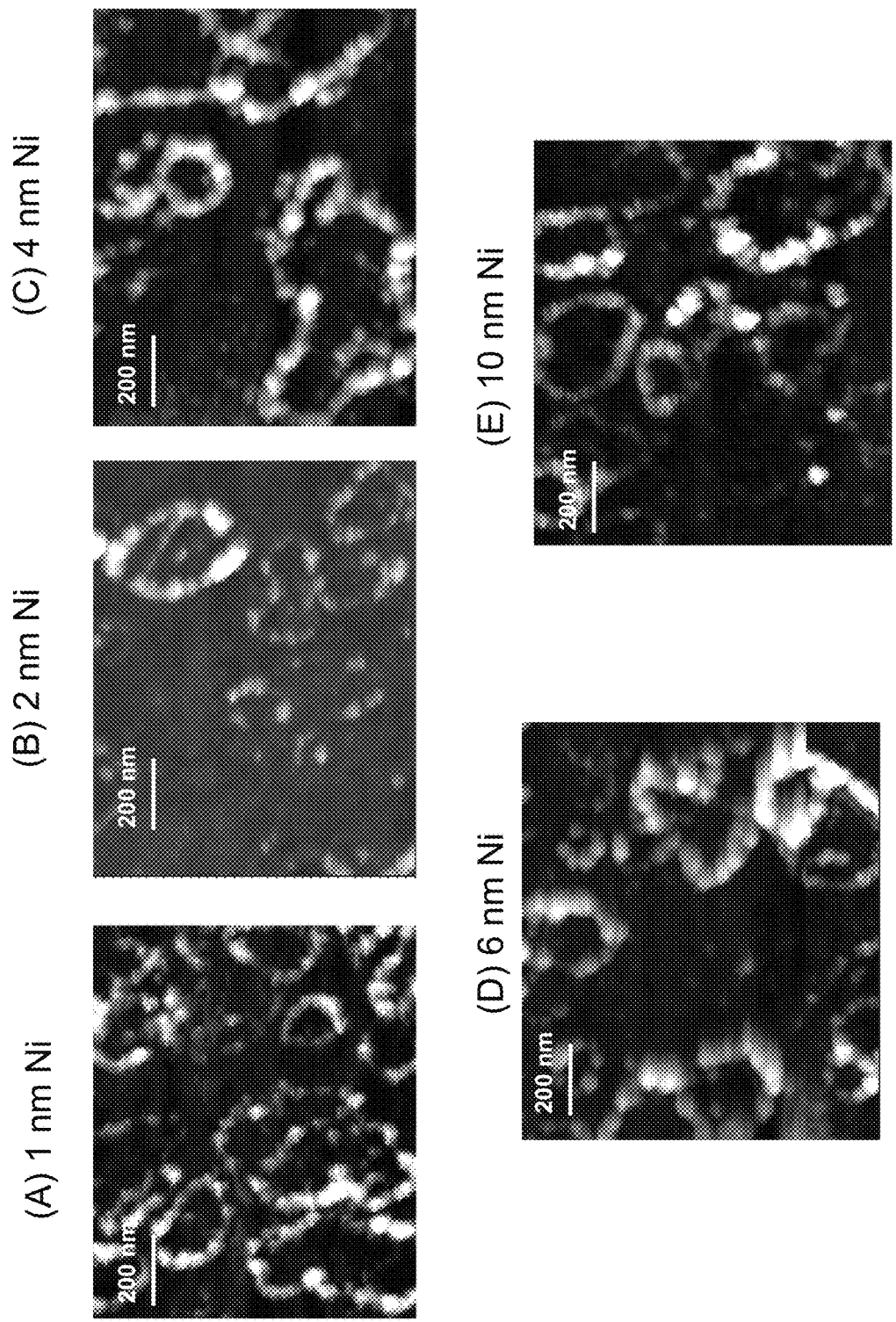
FIG. 41 shows AFM images of (A) 1 nm Ni on glass, (B) 2 nm Ni on glass, (C) 4 nm Ni on glass, (D) 6 nm Ni on glass, (E) 10 nm Ni on glass. The thicknesses of the Ni nanostructured films were measured by the micro quartz balance in the metal evaporator.

The morphology of different thickness of nickel films was studied using AFM. AFM images of 1 and 10 nm Ni films are shown in FIG. 29 and other thicknesses of Ni films are provided in FIG. 41. From FIG. 29, it can be seen that separated islands were formed when 1 and 10 nm Ni were deposited on the glass slides. However, for the 1 nm Ni film, the height of the islands was below 2 nm, as seen from the line scan results. For the 10 nm Ni film (FIG. 29 right), the height of the separated islands was below 3 nm which was much lower than the thickness of the Ni film measured by the quartz crystal microbalance (QCM). It can be concluded from the AFM images that for 1 nm Ni samples, only one layer of separated Ni islands was formed on the glass slides due to the height of the islands being close to the Ni film thickness measured by the QCM. By increasing the Ni film thickness, separated Ni islands form a continuous film on the glass slide, with the top layer covered by aggregated Nickel islands. The optical absorbance of the Ni films was subsequently measured. FIG. 30 shows the normalized absorption spectra of 1, 2, 4, 6, and 10 nm thick nickel nanodeposits. Nickel nanodeposits of 1 and 2 nm show an absorbance peak around 380 nm, suggesting a particulate film. With increasing thickness, a broad absorption spectrum was observed, which is indicative of the aggregation of the nanodeposits on the surface forming a continuous film, as is observed for silver nanoparticulate deposits. In FIG. 35, the absorbance spectra of the different thicknesses of the Ni deposits and the respective photographs, show their transparency, with decreased loading.

Figure 31:
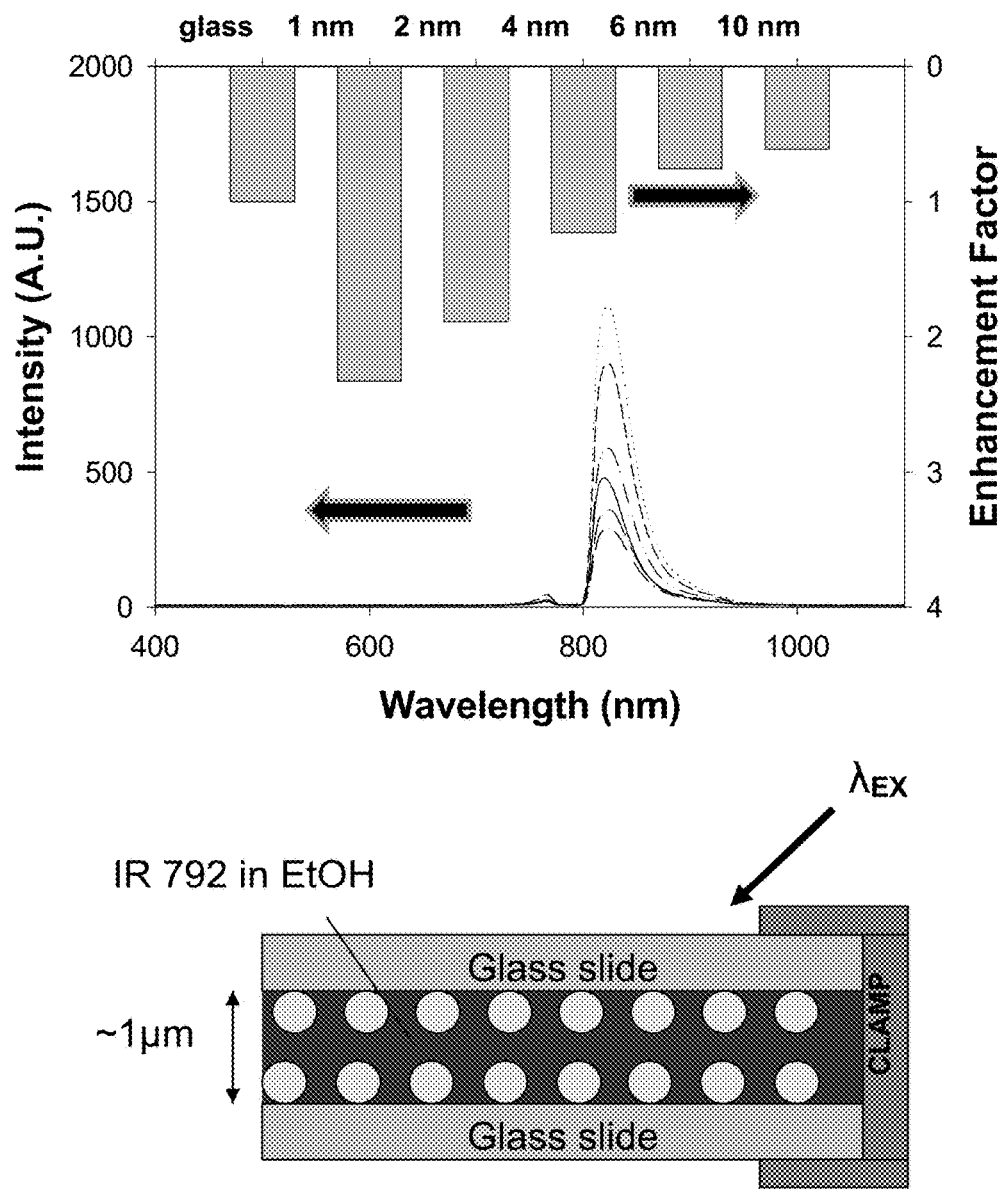
FIG. 31 shows emission spectra and fluorescence enhancement factors (top) geometry schematic (Bottom) for a solution of IR792 sandwiched between two Ni slides of varying thickness.

The fluorescence emission spectra of IR792 on different thickness Ni films and on glass are shown in FIG. 31. FIG. 31 (bottom) shows the metal sandwich format. It can be seen that the fluorescence of IR792 is enhanced (2.5 fold) for 1 nm Ni, as compared to the glass control sample i.e. no metal, with the enhancement factor decreased with increased Ni thickness. The fluorescence was diminished when the Ni thickness was greater than 6 nm, which from both the AFM analysis and absorption spectra revealed that continuous films were formed. This finding is consistent with trends observed for continuous and particulate silver[17] and gold films[24] and their influence on MEF. The distance between the sandwich slides was estimated to be ≈1 μm, and in this geometry only ≈4% of the solution is believed to be in the plasmon enhancing range.[17] This suggests the near-field enhanced fluorescence is ≈50 fold brighter.

Figure 32:
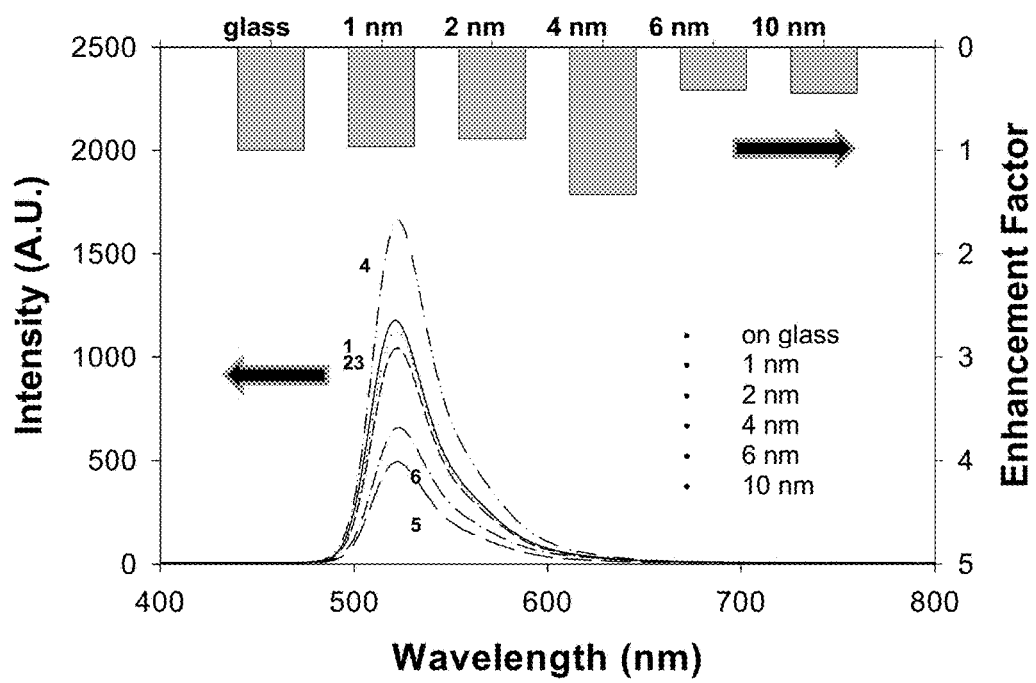
FIG. 32 shows the emission spectra and fluorescence enhancement factors (Top) geometry schematic (Bottom) for a Rhodamine 101 solution sandwiched between two Ni slides of varying thickness.
Figure 32:
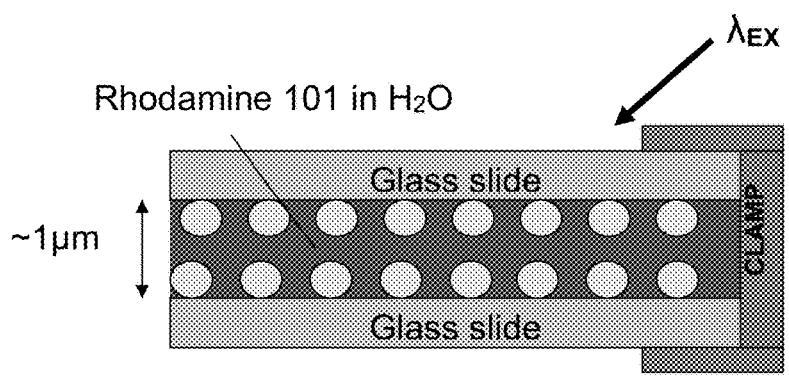

The fluorescence emission spectra of Rhodamine 101 on different thickness Ni films and on glass are shown in FIG. 32. For the different thicknesses of Ni on glass slides, as compared to bare glass slides, no enhanced fluorescence was observed. For Rhodamine 101, the emission peak is located at ≈530 nm, however for IR792, the emission peak is located at ≈820 nm, this finding suggesting a wavelength dependence of metal-enhanced fluorescence on the Ni films.

In addition, several other fluorophores were studied on nickel substrates and are given in FIGS. 36-40 wherein the fluorescence intensity for Perylene, FITC, Acridine Orange, Rose Bengal and Nile Blue is apparently quenched in a conventional metal-metal (Ni—Ni) sandwich format. Interestingly, for a metal-glass sandwich, i.e. Ni-glass, the apparent quenching is not observed, with significant enhancements observed for some fluorophore: Ni combinations. As shown in FIG. 35—right, thicker Ni films are no longer transparent or indeed particulate.

Figure 33:
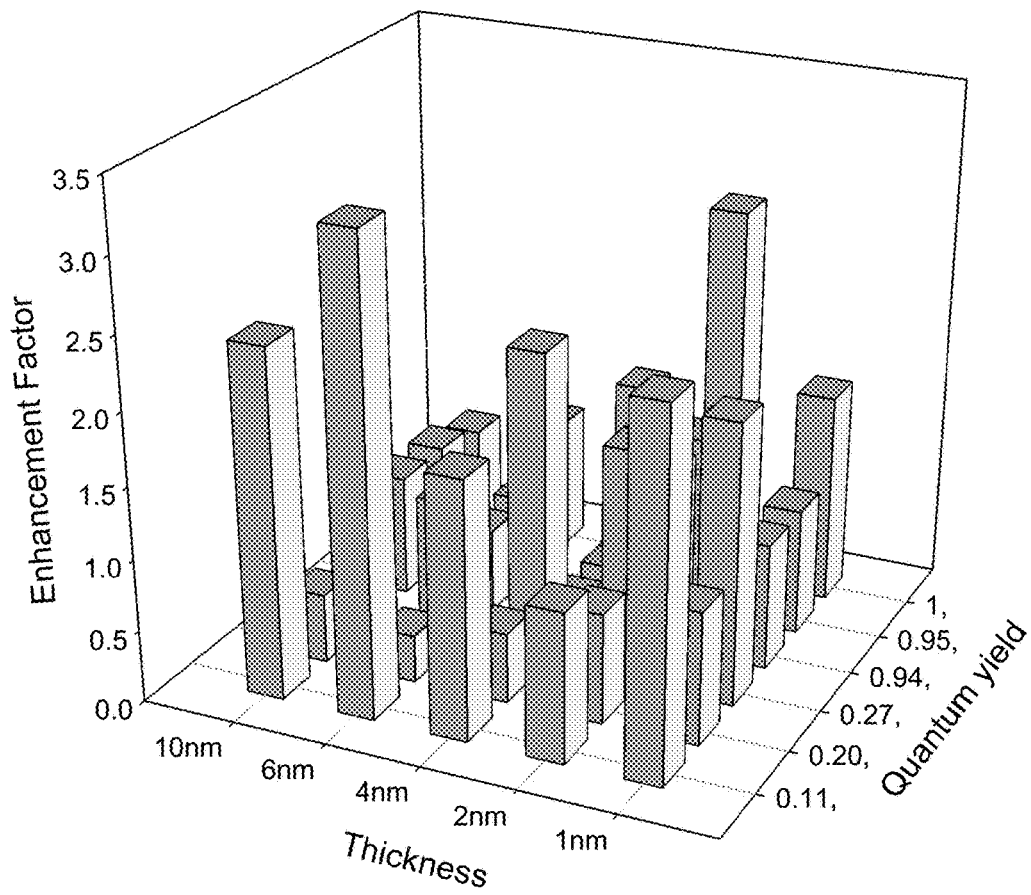
FIG. 33 shows metal-enhancement factor form fluorophores sandwiched between glass and Ni slides correlated with Ni firm thickness and fluorophore free-space quantum yield, $Q_0$.

FIG. 33 summarizes the enhancement factors observed for the fluorophores studied. Interestingly, fluorophores with the lowest free-space quantum yield appear to be enhanced the most, consistent with recent reports from our laboratory[33].

Figure 34:
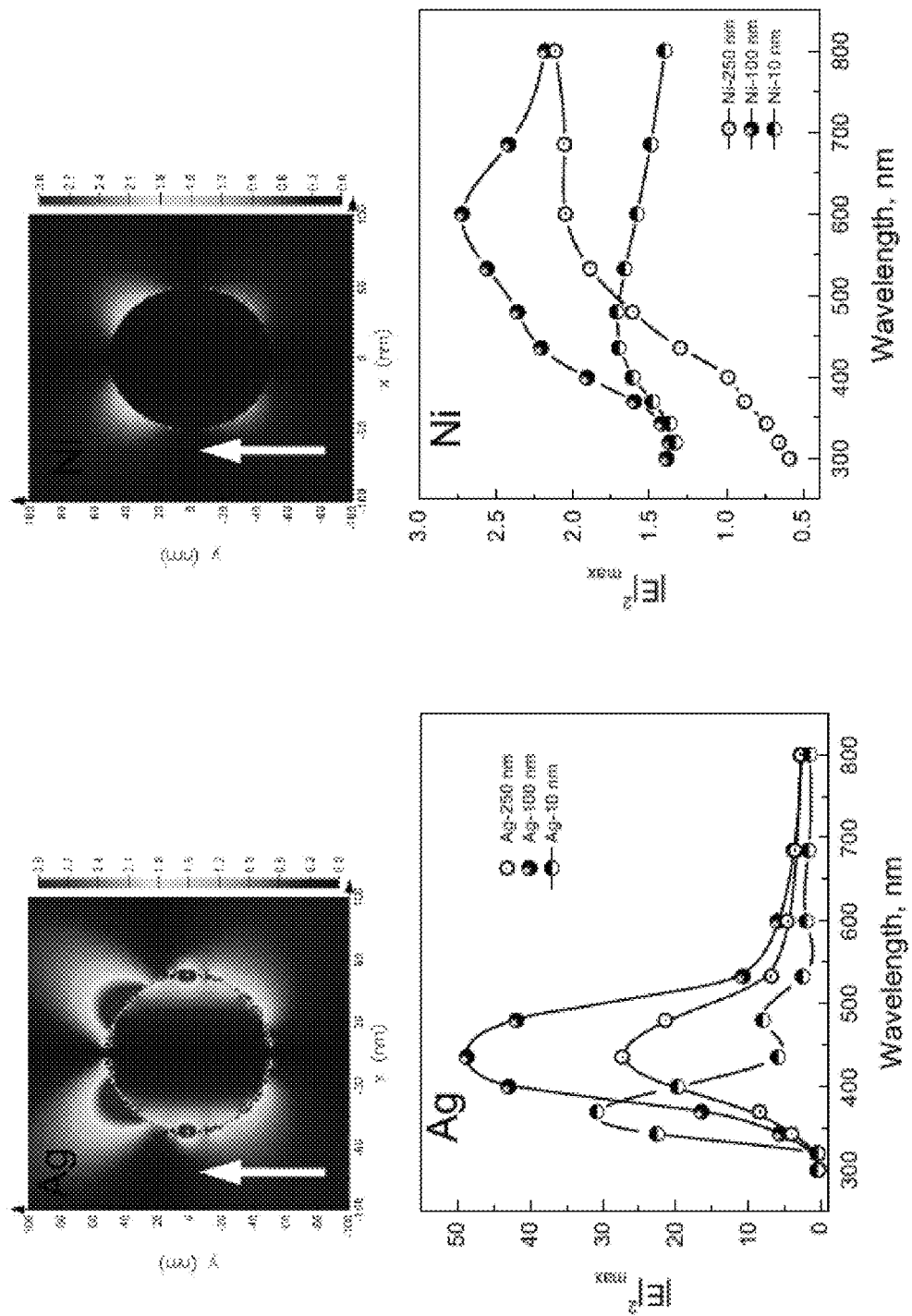
FIG. 34 shows the dependence of electric field maximum intensity upon wavelength of the incident light, Bottom. Calculations were undertaken using FDTD simulations for Ag and Ni nanoparticles of sizes, 10, 100, 250 nm (diameter). Top, typical images of near-field intensity distribution around 100 nm Ag- and Ni-nanoparticles. While arrow shows direction of the incident light injection. FDTF-Finite Difference Time Domain.

When a luminophore is placed near-to metal, there is often a very strong net absorption effect caused by the localized enhanced electromagnetic field of the incident excitation field. In essence, conducting metallic particles can modify the free space absorption condition in ways that increase the photonic mode density and incident electric field felt by a luminophore. Since enhanced electromagnetic fields in proximity to metal nanoparticles are the basis for the increased system absorption in MEF, the electric field enhancements (using FDTD calculations) were calculated for Nickel nanostructures on a planar surface (FIG. 34). 10, 100 and 250 nm diameter particles were chosen for the calculation. For Ni, FDTD calculations show that the maximum electric field intensity, is predicted to occur over a broad range of wavelengths ≈300-800 nm range. In contrast, for silver which is widely used in MEF,[36, 34] the range of wavelengths is much narrower from 400 to 500 nm. More importantly, the calculations shown in FIG. 34 predict that Nickel nanoparticles can be used for MEF applications with fluorophores in a wide spectral range, which an intensity maximum in the near IR, unlike the widely used silver[35,36].

It has been suggested that the typically short lifetime observed for fluorophores near-to metallic nanoparticles, is indeed indicative of the Plasmon lifetime itself[37], recalling that the coupled fluorophore quanta is radiated from the nanoparticles.[37] In this regard, the lifetime of FITC near-to nickel substrates was measured. The experimental geometry and the overall results for the lifetime of FITC are given in Table 3.

|  | Lifetime (ns) | $X^2$ |
| --- | --- | --- |
| FITC In cuvette | 4.3 | 1.0 |
| FITC/glass | 4.2 | 0.9 |
| FITC/1 nm Ni glass | 3.8 | 1.0 |
| FITC/6 nm Ni glass | 2.6 | 1.1 |
| FITC/10 nm Ni glass | 2.6 | 1.0 |

The lifetime of FITC on glass substrates (sandwich format: glass/FITC/glass) is similar to that for FITC in a cuvette, as expected. Table 3 shows that the lifetime of FITC on glass, 1, 6, and 10 nm Ni substrates are 4.2, 3.8, 2.6, 2.6 ns respectively. Subsequently, the lifetime of the fluorophore-metal system is reduced due to a faster and more efficient fluorophore-plasmon emission.[37]

Fluorophores with different emission wavelength maxima and quantum yields in close proximity to Nickel nanoparticles, can undergo enhanced fluorescence, a 2.5-fold increase was observed from 1 nm Ni films from IR792 with up-to a 10-fold enhancement observation for FITC. When fluorophores were placed in close-proximity to the substrates, metal-enhanced fluorescence (MEF) was observed. The wavelength dependence of the metal-enhanced fluorescence correlated with numerical finite-difference time-domain simulations showing a maximum for the enhanced electric field of Ni nanoparticles around 600 nm. In addition, the decay times of fluorophores was also reduced near-to the Ni substrates, suggesting both an enhanced electric field and a plasmon-coupling component is the mechanism for fluorescence enhancement, similar to substrates made from silver, copper and gold nanoparticles.

REFERENCES

The contents of the reference cited herein are incorporated by reference herein for all purposes.
(1) Liebermann, T.; Knoll, W. (2000) *Colloids and Surfaces A—Physicochemical and Engineering Aspects,* 171, 115-130.
(2) Yu, F.; Persson, B.; Lofas, S.; Knoll, W. (2004) *J Am Chem Soc,* 126, 8902-8903.
(3) Kwon, S. H.; Hong, B. J.; Park, H. Y.; Knoll, W.; Park, J. W. (2007) *J Colloid Interface Sc,* 308, 325-331.
(4) Liu, J.; Tiefenauer, L.; Tian, S.; Nielsen, P. E.; Knoll, W. (2006) *Anal Chem,* 78, 470-476.
(5) Tawa, K.; Yao, D.; Knoll, W. (2005) *Biosens Bioelectron,* 21, 322-329.
(6) Aslan, K.; Malyn, S, N.; Geddes, C. D. (2007) *Journal of Immunological Methods,* 323, 55-64.
(7) Aslan, K.; Previte, M. J.; Zhang, Y.; Geddes, C. D. (2008) *Anal Chem,* 80, 7304-7312.
(8) Liebermann, T.; Knoll, W.; Sluka, P.; Herrmann, R. (2000) *Colloids and Surfaces A—Physicochemical and Engineering Aspects,* 169, 337-350.
(9) Gryczynski, I.; Malicka, J.; Nowaczyk, K.; Gryczynski, Z.; Lakowicz, J. R. (2004) *Journal of Physical Chemistry B,* 108, 12073-12083.
(10) Gryczynski, I.; Malicka, J.; Gryczynski, Z.; Nowaczyk, K.; Lakowicz, J. R. (2004) *Analytical Chemistr,* 76, 4076-4081.
(11) Previte, M. J. R.; Zhang, Y. X.; Aslan, K.; Geddes, C. D. (2007) *Applied Physics Letter,* 91.
(12) Knoll, W. (1998) *Annu Rev Phys Chem,* 49, 569-638.
(13) Knoll, W.; Zizlsperger, M.; Liebermann, T.; Arnold, S.; Badia, A.; Liley, M.; Piscevic, D.; Schmitt, F. J.; Spinke, J. (2000) *Colloids and Surfaces A—Physicochemical and Engineering Aspects,* 161, 115-137.
(14) Barnes, W L, (2005) *Journal of Modern Optics* 45, 661.
(15) K H Drexhage, K H, (1970): J. Luminesc, 693.
(16) Aslan, K., Badugu R., Lakowicz, J. R., Geddes, C. D, (2005) *Journal of Fluorescence* 15, 99-104.
(17) C. D. Geddes, C D and J. R. Lakowicz, J R., (2002) *Journal of Fluorescence* 12, 121-129.
(18) Aslan, K., Lakowicz, J. R., Szmacinski, H., and Geddes, C. D., (2004) *Journal of Fluorescence* 14, 677-679.
(19) Aslan, K., Malyn, S. N., Bector, G., and Geddes, C. D., (2007) *Analyst* 132, 1122-9.
(20) Aslan, K., Previte, M. J. R., Zhang, X. Y., Baillie, L., and Geddes, C. D., (2007) *Biophysical Journal,* 552A-552A.
(21) Aslan, K., Zhang, Y., Hibbs, S., Baillie, L., Previte, M. J., Geddes, C. D., (2007) *Analyst* 132, 1130-8.
(22) Aslan, K., Previte, M. J. R., Zhang and Geddes, C. D., (2008) Journal of Physical Chemistry C. 112, 18368-18375.
(23) Zhang, Z., Aslan, K., Previte, M. J. R., and Geddes, C. D. (2007) *Applied Physical Letters* 90, 173116.
(24) Aslan, K., Malyn, N., and Geddes, C. D., (2007) *J Fluoresc* 17, 7-13.
(25) Aslan, K., Lakowicz, J. R., and Geddes, C. D., (2005) *Analytical and Bioanalytical Chemistry* 382, 926-933.

(26) Aslan, K., Leonenko, Z., Lakowicz, J. R., and Geddes, C. D., (2005) *Journal of Physical Chemistry B* 109, 3157-3162.
(27) Aslan, K., Lakowicz, J. R., and Geddes, C. D., (2005) *Journal of Physical Chemistry B* 109, 6247-6251.
(28) Aslan, K., Lakowicz, J. R., Geddes, C. D., (2004) *Analytical Biochemistry* 330, 145-155.
(29) Pribik, R., Asian, K., Zhang, Z., and Geddes, C. D., (2008) *Journal of Physical Chemistry C.,* 112, 17969-17973.
(30) Taflove, A., and Hagness, S. C., (2000) *Computational Electrodynamics: The Finite-Difference Time-Domain Method,* 2nd ed. (Artech House, Norwood, Mass.
(31) Anantha, V., and Taflove, A., (2002) *Ieee Transactions on Antennas and Propagation* 50, 1337-1349.
(32) Strekal, N., Maskevich, A., Maskevich, S., Jardillier, J. C., Nabiev, I., (2000) *Biopolymers* 57, 325-8.
(33) Zhang, Y., Asian, K., Previte, M. J. R., and Geddes, C. D., (2008) *Proceedings of the National Academy of Sciences of the United States of America* 105, 1798-1802.
(34) Aslan, K., Leonenko, Z., Lakowicz, J. R., Geddes, C. D., (2005) *Journal of Fluorescence* 15, 643-654.
(35) *Metal-Enhanced Fluorescence: Application to High-Throughput Screening and Drug Discovery*; Vol., edited by K. Asian, I. Gryczynski, J. Malicka, J. R. Lakowicz, and C. D. Geddes (Wiley & Sons, New Jersey, (2005).
(36) Aslan, K., Gryczynski, I., Malicka, J., Matveeva, E., Lakowicz, J. R., and Geddes, C. D., (2005) *Current Opinion in Biotechnology* 16, 55-62.
(37) Aslan, K., Zhang, Y. X., and Geddes, C. D., (2008) *Journal of Applied Physics* 103, 084307.

That which is claimed is:

1. A method of metal-enhanced luminescence sensing, comprising:
    applying a continuous metallic thin film consisting of Ni to a substrate used in a detection system, wherein the substrate is glass, quartz, cellulose, polymeric material or a combination thereof and the metallic thin film consisting of Ni is immobilized on the surface and is from 15 nm to 20 nm thick;
    introducing at least one excitable molecule for disposing near the metallic thin film, wherein the excitable molecule is capable of a chemically induced excited state or radiatively excited state and wherein the excitable molecule is positioned in a range from about 4 nm to 20 nm to the metallic thin film;
    triggering the chemically induced excited state or radiatively excited state of the excitable molecule; and
    detecting directional emissions for measuring emitted luminescent intensity, wherein the directional emissions are within a fixed 10 degree wide observation angle, located between 60 and 70 degrees from the normal of the surface.

2. The method of claim 1, wherein the luminescence is chemiluminescence, bioluminescence or fluorescence.

3. The method of claim 1, wherein the excitable molecule that is radiatively excited is a fluorophore.

4. The method of claim 3, wherein the fluorophore has an emission wavelength in the range of about 400 to 900 nm.

5. The method of claim 1, wherein the detected directional emissions are p-polarized emissions.

6. The method according to claim 3, wherein the metallic thin film of Ni has attached thereto a captured biomolecular probe with an affinity for a target molecule, and the method further comprises:
    contacting the captured biomolecular probe with a sample containing the target molecule wherein the target molecule binds to the captured biomolecular probe;
    introducing a free biomolecular probe with an affinity for the target molecule, wherein the free biomolecular probe has attached thereto the fluorophore, wherein binding of the free biomolecular probe to the target molecule causes the fluorophore to be positioned a sufficient distance from the thin metal film of Ni to enhance fluorescence emission when excited by an irradiating source.

* * * * *